(12) United States Patent
Margulies et al.

(10) Patent No.: US 12,403,118 B1
(45) Date of Patent: Sep. 2, 2025

(54) CANCER TREATMENTS USING MODIFIED FATTY ACIDS AND THE CARRIERS TO ADMINISTER THEM

(71) Applicant: Zetagen Therapeutics, Inc., Syracuse, NY (US)

(72) Inventors: Bryan S. Margulies, Liverpool, NY (US); Joe C. Loy, Weatherford, TX (US)

(73) Assignee: Zetagen Therapeutics, Inc., Syracuse, NY (US)

(*) Notice: Subject to any disclaimer, the term of this patent is extended or adjusted under 35 U.S.C. 154(b) by 0 days.

(21) Appl. No.: 19/071,647

(22) Filed: Mar. 5, 2025

(51) Int. Cl.
| | | |
|---|---|---|
| A61K 31/28 | (2006.01) | |
| A61K 31/485 | (2006.01) | |
| A61K 45/06 | (2006.01) | |
| A61K 47/02 | (2006.01) | |
| A61K 47/10 | (2017.01) | |
| A61K 47/12 | (2006.01) | |
| A61K 47/36 | (2006.01) | |
| A61P 35/00 | (2006.01) | |

(52) U.S. Cl.
CPC ............ *A61K 31/28* (2013.01); *A61K 31/485* (2013.01); *A61K 45/06* (2013.01); *A61K 47/02* (2013.01); *A61K 47/10* (2013.01); *A61K 47/12* (2013.01); *A61K 47/36* (2013.01); *A61P 35/00* (2018.01)

(58) Field of Classification Search
CPC ................................ A61K 31/28; A61P 35/00
See application file for complete search history.

(56) References Cited

U.S. PATENT DOCUMENTS

| | | |
|---|---|---|
| 6,713,488 B2 | 3/2004 | Sadee et al. |
| 11,471,454 B2 | 10/2022 | Margulies et al. |
| 2007/0197573 A1 | 8/2007 | Sadee et al. |
| 2019/0093109 A1 | 3/2019 | Thakur et al. |
| 2021/0030746 A1 | 2/2021 | Margulies et al. |
| 2021/0228571 A1 | 7/2021 | Margulies et al. |
| 2022/0016312 A1 | 1/2022 | Margulies et al. |

FOREIGN PATENT DOCUMENTS

| | | |
|---|---|---|
| WO | WO-2021/011529 A1 | 1/2021 |
| WO | WO-2022/015364 A1 | 1/2022 |

OTHER PUBLICATIONS

PubChem, "PubChem Compound Summary for CID 129650238, Lanthanum stearate", 2017, National Library of Medicine, 9 pgs. (Year: 2017).*

* cited by examiner

*Primary Examiner* — Jeffrey H Murray
*Assistant Examiner* — Madeline E Braun
(74) *Attorney, Agent, or Firm* — Foley & Lardner LLP

(57) ABSTRACT

Described herein are compositions comprising a lanthanide (III) modified fatty acid and methods of treating cancer with the composition. In particular, the application includes a lanthanide (III) modified fatty acid is a 9-R', 10-R" tri octadecanoate compound. This lanthanide (III) modified fatty acid can be combined with additional therapeutic agents, such as chemotherapeutic agents, radiopharmaceuticals, hormone therapies, CDK inhibitors, epigenetic modulators, selective estrogen receptor modulators, selective estrogen receptor degraders, aromatase inhibitors, phosphatidyl inositol-3-posphate kinase inhibitors, ATP-adenosine axis-targeting agents, signal transduction inhibitors, RAS signaling inhibitors, PI3K inhibitors, arginase inhibitors, HIF inhibitors, AXL inhibitors, PAK4 inhibitors, immunotherapeutic agents, immune checkpoint inhibitors, and agonists of stimulatory or co-stimulatory immune checkpoints.

5 Claims, 7 Drawing Sheets

Specification includes a Sequence Listing.

CANCER TREATMENTS USING MODIFIED FATTY ACIDS AND THE CARRIERS TO ADMINISTER THEM

FIELD

The present invention relates in general to pharmaceutical formulations, their uses for treating oncologic diseases and their methods of making and more specifically to controlled release pharmaceutical formulations, their uses, which may involve locoregional, intratumoral, administration, into fatty environment, as well as their methods of making.

SEQUENCE LISTING

The instant application contains a Sequence Listing which has been submitted electronically in XML format and is hereby incorporated by reference in its entirety. Said XML copy, created on Mar. 19, 2025, is named 118922-0330_SL.xml and is 8,650 bytes in size.

SUMMARY

One embodiment is a composition for treating cancer, comprising a fatty acid compound modified by a lanthanide (Ln) compound to form a lanthanide (III) 9-R', 10-R" octadecanoate compound that is then incorporated with a pharmaceutically acceptable carrier. In one aspect the lanthanide (III) 9-R', 10-R" octadecanoate compound is generated by selecting from the group comprising of the following fatty acids: lauric acid, palmitic acid, stearic acid, and oleic acid. The lanthanide (III) 9-R', 10-R" octadecanoate compound is also formed by using one of the lanthanide salts, which can be composed using any of the following lanthanides: lanthanum, cerium, praseodymium, neodymium, gadolinium, and terbium. Further, the lanthanide salt can be of the composition: $LnX_3$ in which X is one of the following: a chloride (e.g., $LnCl_3$), an acetate (e.g., $Ln(CH_3COO)_3$), a sulfate (e.g., $Ln_2(SO_4)_3$), or a nitrate (e.g., $Ln(NO_3)_3$). The lanthanide salt can take on the form of a lanthanide salt hydrate (e.g., $xH_2O$) or a lanthanide salt anhydrate (e.g., no $H_2O$), since heating a lanthanide salt hydrate results in the decomposition of the lanthanide salt hydrate into a lanthanide salt anhydrate. The lanthanide (III) 9-R', 10-R" octadecanoate compound is further produced using a novel chemical reaction.

In another embodiment, the lanthanide (III) 9-R', 10-R" octadecanoate compound, effects cell death by incorporation with the plasma membranes of cells. Changes membrane permeability and stiffness. Changes result in endocytosis. Endocytosis results in free-radical generation and ferroptosis-like reaction, resulting in cell death. Incorporation into mitochondria.

In another embodiment, a pharmaceutically acceptable carrier is soluble with fatty acids, tissues fat content, with lipophilic therapeutic molecules, with lipophilic drugs, with hydrophobic therapeutic molecules, and hydrophobic drugs. The pharmaceutically acceptable carrier is comprised of the lanthanide (III) 9-R', 10-R" octadecanoate compound, oleic acid, linoleic acid, guar gum, gum Arabic, carrageenan, sodium phosphate, titanium oxide, and sodium chloride solution.

In another embodiment, a method of treating a cancer comprising administering to a subject in need thereof an effective amount of a pharmaceutically acceptable carrier containing the lanthanide (III) 9-R', 10-R" octadecanoate compound and an OGFR antagonist, such as N-allyl noroxymorphone or a salt thereof. The method may further comprise administration of a pharmaceutically acceptable carrier containing the lanthanide (III) 9-R', 10-R" octadecanoate compound and one of the following classes of targeted therapy drugs or their salts thereof: selective estrogen receptor modulators (SERM), selective estrogen receptor degraders (SERD), aromatase inhibitors (AI), cyclin-dependent kinase-4/cyclin-dependent kinase (CDK4/6) inhibitors, or phosphatidyl inositol-3-posphate kinase (PI3K) inhibitors. The method may further comprise administration of a pharmaceutically acceptable carrier containing the lanthanide (III) 9-R', 10-R" octadecanoate compound and a combination of any of the following classes of targeted therapy drugs or their salts thereof: OGFR antagonists, SERMs, SERDs, Ais, CDK4/6 inhibitors, or PI3K inhibitors.

FIGURES

FIG. 1 illustrates a mechanism by which lanthanide (III) 9-R', 10-R" octadecanoate has an anti-tumorigenic effect. The diagram shows the incorporation of the lanthanide (III) 9-R', 10-R" octadecanoate within the cell membrane, which is composed of various lipids. Incorporation within the cell membrane (1) begins the process of endocytosis, which transportss the lanthanide (III) 9-R', 10-R" octadecanoate via the process of creating a vesicle (2) into the cytoplasm (3). The endocytotic vesicle fuses with a lysosome (4), which releases acid and enzymes that degrade fatty acid molecules. Once degradation is complete, the endocytotic vesicle releases the contents (5), which includes lipid-peroxidase molecules that produce free radical oxygen species (ROS) that can subsequently damage other cell organelles. In addition, elemental $Ln^+$ can also block calcium channels resulting in decreased cellular activity.

FIG. 2A-2B illustrate a mechanism by which elemental lanthanum has an anti-tumorigenic effect. FIG. 2A shows a standard cell, which shows calcium moving through calcium channels. FIG. 2B shows a cell contacted with lanthanum, which moves through calcium channels, and where calcium does not move through calcium channels. FIG. 2B also shows the cell contacted with N-allyl noroxymorphone, which may act as an OGFR antagonist.

DETAILED DESCRIPTION

Figure 1:
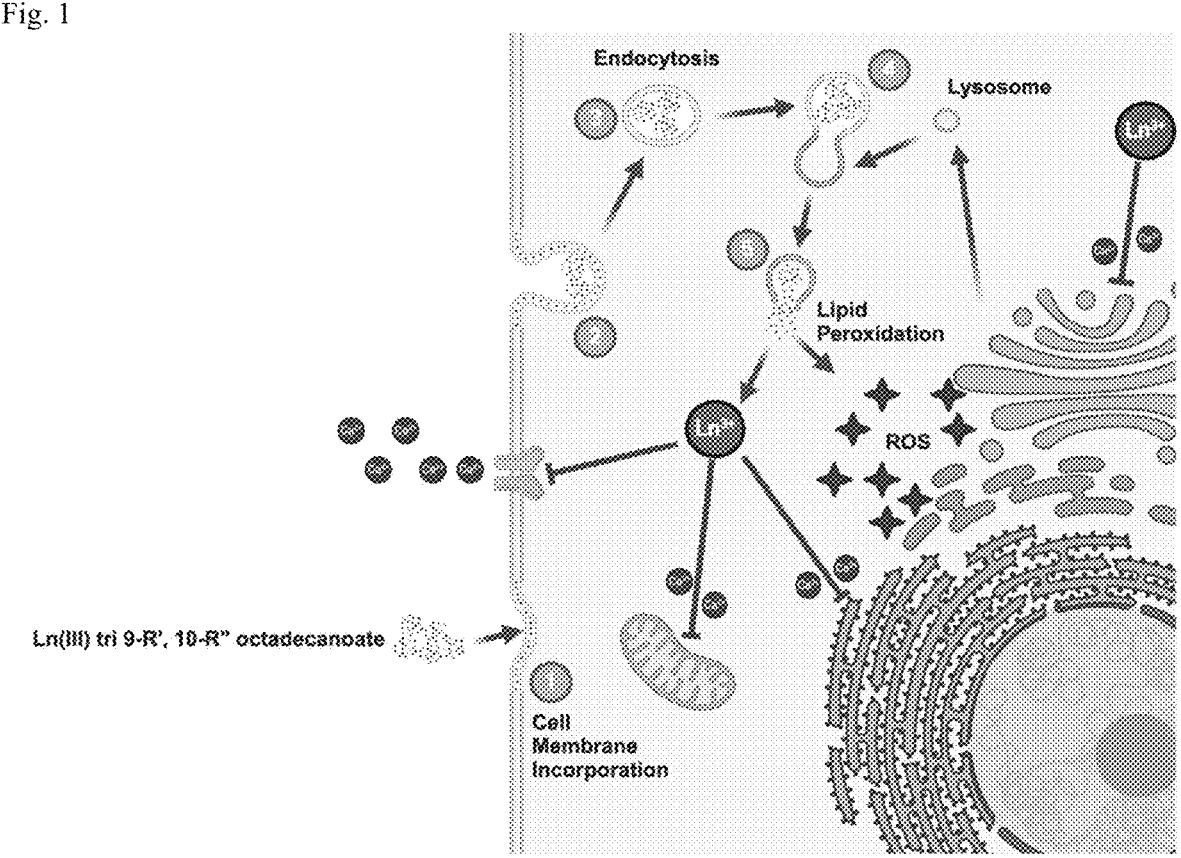

As used in this disclosure and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

The term "comprising" or "comprises" is intended to mean that the compositions and methods include the recited elements, but do not exclude others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other the ingredients and substantial method steps recited by the claims. Embodiments defined by each of these transition terms are within the scope of this invention.

As used here, the term "antagonist" is used interchangeably with "inhibitor" and refers to a substrate that blocks or suppresses the activity, function, effect, or expression of a target. In some embodiments, the target is a compound, a protein, a gene, a cell, or an agent. As used herein, the term "expression" refers to the amount a living cell produces of a target. In some embodiments, the inhibitor suppresses expression of a target gene or protein. In some embodiments, the inhibitor includes a compound that prevents binding of another molecule to an enzyme or molecular pump.

In some embodiments, the inhibitor is a compound that causes downregulation of the enzyme. In some embodiments, the inhibitor can be a competing or non-competing inhibitor.

The term "administering" as used herein includes prescribing for administration as well as actually administering, and includes physically administering by the subject being treated or by another.

The term "contacting" means direct or indirect binding or interaction between two or more. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration.

As used herein "subject," "patient," or "individual" refers to any subject, patient, or individual, and the terms are used interchangeably herein. In this regard, the terms "subject," "patient," and "individual" includes mammals, and, in particular humans. When used in conjunction with "in need thereof," the term "subject," "patient," or "individual" intends any subject, patient, or individual having or at risk for a specified symptom or disorder.

As used herein, the phrase "therapeutically effective" or "effective" in context of a "dose" or "amount" means a dose or amount that provides the specific pharmacological effect for which the compound or compounds are being administered. It is emphasized that a therapeutically effective amount will not always be effective in achieving the intended effect in a given subject, even though such dose is deemed to be a therapeutically effective amount by those of skill in the art. For convenience only, exemplary dosages are provided herein. Those skilled in the art can adjust such amounts in accordance with the methods disclosed herein to treat a specific subject suffering from a specified symptom or disorder. The therapeutically effective amount may vary based on the route of administration and dosage form.

The term "treating" or "treatment" covers the treatment of a cancer described herein, in a subject, such as a human, and includes (i) inhibiting a cancer, i.e., arresting its development; (ii) relieving a cancer or disorder, i.e., causing regression of the cancer; (iii) slowing progression of the cancer; and/or (iv) inhibiting, relieving, or slowing progression of one or more symptoms of the cancer. For example, treatment of a cancer includes, but is not limited to, elimination of the cancer or the condition caused by the cancer, remission of the tumor, inhibition of the cancer, or reduction or elimination of at least one symptom of the tumor.

The term "analog" refers to a compound in which one or more individual atoms or functional groups have been replaced, either with a different atom or a different functional group, generally giving rise to a compound with similar properties. In some aspect, the analog refers to a structure that is similar to another but differs in one or two components.

The term "derivative" refers to a compound that is formed from a similar beginning compound by attaching another molecule or atom to the beginning compound. Further, derivatives, according to the invention, encompass one or more compounds formed from a precursor compound through addition of one or more atoms or molecules or through combining two or more precursor compounds.

The disclosure relates to a controlled release formulation comprising a pharmaceutically acceptable carrier, a lanthanide (III) 9-R', 10-R" octadecanoate compound, and a targeted therapy.

The controlled release formulation may also include additional tarted therapy drugs. Preferably, one of the targeted therapy drugs is N-allyl noroxymorphone or a salt thereof.

The disclosure also relates to therapeutic methods of using formulations comprised of the lanthanide (III) 9-R', 10-R" octadecanoate compound to treat cancers.

Lanthanide Compounds

By "lanthanide compound" is meant any molecule that comprises lanthanum, cerium, praseodymium, neodymium, gadolinium, and terbium. Lanthanum, cerium, praseodymium, neodymium, gadolinium, and terbium are lanthanide metals. In the methods and compositions described herein, the lanthanide compounds described may be used to treat cancer.

In some embodiments, a lanthanide compound may be an inorganic lanthanide salt. In some embodiments, the lanthanide compound may include lanthanum (III) chloride, lanthanum (III) sulfate, lanthanum (III) nitrate, and lanthanum (III) acetate, which may optionally be present in an amount of 0.1% to 85% (w/w). In some embodiments, the lanthanide compound may include cerium (III) chloride, cerium (III) sulfate, cerium (III) nitrate, and cerium (III) acetate, which may optionally be present in an amount of 0.1% to 85% (w/w). In some embodiments, the lanthanide compound may include praseodymium (III) chloride, praseodymium (III) sulfate, praseodymium (III) nitrate, and praseodymium (III) acetate, which may optionally be present in an amount of 0.1% to 85% (w/w). In some embodiments, the lanthanide compound may include neodymium (III) chloride, neodymium (III) sulfate, neodymium (III) nitrate, and neodymium (III) acetate, which may optionally be present in an amount of 0.1% to 85% (w/w). In some embodiments, the lanthanide compound may include gadolinium (III) chloride, gadolinium (III) sulfate, gadolinium (III) nitrate, and gadolinium (III) acetate, which may optionally be present in an amount of 0.1% to 85% (w/w). In some embodiments, the lanthanide compound may include terbium (III) chloride, terbium (III) sulfate, terbium (III) nitrate, and terbium (III) acetate, which may optionally be present in an amount of 0.1% to 85% (w/w).

Biologic Activiy of Lanthanide Compounds

Lanthanide Modifications of Protein and Enzyme Activity:

Lanthanides:

Lanthanides with a 3+ valence (e.g., $Ln^{3+}$) encompasses, lanthanum (III) (e.g., $La^{3+}$), cerium (III) (e.g., $Ce^{3+}$), praseodymium (III) (e.g., $Pr^{3+}$), neodymium (III) (e.g., $Nd^{3+}$), gadolinium (III) (e.g., $Gd^{3+}$), and terbium (III) (e.g., $Tb^{3+}$). Biologic activities in which the lanthanides can substitute for calcium ($Ca^{2+}$) ions, magnesium ($Mg^{2+}$) ions, and manganese ($Mn^{2+}$) ions includes $La^{3+}$, $Ce^{3+}$, $Pr^{3+}$, $Nd^{3+}$, $Gd^{3+}$, and $Tb^{3+}$. Biologically, lanthanide substitutions for $Ca^{2+}$ have been found to result in the same biologic effect.

Calmodulin (CaM):

CaM is a ubiquitous $Ca^{2+}$-binding protein which mediates intracellular responses to $Ca^{2+}$ fluxes. It does this by interacting with specific receptor proteins in a $Ca^{2+}$-dependent manner. It is a highly acidic protein of pH 4. It is a dumbbell-shaped molecule, with two globular lobes connected by a long, exposed alpha-helix. Each lobe binds two $Ca^{2+}$ ions through the helix-loop-helix structure that is typical of "E-F" handed proteins. Upon binding $Ca^{2+}$, the protein undergoes marked conformational changes, exposing a hydrophobic domain. $Ln^{3+}$ can substitute for $Ca^{2+}$ in the $Ca^{2+}$-dependent attachment of CaM to cell membranes. At sub-optimal concentrations, $Ca^{2+}$ and $Ln^{3+}$ have an additive effect. However, nanomolar concentrations of $Ln^{3+}$ inhibit the CaM-regulated guanylate cyclase by dissociating CaM from the enzyme. High concentrations of $Ln^{3+}$ usually inhibit CaM-mediated processes. Indeed, treatment with millimolar concentrations of $Ln^{3+}$ is one technique used to dissociate CaM from enzymes and membranes.

$Ca^{2+}/Mg^{2+}$-ATPase:

Cells need to regulate very closely their cytosolic $Ca^{2+}$ concentrations, usually maintaining them at sub-micromolar levels. This is achieved despite the presence of an extracellular milieu where the $Ca^{2+}$ concentration is often in the millimolar range. Such regulation is aided by specialized $Ca^{2+}$ "pumps" which harness the energy released by hydrolysis of the terminal phosphodiester bond of ATP to transport $Ca^{2+}$ across cellular membranes. These enzymes hence show ATPase activity; as they require both $Ca^{2+}$ and $Mg^{2+}$, they are referred to as $Ca^{2+}/Mg^{2+}$-ATPases. Such enzymes are associated with cell membranes and may transport $Ca^{2+}$ across the limiting membranes of intracellular organelles, such as mitochondria and the endoplasmic reticulum, or across the plasma membrane, thus ejecting $Ca^{2+}$ from the cell altogether. There also exist $Mg^{2+}$-ATPases, which do not require $Ca^{2+}$, and $Na^+/K^+$-ATPases, which transport monovalent cations.

Many of the physiological effects of lanthanides reflect their influence on cellular calcium homeostasis. The best studied example is the $Ca^{2+}/Mg^{2+}$-ATPase of the sarcoplasmic reticulum (SR), an intracellular, membranous organelle of skeletal muscle cells, corresponding to the endoplasmic reticulum (ER) of non-muscle cells. During muscle contraction, the sarcoplasmic reticulum releases $Ca^{2+}$ which triggers the interaction between the thick and thin myofilaments.

During muscle relaxation, $Ca^{2+}$ is transported, against a $Ca^{2+}$ gradient, across the sarcoplasmic reticulum. It is this second step which is the energy-dependent process catalyzed by $Ca^{2+}/Mg^{2+}$-ATPase. Two moles of $Ca^2$ are transported per mole of ATP hydrolyzed. $Ln^{3+}$ has been shown to inhibit the $Mg^{2+}$-ATPase and $Na^+/K^+$-ATPase in rat heart sarcolemma and erythrocytes. It is possible to suppress completely $Ca^{2+}$ efflux from erythrocytes at $Ln^{3+}$ concentrations where the total ATPase is only reduced by 50%.

Kinases:

Phosphoglycerate kinase catalyzes the reversible phosphorylation of 3-phosphoglycerate by ATP. The lanthanides (Ln) inhibit the forward reaction by forming La-ATP-complex, which competes with Mg-ATP as substrates for the reaction. The K-values for La-ATP is about 0.04-mM, compared with a K-value of 0.073-mM for Mg-ATP. No conformational change in the Ln-ATP complex upon binding to the enzyme has been detected. Ln-ATP complexes also inhibit hexokinase, the enzyme which catalyzes the reversible phosphorylation of glucose. Inhibition is competitive with respect to Mg-ATP. When free $Mg^{2+}$ is added, enzymic activity reappeared due to the competitive displacement of $Ln^{3+}$ ions from ATP. Pyruvate kinase reversibly catalyzes the phosphorylation of ADP via phosphoenolpyruvate. It is strongly inhibited by the lanthanides. This enzyme requires $Mn^{2+}$ or $Mg^{2+}$ for activity. Competition experiments showed that $Mn^{2+}$, $Mg^{2+}$, $Ca^{2+}$, and $Ln^{3+}$ can bind to pyruvate kinase. The K-value for the interaction of La-ATP with pyruvate kinase was estimated as 13-µM. $Ln^{3+}$ may inhibit enzymic activity by blocking a conformational change induced by the binding of a substrate. Myosin light chain kinase is regulated by $Ca^{2+}$-calmodulin. At a concentration of 100-µM, $Ln^{3+}$ is able to support over 60% of the enzymatic activity produced by the same concentration of $Ca^{2+}$. Protein kinase C requires both phospholipid and $Ca^{2+}$. $Ln^{3+}$ at 10- to 300-µM concentrations can replace $Ca^{2+}$ in supporting protein kinase C activity. $La^{3+}$ at concentrations of 100-µM have been shown to slightly inhibited cGMP and cAMP dependent protein kinases.

Alkaline Phosphatase:

The alkaline phosphatase contains four $Zn^{2+}$ ions and requires the binding of one $Mg^{2+}$ to become enzymatically active. $Ln^{3+}$ can occupy the $Mg^{2+}$ site, with $K_d$ of 0.16-µM, which results in protein conformational changes that would effect enzyme activity.

Transient Receptor Potential (TRP) Channel Receptors:

Some transient receptor potential (TRP) channels have been shown to be permeable to trace metal ions, and it has been demonstrated in some cases that TRP channels are important for the physiological uptake of trace metal ions. In mammals, the TRP superfamily is subdivided into six families named TRPA, TRPC, TRPM, TRPML, TRPP and TRPV, each family comprising up to eight members. TRP channels conduct $Ca^{2+}$, with most of them are located in the plasma membrane, but some are found both in the plasma membrane and in intracellular membranes (e.g. TRPM1, TRPM2, TRPM7, TRPM8, TRPC3, TRPV1 and TRPV4) and still others are exclusively found on intracellular membranes (e.g. TRPML channels).

The lanthanides have been used to inhibit most mammalian TRP channels. The lanthanides also potentiate signaling is a smaller number of TRP channels that include TRPC1, TRPC4, and TRPC5 channels. This stimulating effect is seen for concentrations of $Ln^{3+}$ ranging from 1- to 1,000-µM. At still higher concentrations (5-mM), $Ln^{3+}$ blocks TRPC5 current. Extracellular $Ca^{2+}$ ions are also capable of stimulating TRPC5 channels (concentration range 2- to 20-mM). At 20-mM extracellular $Ca^{2+}$, $Ln^{3+}$ ions were found not to have an additional potentiating effect, indicating that $Ca^{2+}$ competes with $Ln^{3+}$ for the same binding site. Two negatively charged glutamate residues (Glu543 and Glu595), close to the extracellular mouth of the pore, are controlling the positive regulatory processes. The same amino acids are also important for the activation of TRPC5 channels by $Ca^{2+}$ ions.

TRPV1 proteins also are activated by the lanthanides. The application of $Ln^{3+}$ at concentrations of 10- to 1,000-µM elicits currents, indicating direct activation of TRPV1 channels. In addition, at concentrations lower than 100-µM, $Ln^{3+}$ potentiates TRPV1 activity induced by heat, acid, and capsaicin. The $Ln^{3+}$-dependent potentiation seems to involve two glutamate residues at position 600 and 648 of the TRPV1. Human TRPV6 channels are modulated by low concentrations of extracellular $Ln^{3+}$, which increases $Ca^{2+}$ currents slightly (<50%); whereas at higher concentrations, $Ln^{3+}$ depress hTRPV6-dependent $Ca^{2+}$ currents. TRPV5 channels are highly sensitive to lanthanum and are inhibited by $Ln^{3+}$ with an $IC_{50}$ of 4.6-µM.

TRPA1 channels are inhibited by $Ln^{3+}$, with an $IC_{50}$ value that strongly depends on the concentration of extracellular $Ca^{2+}$. At approximately physiological $Ca^{2+}$ concentrations (2-mM), the $IC_{50}$ values are 300-µM for $Ln^{3+}$. At 20-µM $Ca^{2+}$, however, the lanthanum is much more potent, with an $IC_{50}$ of 54-µM.

TRPML1 channels are inhibited by 100-µM of $Ln^{3+}$ while TRPML3 channels are much more sensitive with an $IC_{50}$ of 15-µM. Several studies found that TRPM4 channels are inhibited by $Ln^{3+}$. Approximately 50% inhibition by 30-µM $Ln^{3+}$ was proposed when these channels were activated by mechanical stretch. The situation is similar for TRPM5, which was inhibited by 100-µM $Ln^{3+}$. TRPM7 channels were found to be insensitive to low concentrations of $Ln^{3+}$, but 10-mM blocked inward and outward currents completely. $Ln^{3+}$ ions at 2- and 10-mM were found to block inward currents through TRPM7 completely, while outward currents were only partially inhibited even at these very high concentrations.

Figures 2A, 2B:
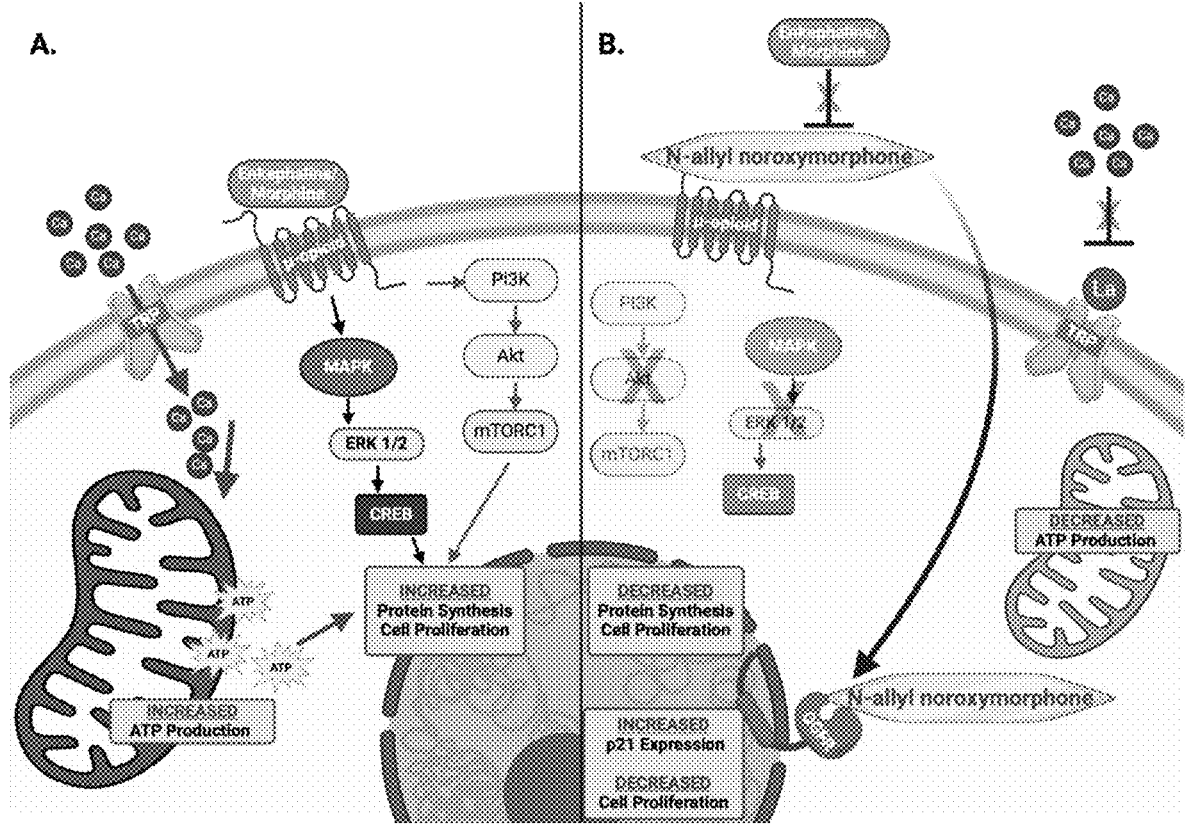

TRP channels and the p-opioid receptor collaborate to drive cell division (FIG. 2). TRP receptors also mediate cellular functions that include the regulation of intracellular signaling proteins (e.g., calmodulin) and mitochondria. The p-opioid-receptor (MOR) mediates cellular function through activation of MAPK or PI3K signaling (FIG. 2). Protein synthesis and cell proliferation are increased after opioid receptor binding of an opioid drug (e.g., morphine) or one of the native enkephalin proteins (e.g., met-5 enkephalin). Lanthanides can substitute for calcium to block calcium channels. Calcium is required for cell proliferation via the increased need for ATP or through calmodulin-dependent mechanisms. Loss of calcium influx via lanthanum can result in decreased mitochondrial ATP production and decreased cell proliferation.

Lanthanide Effects of Nucleic Acids:

The affinities of the lanthanides for polynucleotides exceed their affinities for individual nucleotides, with tRNA providing stronger ligands than DNA. Urea increases lanthanides binding to poly(G) by preventing the formation of four-stranded helices. This is consistent with the general observation that the greater the degree of secondary structure in a nucleic acid or polynucleotide, the lower is its ability to bind lanthanum. Further, the affinity of the double stranded forms exceeds that of the single stranded forms, which suggests a preferential binding of $Ln^{3+}$, at low concentration, to the double stranded G-C regions. Further, thermally denaturing DNA increases $Ln^{3+}$ binding and specifically increases Terbium (Tb) luminescence. This latter property of Terbium can be used to monitor rates of DNA reannealing, to detect subtle changes in conformation that lead to local melting of the helix, and to detect single stranded DNA bands on gels after electrophoresis. Supporting evidence comes from the observation that treatment of commercial DNA preparations with nucleases greatly reduces their ability to enhance $Tb^{3+}$ luminescence. Titration studies suggest that all lanthanides bind the DNA phosphates moieties.

Lanthanide Activity in Mitochondria:

The lanthanides inhibits both energy-dependent transport and energy-independent binding of $Ca^{2+}$ by mitochondria. In so doing, lanthanum inhibits $Ca^{2+}$-dependent activation of respiration, oxidation of cytochromes, increases in intra mitochondrial pH, swelling, and increases in acetyl-coenzyme A permeability, without affecting oxidative phosphorylation or monovalent cation accumulation. $Ca^{2+}$-dependent oxygen consumption is strongly inhibited by the addition of 3.1-µM $La^{3+}$. $Ln^{3+}$ transport has also been invoked to explain the enhanced efflux of $Ca^{2+}$ from the mitochondrion in response to the addition of $Ln^{3+}$ ions. The $Ca^{2+}$ transporter has several $Ca^{2+}$-binding sites; however, the binding of $Ln^{3+}$ to only one of these sites inhibits $Ca^{2+}$ transport. High-affinity binding sites may be the $Ca^{2+}$ transporter of the inner mitochondrial membrane, which has a Ka for $Ln^{3+}$ of 0.83-µM. The slow decay of observed in luminescence studies occurred by transfer of energy to suitable chromophores, probably the heme groups of the cytochrome proteins. All the cytochromes, apart from cytochrome C, are buried in the membrane of mitochondria core, 20- to 50-A from the surface. Measurements have suggested a positive µM local surface potential in intact mitochondria but a negative potential in sub-mitochondrial particles. This was interpreted as reflecting two different types of binding sites, possibly the matrix and cytoplasmic sides of the $Ca^{2+}$ transporter. $Ln^{3+}$ ions produced a 50% inhibition at 0.2-nmol/mg for the $Ca^{2+}$ transporter.

Lanthanides Activity in Endoplasmic Reticulum:

Millimolar concentrations of $Ln^{3+}$ are inhibitory in the endoplasmic reticulum (ER). $Ln^{3+}$ also binds to the low-affinity $Ca^{2+}$ sites with a Ka value of 6.5-µM, whereas the Ka, for $Ca^{2+}$ is 32-µM. Binding of $Ln^{3+}$ to the ER is greater in the presence of adenosine triphosphate (ATP). The ability of $Ln^{3+}$ ions to compete for $Ca^{2+}$ on the ER is reflected in the high concentrations that need to be added before inhibition of $Ca^{2+}$ uptake is observed in the ER. At such concentrations, microsomal $Ca^{2+}$-ATPase is also inhibited. Inhibition of $Ca^{2+}$ uptake has been reported to be non-competitive, with 50% of the inhibition occurring with 125-µM $Ln^{3+}$. In addition to using the $Ca^{2+}$-ATPase-driven reaction, microsomes can accumulate $Ca^{2+}$ via the Na—$Ca^{2+}$ ion exchanger.

Cancer

In some embodiments, the controlled release formulation may be used for treating a cancer.

Cancer may refer to a condition in which abnormal cells divide without control and can invade nearby tissues.

In some embodiments, the cancer may be a carcinoma, i.e., a cancer that arises from tissue that functions to line, cover, or act as a barrier for internal organs, such as the skin or breast epithelium. In some embodiments, the cancer may be sarcoma, i.e., a connective tissue cancer that can begin in bone, cartilage, fat, muscle, or other connective or supportive tissue. In some embodiments, the cancer may be a hematological cancer, i.e., a blood cancer that starts in or includes blood-forming tissue, such as the bone marrow, and causes large numbers of abnormal blood cells to be produced and enter the blood. In some embodiments, the cancer is a lymphoma or multiple myeloma, i.e., a cancer that derives from the cells of the immune system. In some embodiments, the cancer may be a central nervous system cancer, i.e., a cancer that is derived or begins in a tissue of the brain and/or spinal cord.

In some embodiments, the cancer is one or more of pancreatic cancer, renal cancer, small cell lung cancer, brain cancer, neural cancer, bone cancer, lymphoma, myeloma, gastrointestinal tract cancer, uterine cancer, leukemia, liver cancer, prostate cancer, skin cancer, and melanoma. In some embodiments, the cancer is soft tissue non-osteogenic sarcomas, chondrosarcoma, fibrosarcoma, or synovial sarcoma. In some embodiments, the cancer is specifically, a basal cell carcinoma, melanoma, bladder carcinoma, non-small cell lung carcinoma, small cell lung carcinoma, or prostate carcinoma. In some embodiments, the cancer is specifically a cancer derived from neuroectoderm or is a brain cancer such as thyroid adenocarcinomas, glioblastoma, pituitary tumors, oligodendrocytoma, gangliogliomas, hemangioblastomas, medulloblastomas, meningiomas, rhabdoid tumors, schwannomas, acoustic neuroma, craniopharyngioma, chordoma, CNS lymphoma, optic nerve glioma, sub ependymoma, neuroblastoma, or astrocytoma.

In some embodiments, the cancer is a sarcoma of bone, in the appendicular skeleton, the axial skeleton, and the skull, which includes non-specific bone sarcomas, osteosarcoma, osteogenic sarcomas, Ewing's sarcoma of bone, or benign bone tumors.

In some embodiments, the cancer may be a breast cancer. In some more particular embodiments, the breast cancer is a sub-type in which any of the following characteristics are used to identify the breast cancer phenotype. For instance, the breast cancer can be hormone receptor positive, or the breast cancer may be hormone receptor negative, or the breast cancer can be human epidermal growth factor receptor-2 positive, or the breast cancer human epidermal growth factor receptor-2 negative. In some embodiments, the breast cancer can be hormone receptor positive and is only estrogen receptor positive, or the breast cancer can be hormone receptor positive and is only progesterone receptor positive, or the breast cancer can be hormone receptor positive and express both estrogen receptor positive and progesterone receptor positive. In some embodiments, the breast cancer is triple negative breast cancer (TNBC) in which the cancer does not express the estrogen receptor, the progesterone receptor, or the human epidermal growth factor receptor-2. In some embodiments, the breast cancer phenotype is used to determine therapeutic interventions.

In some embodiments, the cancer results in metastases, which are tumors derived from a parent cancer that spreads to other parts of the body. Metastatic tumors can be in the liver, lymph nodes, brain, lung, bone, appendicular skeletal bones (e.g., femur, tibia, radius, ulna, and humerus), axial skeletal bones (e.g., spine and pelvis), and the cranial bones (e.g., cranium, mandible, and maxilla).

In some embodiments, a composition comprising a lanthanide (III) 9-R', 10-R" octadecanoate compound may be administered locally to a site of a cancerous lesion (e.g., intratumorally, peritumorally or perilesionally), which may be, for example, a site of a primary or metastatic cancer lesion.

In some embodiments, a composition comprising a lanthanide (III) 9-R', 10-R" octadecanoate compound may be contacted in vivo or in vitro with a cancer cell.

In some embodiments, a composition comprising a lanthanide (III) 9-R', 10-R" octadecanoate compound may be administered systemically, delivered via normal systemic administration routes, to treat a cancerous lesion, for example a primary or metastatic lesion.

Normal routes of systemic administration include oral, intravenous, intraperitoneal, subdural, or intramuscular.

Anti-Cancer and Anti-Neoplastic Drugs Opioid Growth Factor Receptor (Ogfr) Antagonists By "Opioid Growth Factor Receptor (OGFR) antagonist" describes any molecule that inhibits, suppresses or causes the cessation of at least one OGFR-mediated biological activity such as naloxone or a functional derivative thereof.

In some embodiments, an OGFR antagonist is included in the compositions and therapeutic methods described herein.

In some embodiments, an OGFR antagonist may be an OGFR binding antagonist, namely, a molecule that, interferes with, blocks or otherwise prevents the interaction or binding of the met5-ligand (OGF) to the OGFR. Met-5 is derived from the pro-hormone pro-enkephalin (PENK).

An OGFR binding antagonist may compete with the met5-ligand for binding to the OGFR on the surface of the nuclear membrane, thereby interfering with, blocking or otherwise preventing the binding of the met5-ligand to the OGFR, without triggering the downstream signaling that would otherwise be induced by the binding of the met5-ligand to the OGFR. Alternatively, an OGFR binding antagonist may bind to or sequester pro-enkephalin (PENK) or the met5-ligand with sufficient affinity and specificity to substantially interfere with, block or otherwise prevent binding of met5-ligand to the OGFR, thereby inhibiting, suppressing or causing the cessation of at least one OGFR-mediated biological activity. Generally, OGFR binding antagonists may be large molecules (e.g., antibodies) or small molecules (e.g., compounds of a molecular weight of less than 15-kD, 12-kD, 10-kD or even 8-kD), and may be a polypeptide, nucleic acid, or a synthetic small molecule compound. OGFR binding antagonists may be identified with any in vitro assay readily selected by one of skill in the art. For example, OGFR antagonists may be identified using the methods described in Zagon et al., Brain Research Reviews, 2002, 38(3):351-76. Other suitable OGFR antagonists are disclosed in PCT patent application publications Nos. WO2021/011529; WO2022/015364; U.S. patent application publications Nos. 2019-0093109; 2021-0030746; 2021-0228571; 2022-0016312; and U.S. Pat. No. 11,471,454.

In one embodiment, the OGFR binding antagonist may be N-allyl noroxymorphone or a functional derivative thereof, naltrexone or a functional derivative thereof, or a combination thereof.

As used herein, a "functional derivative" refers to a derivative or analog that is structurally and functionally analogous to the originating molecule (e.g., maintains the function of naltrexone or naloxone as an OGFR antagonist). N-allyl noroxymorphone and naltrexone analogs can be synthesized using standard synthetic procedures such as those described in March J., Advanced Organic Chemistry, 3rd Ed. (1985). Examples of naltrexone and N-allyl noroxymorphone functional derivatives include salt forms, e.g., N-allyl noroxymorphone hydrochloride dihydrate or naltrexone hydrochloride. Additional examples of naltrexone and N-allyl noroxymorphone functional derivatives suitable for use in the present methods include naltrexone and N-allyl noroxymorphone analogs disclosed in U.S. Patent Application Publication No. 2007/0197573 A1, U.S. Pat. No. 6,713,488, for example.

In another embodiment, an OGFR binding antagonist may be derived from oxymorphone and binds to the OGFR, which includes N-allyl noroxymorphone, naltrexone, nalorphine, naloxonazine, levallorphan, nalmefene, cyprodime, cyclorphan, cyclazocine, oxilorphan, LY113878, MR2266, diprenorphine, WIN 44,441-3, naltindole, or norbinaltorphimine.

In one embodiment, the OGFR binding antagonist may be N-allyl noroxymorphone.

In still another embodiment, an OGFR binding antagonist may be derived from trans-3,4-dimethyl-4-phenylpiperidine and binds to the OGFR, which includes LY99335, LY25506, LY117413, or LY255582.

In another embodiment, an OGFR binding antagonist is derived from the met5-enkephalin or leu-enkephalin peptides, binds to the OGFR, and minimally includes the following amino acid sequences as a means of targeting the OGFR: Tyr-Gly-Gly-Phe-µMet (SEQ ID NO: 1) for those derived from met5-enkephalin or Tyr-Gly-Gly-Phe-Leu (SEQ ID NO: 2) for those derived from the leu-enkephalin.

In still another embodiment, an OGFR binding antagonist is derived from the peptide antagonist 101174864 (N,N-diallyl-Tyr-Aib-Aib-Phe-Leu-OH; Aib-aminoisobutyric acid) or somatostatin analog CTP(D-Phe-Cys-Tyr-D-Trp-Lys-Thr-Pen-Thr-NH.sub.2, SEQ ID NO: 3).

In other embodiments, the OGFR antagonist, instead of being an OGFR binding antagonist, is a molecule that disrupts the nuclear localization sequence found within OGFR: 251 QSALDYFMFAVR-CRHQRRQLVHFAWEHFR-PRCKFVWGPQDKLRRFKPSSL (SEQ ID NO: 4).

In still other embodiments, the OGFR antagonist employed in the present methods is a small-hairpin RNA (shRNA) or a small-interfering RNA (siRNA) directed against the OGFR gene and effective in disrupting OGFR gene expression.

The OGFR antagonists described herein may be administered individually or in combination. Suitable combinations include, for example, naloxone and naltrexone; naloxone and/or naltrexone, in combination with another OGFR binding antagonist or another OGFR antagonist.

In some embodiments, the OGFR inhibitor is an antineoplastic therapy and an anti-cancer therapy that be used to treat a cancer, or cancer tumor, or metastases from a cancer in any of the tissues in which a metastatic tumor can spread. In another embodiment, the OGFR inhibitor used to treat a cancer, or a neoplasm is N-allyl noroxymorphone or naltrexone, or a salt thereof. In a preferred embodiment, the OGFR inhibitor is N-allyl noroxymorphone, a salt thereof, including N-allyl noroxymorphone hydrochloride, N-allyl noroxymorphone hydrochloride anhydride, and N-allyl noroxymorphone hydrochloride dihydrate.

Targeted Cancer Therapies

The present disclosure contemplates the use of the lanthanum compounds described herein in combination with one or more additional therapies useful in the treatment of cancer.

In some embodiments, one or more of the additional therapies is a therapeutic agent. Exemplary therapeutic agents include chemotherapeutic agents, radiopharmaceuticals, hormone therapies, CDK inhibitors (including CDK4/6 inhibitors such as palbociclib, ribociclib, and abemaciclib), epigenetic modulators, selective estrogen receptor modulators (SERM), selective estrogen receptor degraders (SERD), aromatase inhibitors (AI), phosphatidyl inositol-3-posphate kinase (PI3K) inhibitors, ATP-adenosine axis-targeting agents, targeted therapies, signal transduction inhibitors, RAS signaling inhibitors, PI3K inhibitors, arginase inhibitors, HIF inhibitors, AXL inhibitors, PAK4 inhibitors, immunotherapeutic agents, cellular therapies, gene therapies, immune checkpoint inhibitors, and agonists of stimulatory or co-stimulatory immune checkpoints.

In some embodiments, the additional anti-cancer therapeutic agent is a chemotherapeutic agent. Examples of chemotherapeutic agents include, but are not limited to: alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, pomalidomide, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pemetrexed, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab paclitaxel, and docetaxel; chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; proteasome inhibitors such as bortezomib, carfilzomib and ixazomib; topoisomerase inhibitors such as irinotecan, topotecan, etoposide, mitoxantrone, teniposide; difluoromethylornithine (DMFO); retinoic acid; esperamicins; capecitabine; anthracyclines and pharmaceutically acceptable salts, acids or derivatives of any of the above.

In some embodiments, the additional anti-cancer therapeutic agent is a hormone therapy. Hormone therapies act to regulate or inhibit hormonal action on tumors. Examples of hormone therapies include, but are not limited to: selective estrogen receptor degraders such asfulvestrant, giredestrant, SAR439859, RG6171, AZD9833, rintodestrant, ZN-c5, LSZ102, D-0502, LY3484356, SHR9549; selective estrogen receptor modulators such as tamoxifen, raloxifene, 4-hydroxytamoxifen, trioxifene, keoxifene, toremifene; aromatase inhibitors such asanastrozole, exemestane, letrozole and other aromatase inhibiting 4(5)-imidazoles; gonadotropin-releasing hormone agonists such as nafarelin, triptorelin, goserelin; gonadotropin-releasing hormone antagonists such as degarelix; antiandrogens such as abiraterone, enzalutamide, apalutamide, darolutamide, flutamide, nilutamide, bicalutamide, leuprolide; 5α-reductase inhibitors such as finasteride, dutasteride; and the like.

In some embodiments, the additional anti-cancer therapeutic agent is a cyclin-dependent kinase (CDK) inhibitor. Examples of CDK inhibitors include but are not limited to: flavopiridol, roscovitine, RO-3306, dinaciclib, milciclib, palbociclib, ribociclib, abemaciclib, BS-181, DRB, meriolin 3, variolin B, meridianin E, nortopsentins, AZD5438, roniciclib, SNS-032, H-Ala-Ala-Abu-Arg-Arg-Leu-Ile-pFPhe-NH2 (SEQ ID NO: 5), H-His-Ala-Lys-Arg-Arg-Leu-Ile-Phe-NH2 (SEQ ID NO: 6), MM-D37K, sorafenib, K03861, PD184352 (CI-1040), 8-anilino-1-naphthalene sulfonate (ANS), THZ531, THZ1, SY-1365, and E9.

Controlled Release of Anti-Neoplastic and Anti-Cancer Therapies

According to one embodiment, described herein is a composition comprising a lanthanide (III) 9-R', 10-R" octadecanoate compound, excipients to stabilize the controlled release formulation, excipients to solubilize the therapeutic components of the controlled release formulation, excipients to form an emulsion of the controlled release formulation, and a liquid delivery vehicle. In some embodiments, the composition may be used for therapeutic methods. In some embodiments, the composition comprising a lanthanide (III) 9-R', 10-R" octadecanoate compound is a controlled release formulation.

In some embodiments, the controlled release formulation may include between 1-nM to 10-μM of the lanthanide (III) 9-R', 10-R" octadecanoate compound. In some embodiments, the lanthanide (III) 9-R', 10-R" octadecanoate compound is a lanthanide ester, or a functional derivative thereof. In other embodiments, the controlled release formulation may include any one of the following concentrations of lanthanide (III) 9-R', 10-R" octadecanoate in the following list of concentrations (list 1): 0.1-ng/mL, 0.25-ng/mL, 0.5-ng/mL, 1-ng/mL, 2.5-ng/mL, 5-ng/mL, 10-ng/mL, 15-ng/mL, 20-ng/mL, 25-ng/mL, 30-ng/mL, 35-ng/mL, 40-ng/mL, 45-ng/mL, 50-ng/mL, 55-ng/mL, 60-ng/mL, 65-ng/mL, 70-ng/mL, 75-ng/mL, 80-ng/mL, 85-ng/mL, 90-ng/mL, 95-ng/mL, or 100-ng/mL. In yet other embodiments, the controlled release formulation may include any one of the following concentrations of lanthanide (III) 9-R', 10-R" octadecanoate in the following list of concentrations (list 2): 100-ng/mL, 200-ng/mL, 300-ng/mL, 400-ng/mL, 500-ng/mL, 600-ng/mL, 700-ng/mL, 800-ng/mL, 900-ng/mL, or 1000-ng/mL. In yet other embodiments, the controlled release formulation may include any one of the following concentrations of lanthanide (III) 9-R', 10-R" octadecanoate in the following list of concentrations (list 3):1-μg/mL, 2-μg/mL, 3-μg/mL, 4-μg/mL, 5-μg/mL, 6-μg/mL, 7-μg/mL, 8-μg/mL, 9-μg/mL, 10-μg/mL, 11-μg/mL, 12-μg/mL, 13-μg/mL, 14-μg/mL, 15-μg/mL, 16-μg/mL, 17-μg/mL, 18-μg/mL, 19-μg/mL, 20-μg/mL, 30-μg/mL, 40-μg/mL, 50-μg/mL, 60-μg/mL, 70-μg/mL, 80-μg/mL, 90-μg/mL, or 100-μg/mL. In yet other embodiments, the controlled release formulation may include any one of the following concentrations of lanthanide (III) 9-R', 10-R" octadecanoate in the following list of concentrations (list 4): 100-μg/mL, 200-μg/mL, 300-μg/mL, 400-μg/mL, 500-μg/mL, 600-μg/mL, 700-μg/mL, 800-μg/mL, 900-μg/mL, or 1000-μg/mL. In yet other embodiments, the controlled release formulation may include any one of the following concentrations of lanthanide (III) 9-R', 10-R" octadecanoate in the following list of concentrations (list 5): 1-mg/mL, 2-mg/mL, 3-mg/mL, 4-mg/mL, 5-mg/mL, 6-mg/mL, 7-mg/mL, 8-mg/mL, 9-mg/mL, 10-mg/mL, 11-mg/mL, 12-mg/mL, 13-mg/mL, 14-mg/mL, 15-mg/mL, 16-mg/mL, 17-mg/mL, 18-mg/mL, 19-mg/mL, 20-mg/mL, 21-mg/mL, 22-mg/mL, 23-mg/mL, 24-mg/mL, 25-mg/mL, 26-mg/mL, 27-mg/mL, 28-mg/mL, 29-mg/mL, 30-mg/mL, 31-mg/mL, 32-mg/mL, 33-mg/mL, 34-mg/mL, 35-mg/mL, 36-mg/mL, 37-mg/mL, 38-mg/mL, 39-mg/mL, 40-mg/mL, 41-mg/mL, 42-mg/mL, 43-mg/mL, 44-mg/mL, 45-mg/mL, 46-mg/mL, 47-mg/mL, 48-mg/mL, 49-mg/mL, or 50-mg/mL. In yet other embodiments, the controlled release formulation may include any one of the following concentrations of lanthanide (III) 9-R', 10-R" octadecanoate in the following list of concentrations (list 6): 100-mg/mL, 200-mg/mL, 300-mg/mL, 400-mg/mL, 500-mg/mL, 600-mg/mL, 700-mg/mL, 800-mg/mL, 900-mg/mL, 1000-mg/mL. In another embodiment, the controlled release formulation may include any one of the concentrations of lanthanide (III) 9-R', 10-R" octadecanoate may be added together in any combination chosen from list 1, list 2, list 3, list 4, list 5, or list 6 such that 0.25-ng/mL from list 1 is added to 100-ng/mL (list 2), 13-μg/mL (list 3), 700-μg/mL (list 4), 19-mg/mL (list 5), and 100-mg/mL (list); which results in the sum of 119,713, 100.25-ng/mL or 119.71310025-mg/mL.

In some embodiments, the lanthanide (III) 9-R', 10-R" octadecanoate compound may be at least 1% (w/w), or at least 2% (w/w), or at least 5% (w/w), or at least 10% (w/w), or at least 15% (w/w), or at least 20% (w/w), or at least 25% (w/w), or at least 30% (w/w), or at least 35% (w/w), or at least 40% (w/w), or at least 45% (w/w), or at least 50% (w/w), or at least 55% (w/w), or at least 60% (w/w), or at least 65% (w/w), or at least 70% (w/w), or at least 80% (w/w), or at least 90% (w/w), or at least 95% (w/w) of the controlled release formulation.

In methods comprising an OGFR antagonist, in some embodiments, when the OGFR antagonist is N-allyl noroxymorphone, naltrexone or their combination, a concentration of the OGFR antagonist administered to the subject or contacted to the cell may be at least 0.2-mg/ml, or at least 0.4-mg/ml, or at least 0.8-mg/ml, or at least 1.2-mg/ml, or at least 1.6-mg/ml, or at least 2.0-mg/ml, or at least 2.4-mg/ml, or at least 2.8-mg/ml, or at least 3.2-mg/ml, or at least 3.6-mg/ml, or at least 4.0-mg/ml, or at least 4.4-mg/ml, or at least 4.8-mg/ml, or at least 5.2-mg/ml, or at least 5.6-mg/ml, or at least 6.0-mg/ml, or at least 6.4-mg/ml, or at least 6.8-mg/ml, or at least 7.2-mg/ml, or at least 7.6-mg/ml, or at least 8.0-mg/ml, or at least 8.4-mg/ml, or at least 8.8-mg/ml, or at least 9.2-mg/ml.

In some embodiments, the controlled release formulation may further include at least 0.5-mM, or at least 1-mM, or at least 2-mM, or at least 3-mM, or at least 4-mM, or at least 5-mM, or at least 6-mM, or at least 7-mM, or at least 8-mM, or at least 9-mM, or at least 10-mM, or at least 11-mM, or at least 12-mM, or at least 13-mM, or at least 14-mM, or at least 15-mM, or at least 16-mM, or at least 17-mM, or at least 18-mM, or at least 19-mM, or at least 20-mM, or at least 21-mM, or at least 22-mM, or at least 23-mM of the OGFR antagonist.

In methods comprising an CDK4/6 antagonist, in some embodiments, when the CDK4/6 antagonist is abemaciclib, dinaciclib, milciclib, palbociclib, or ribociclib or their combination, a concentration of the CDK4/6 antagonist administered to the subject or contacted to the cell may be at least 0.1-nM, or at least 0.5-nM, or at least 1-nM, or at least 5-nM, or at least 10-nM, or at least 25-nM, or at least 50-nM, or at least 1-µg/mL, or at least 5-µg/mL, or at least 10-µg/mL, or at least 20-µg/mL, or at least 25-µg/mL, or at least 50-µg/mL, or at least 60-µg/mL, or at least 70-µg/mL, or at least 80-µg/mL, or at least 90-µg/mL, or at least 0.5-mM, or at least 1-mM, or at least 2-mM, or at least 3-mM, or at least 4-mM, or at least 5-mM, or at least 6-mM, or at least 7-mM, or at least 8-mM, or at least 9-mM, or at least 10-mM, or at least 11-mM, or at least 12-mM, or at least 13-mM, or at least 14-mM, or at least 15-mM, or at least 16-mM, or at least 17-mM, or at least 18-mM, or at least 19-mM, or at least 20-mM, or at least 21-mM, or at least 22-mM, or at least 23-mM of the CDK4/6 antagonist.

In methods comprising an hormone receptor inhibitor, in some embodiments, when the hormone receptor inhibitor is a selective estrogen receptor modulators (SERM), selective estrogen receptor degraders (SERD), aromatase inhibitors (AI) or their combination, which can include tamoxifen, elacestrant, asanastrozole, exemestane or a concentration of the hormone receptor inhibitor administered to the subject or contacted to the cell may be at least 0.1-nM, or at least 0.5-nM, or at least 1-nM, or at least 5-nM, or at least 10-nM, or at least 25-nM, or at least 50-nM, or at least 1-µg/mL, or at least 5-µg/mL, or at least 10-µg/mL, or at least 20-µg/mL, or at least 25-µg/mL, or at least 50-µg/mL, or at least 60-µg/mL, or at least 70-µg/mL, or at least 80-µg/mL, or at least 90-µg/mL, or at least 0.5-mM, or at least 1-mM, or at least 2-mM, or at least 3-mM, or at least 4-mM, or at least 5-mM, or at least 6-mM, or at least 7-mM, or at least 8-mM, or at least 9-mM, or at least 10-mM, or at least 11-mM, or at least 12-mM, or at least 13-mM, or at least 14-mM, or at least 15-mM, or at least 16-mM, or at least 17-mM, or at least 18-mM, or at least 19-mM, or at least 20-mM, or at least 21-mM, or at least 22-mM, or at least 23-mM of the hormone receptor inhibitor.

In some embodiments, the controlled release formulation may be such that it does not dissipate from the site of the local administering, which may be, for example, a site of a metastatic cancer lesion, while the lanthanide (III) 9-R', 10-R" octadecanoate compound and/or an OGFR antagonist such as N-allyl noroxymorphone, a CDK4/6 inhibitor such as abemaciclib, or hormone receptor inhibitor such as tamoxifen, or a hormone receptor inhibitor such as elacestrant, or their combination, is being released.

Fatty Acid Lanthanide Chemistry

Lanthanides (Ln) are the series of elements that include lanthanum (La), cerium (Ce), praseodymium (Pr), neodymium (Nd), gadolinium (Gd), and terbium (Tb). All these elements have a 3+ oxidative state. One embodiment is a method of preparing a chemically modified fatty acid via reaction with a lanthanide salt while heating to produce a fatty acid ester.

In one method, the lanthanide salt is a lanthanide acetate with the generalized form $(Ln(CH_3COOOH)_3)$, and the fatty acid is a lauric acid $(C_{12}H_{24}O_2)$. The lanthanide is reacted with the lauric acid by heating to at least 900 C, the reaction produces a clear viscous solution that cools into an opaque waxy material while excess acetic acid and water are converted to vapor due to boiling. The equations for the reactions for lanthanum, cerium, praseodymium, neodymium, gadolinium, and terbium are as follows:

Lanthanum acetate is reacted with lauric acid when heated to at least 90° C. according to the equation: $La(CH_3COO)_3 \cdot XH_2O + 3(C_{12}H_{24}O_2) = La(C_{12}H_{23}O_2)_3 + 3(CH_3COOH) + XH_2O$. In this equation X=0, 1, 2, 3, 4, 5, 6, 7, 8, 9, 10, 11, or 12. This reaction produces lanthanum (III) tridodeconoate, which is a clear viscous material that forms a white waxy material upon cooling, which is soluble in the following non-polar solvents when heated to at least 90° C. that include but are not limited to toluene, xylene, n-octane, cyclohexane, hexane, chloroform, acetonitrile, ether, and any derivative of these non-polar solvents. In addition, the lanthanum (III) tridodeconoate is soluble in the following fatty acid solutions when heated to at least 900 C that include but are not limited to oleic acid, linoleic acid, vegetable oil, olive oil, canola oil, castor oil, and canola oil. The present embodiment includes compounds with the following structure:

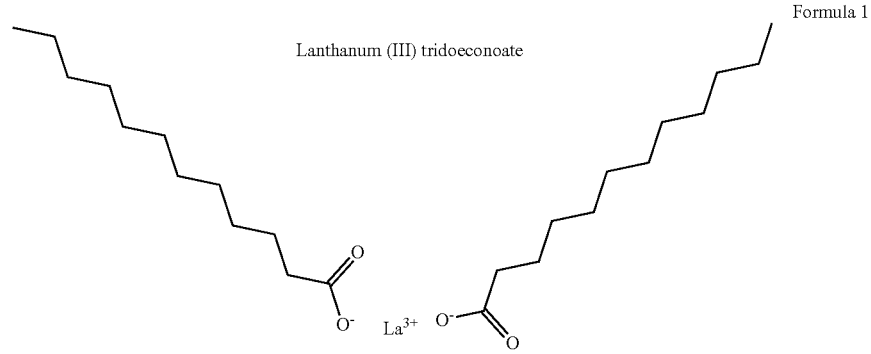

Lanthanum (III) tridoeconoate

Formula 1

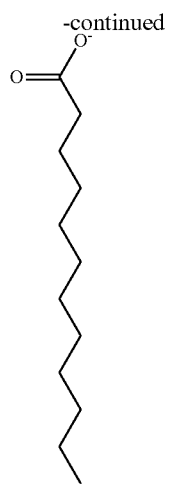

Lanthanum (III) tridoeconoate

Cerium acetate is reacted with lauric acid when heated to at least 90° C. according to the equation: $Ce(CH_3COO)_3 \cdot XH_2O + 3(C_{12}H_{24}O_2) = Ce(C_{12}H_{23}O_2)_3 + 3(CH_3COOH) + XH_2O$. In this equation X=0, 1, 1.5, 2, 3, 4.5, or 6. This reaction produces cerium (III) tridodeconoate, which is a clear orange/brown viscous material that forms an orange/brown waxy material upon cooling, which is soluble in the following non-polar solvents when heated to at least 90° C. that include but are not limited to toluene, xylene, n-octane, cyclohexane, hexane, chloroform, acetonitrile, ether, and any derivative of these non-polar solvents. In addition, the cerium (III) tridodeconoate is soluble in the following fatty acid solutions when heated to at least 900 C that include but are not limited to oleic acid, linoleic acid, vegetable oil, olive oil, canola oil, castor oil, and canola oil. The present embodiment includes compounds with the following structure:

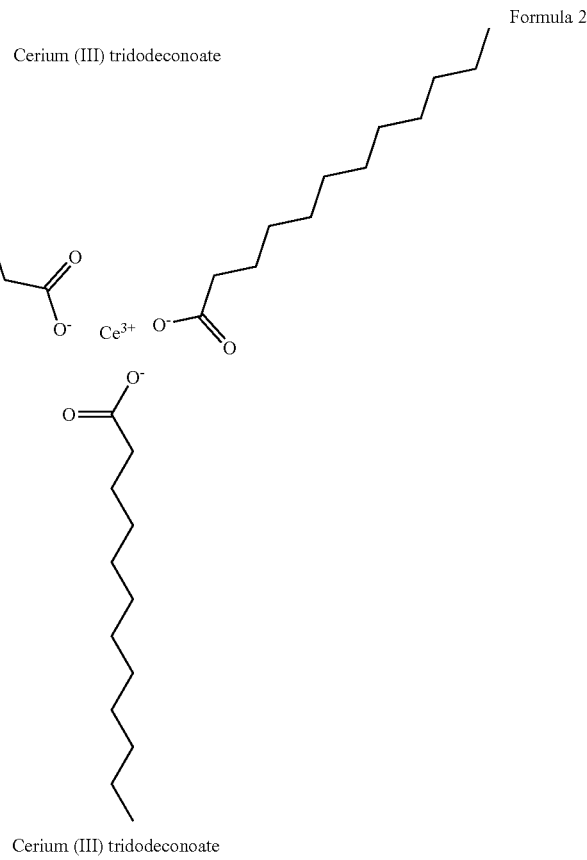

Formula 2

Cerium (III) tridodeconoate

Cerium (III) tridodeconoate

Praseodymium acetate is reacted with lauric acid when heated to at least 900 C according to the equation: $Pr(CH_3COO)_3 \cdot XH_2O + 3(C_{12}H_{24}O_2) = Pr(C_{12}H_{23}O_2)_3 + 3(CH_3COOH) + XH_2O$. In this equation X=0, 1, 2, 3, 4, 5, or 6. This reaction produces praseodymium (III) tridodeconoate, which is a clear green viscous material that forms a green waxy material upon cooling, which is soluble in the following non-polar solvents when heated to at least 90° C. that include but are not limited to toluene, xylene, n-octane, cyclohexane, hexane, chloroform, acetonitrile, ether, and any derivative of these non-polar solvents. In addition, the praseodymium (III) tridodeconoate is soluble in the following fatty acid solutions when heated to at least 90° C. that include but are not limited to oleic acid, linoleic acid, vegetable oil, olive oil, canola oil, castor oil, and canola oil. The present embodiment includes compounds with the following structure:

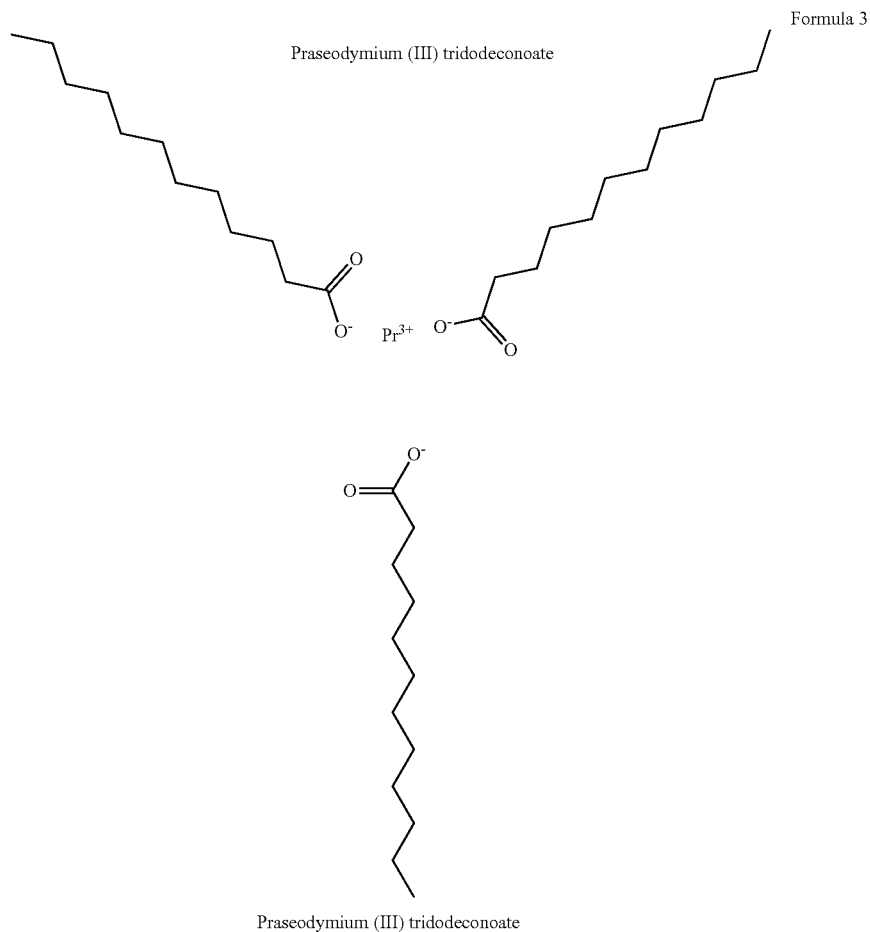

Formula 3

Praseodymium (III) tridodeconoate

Praseodymium (III) tridodeconoate

Neodymium acetate is reacted with lauric acid when heated to at least 90° C. according to the equation: $Nd(CH_3COO)_3 \cdot XH_2O + 3(C_{12}H_{24}O_2) = Nd(C_{12}H_{23}O_2)_3 + 3(CH_3COOH) + XH_2O$. In this equation X=0, 1, 2, 3, 4, 5, or 6. This reaction produces neodymium (III) tridodeconoate, which is a clear blue/violet viscous material that forms a blue/violet waxy material upon cooling, which is soluble in the following non-polar solvents when heated to at least 90° C. that include but are not limited to toluene, xylene, n-octane, cyclohexane, hexane, chloroform, acetonitrile, ether, and any derivative of these non-polar solvents. In addition, the neodymium (III) tridodeconoate is soluble in the following fatty acid solutions when heated to at least 90° C. that include but are not limited to oleic acid, linoleic acid, vegetable oil, olive oil, canola oil, castor oil, and canola oil. The present embodiment includes compounds with the following structure:

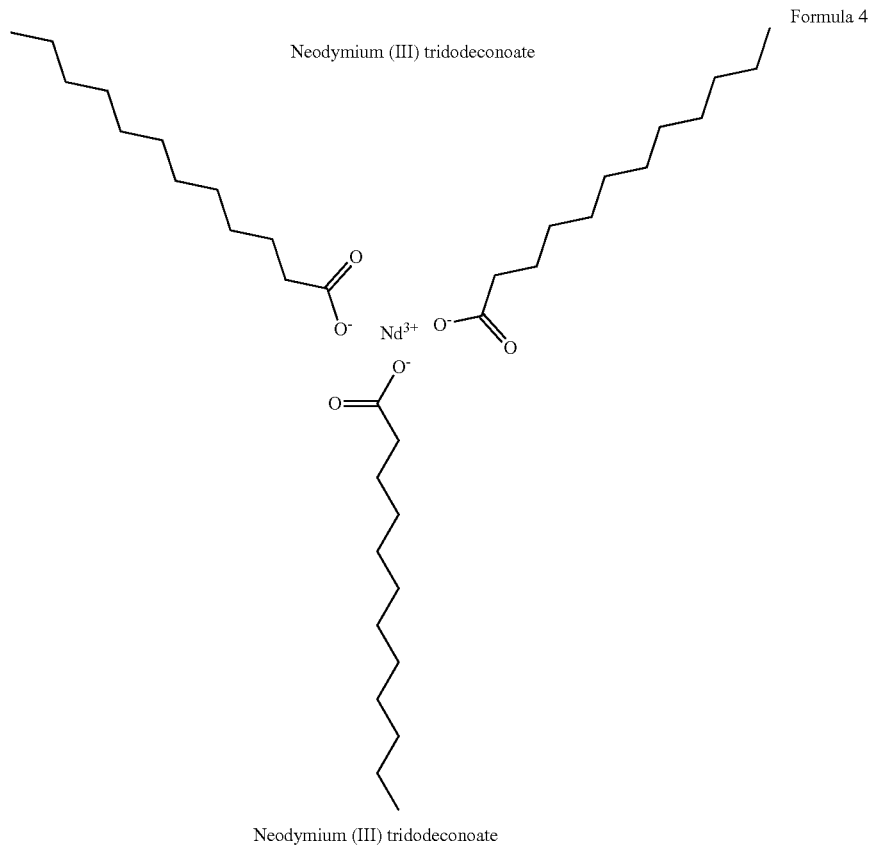

Neodymium (III) tridodeconoate

Formula 4

Gadolinium acetate is reacted with lauric acid when heated to at least 90° C. according to the equation: $Gd(CH_3COO)_3 \cdot XH_2O + 3(C_{12}H_{24}O_2) = Gd(C_{12}H_{23}O_2)_3 + 3(CH_3COOH) + XH_2O$. In this equation X=0, 1, 2, 3, 4, 5, or 6. This reaction produces gadolinium (III) tridodeconoate, which is a clear viscous material that forms a white waxy material upon cooling, which is soluble in the following non-polar solvents when heated to at least 90° C. that include but are not limited to toluene, xylene, n-octane, cyclohexane, hexane, chloroform, acetonitrile, ether, and any derivative of these non-polar solvents. In addition, the gadolinium (III) tridodeconoate is soluble in the following fatty acid solutions when heated to at least 90° C. that include but are not limited to oleic acid, linoleic acid, vegetable oil, olive oil, canola oil, castor oil, and canola oil. The present embodiment includes compounds with the following structure:

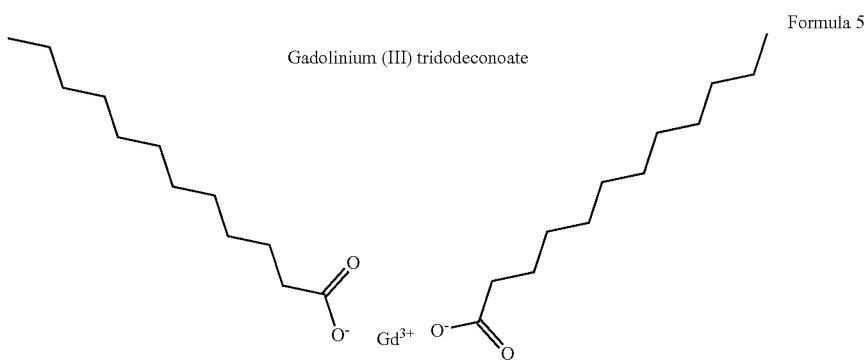

Gadolinium (III) tridodeconoate

Formula 5

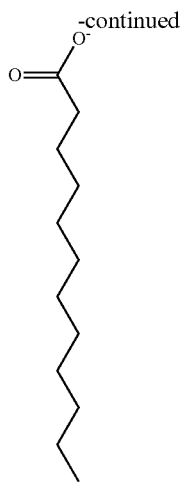

Gadolinium (III) tridodeconoate

Terbium acetate is reacted with lauric acid when heated to at least 90° C. according to the equation: $Tb(CH_3COO)_3 \cdot XH_2O + 3(C_{12}H_{24}O_2) = Tb(C_{12}H_{23}O_2)_3 + 3(CH_3COOH) + XH_2O$. In this equation X=0, 1, 2, 3, 4, 5, or 6. This reaction produces terbium (III) tridodeconoate, which is a clear viscous material that forms a white waxy material upon cooling, which is soluble in the following non-polar solvents when heated to at least 900 C that include but are not limited to toluene, xylene, n-octane, cyclohexane, hexane, chloroform, acetonitrile, ether, and any derivative of these non-polar solvents. In addition, the terbium (III) tridodeconoate is soluble in the following fatty acid solutions when heated to at least 900 C that include but are not limited to oleic acid, linoleic acid, vegetable oil, olive oil, canola oil, castor oil, and canola oil. The present embodiment includes compounds with the following structure:

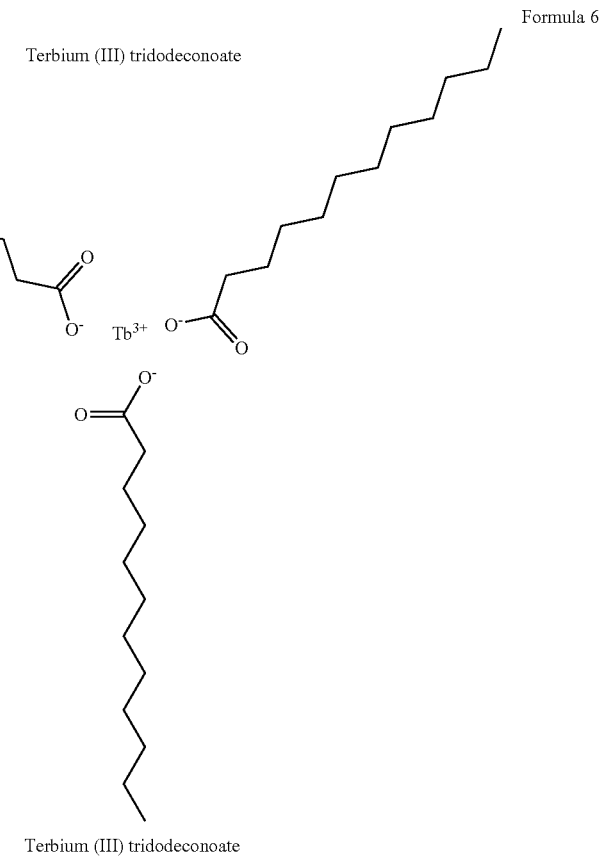

Formula 6

Terbium (III) tridodeconoate

In another method, In one method, the lanthanide salt is a lanthanide acetate with the generalized form (Ln(CH$_3$CO00H)$_3$), and the fatty acid is a palmitic acid (C$_{16}$H$_{32}$O$_2$). The lanthanide is reacted with the palmitic acid by heating to at least 180° C., the reaction produces a clear acid solutions when heated to at least 90° C. that include but are not limited to oleic acid, linoleic acid, vegetable oil, olive oil, canola oil, castor oil, and canola oil. The present embodiment includes compounds with the following structure:

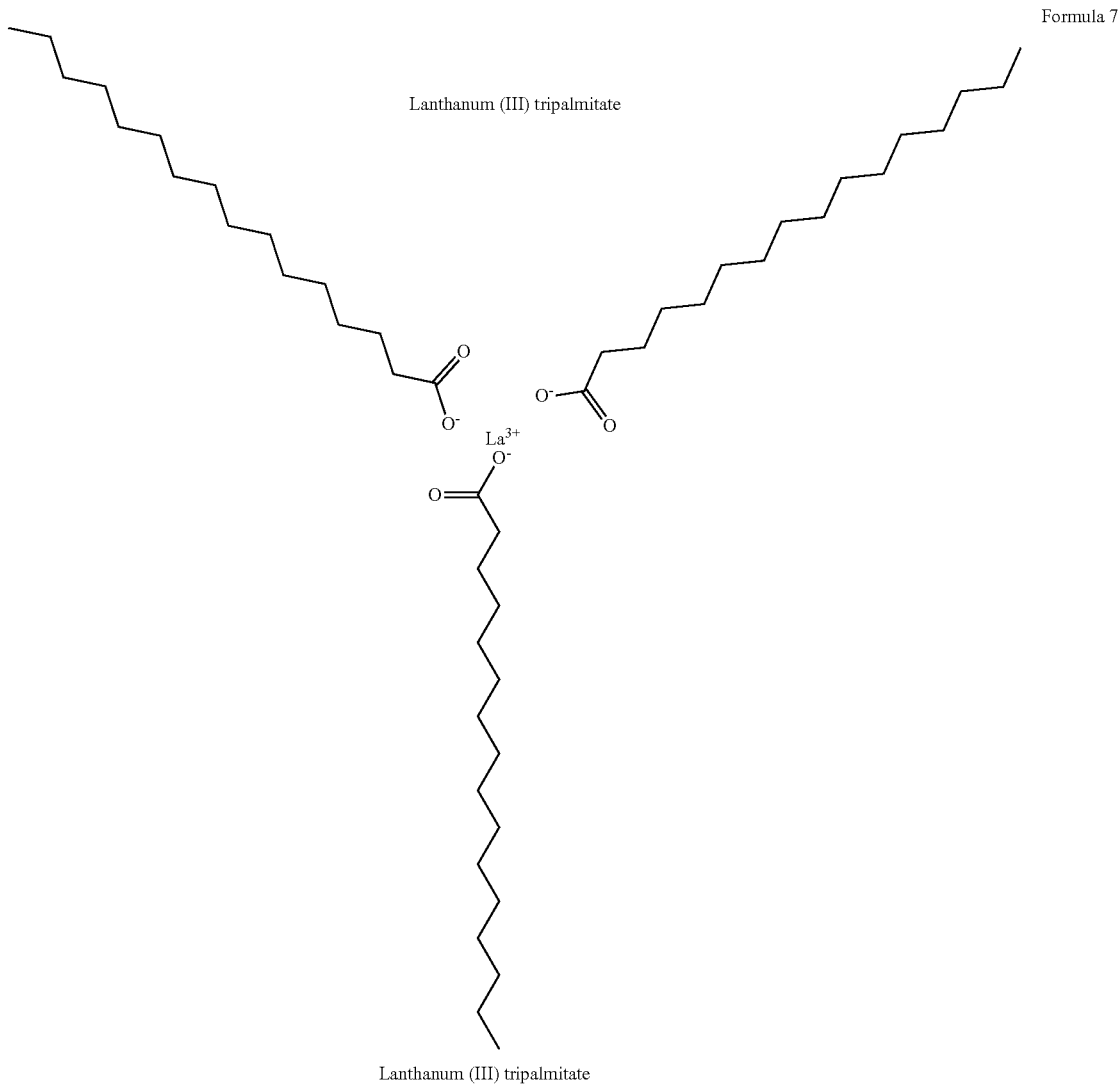

Formula 7 viscous solution that cools into an opaque waxy material while excess acetic acid and water are converted to vapor due to boiling. The equations for the reactions for lanthanum, cerium, praseodymium, neodymium, gadolinium, and terbium are as follows:

Lanthanum acetate is reacted with palmitic acid when heated to at least 180° C. according to the equation: La(CH$_3$COO)$_3$·XH$_2$O+3(C$_{16}$H$_{32}$O$_2$)=La(C$_{16}$H$_{31}$O$_2$)$_3$+3(CH$_3$COOH)+XH$_2$O. In this equation X=0, 1, 2, 3, 4, 5, 6, 7, 8, 9,10, 11, or 12. This reaction produces lanthanum (III) tripalmitate, which is a clear viscous material that forms a white waxy material upon cooling, which is soluble in the following non-polar solvents when heated to at least 90° C. that include but are not limited to toluene, xylene, n-octane, cyclohexane, hexane, chloroform, acetonitrile, ether, and any derivative of these non-polar solvents. In addition, the lanthanum (III) tripalmitate is soluble in the following fatty Cerium acetate is reacted with palmitic acid when heated to at least 1800 C according to the equation: Ce(CH$_3$COO)$_3$·XH$_2$O+3(C$_{16}$H$_{32}$O$_2$)=Ce(C$_{16}$H$_{31}$O$_2$)$_3$+3(CH$_3$COOH)+XH$_2$O. In this equation X=0, 1, 1.5, 2, 3, 4.5, or 6. This reaction produces cerium (III) tripalmitate, which is a clear orange/brown viscous material that forms an orange/brown waxy material upon cooling, which is soluble in the following non-polar solvents when heated to at least 90° C. that include but are not limited to toluene, xylene, n-octane, cyclohexane, hexane, chloroform, acetonitrile, ether, and any derivative of these non-polar solvents. In addition, the cerium (III) tripalmitate is soluble in the following fatty acid solutions when heated to at least 90° C. that include but are not limited to oleic acid, linoleic acid, vegetable oil, olive oil, canola oil, castor oil, and canola oil. The present embodiment includes compounds with the following structure:

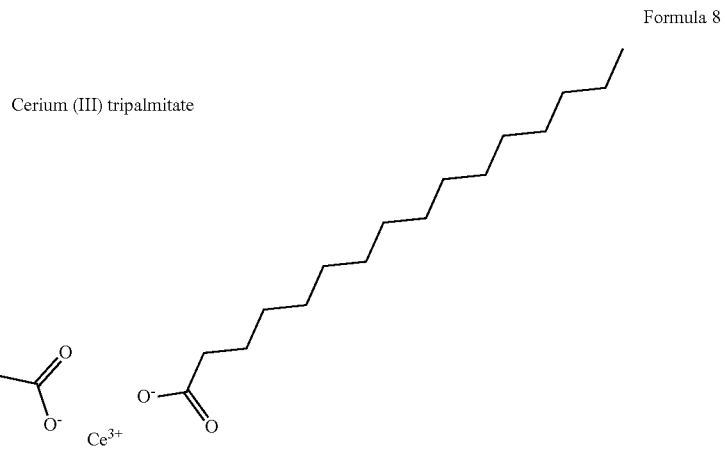

Cerium (III) tripalmitate

Formula 8

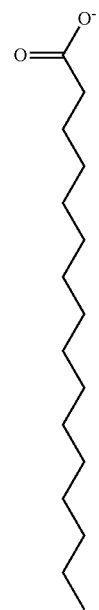

Cerium (III) tripalmitate

Praseodymium acetate is reacted with palmitic acid when heated to at least 1800 C according to the equation: $Pr(CH_3COO)_3 \cdot XH_2O + 3(C_{16}H_{32}O_2) = Pr(C_{16}H_{31}O_2)_3 + 3(CH_3COOH) + XH_2O$. In this equation X=0, 1, 2, 3, 4, 5, or 6. This reaction produces praseodymium (III) tripalmitate, which is a clear green viscous material that forms a green waxy material upon cooling, which is soluble in the following non-polar solvents when heated to at least 900 C that include but are not limited to toluene, xylene, n-octane, cyclohexane, hexane, chloroform, acetonitrile, ether, and any derivative of these non-polar solvents. In addition, the praseodymium (III) tripalmitate is soluble in the following fatty acid solutions when heated to at least 900 C that include but are not limited to oleic acid, linoleic acid, vegetable oil, olive oil, canola oil, castor oil, and canola oil. The present embodiment includes compounds with the following structure:

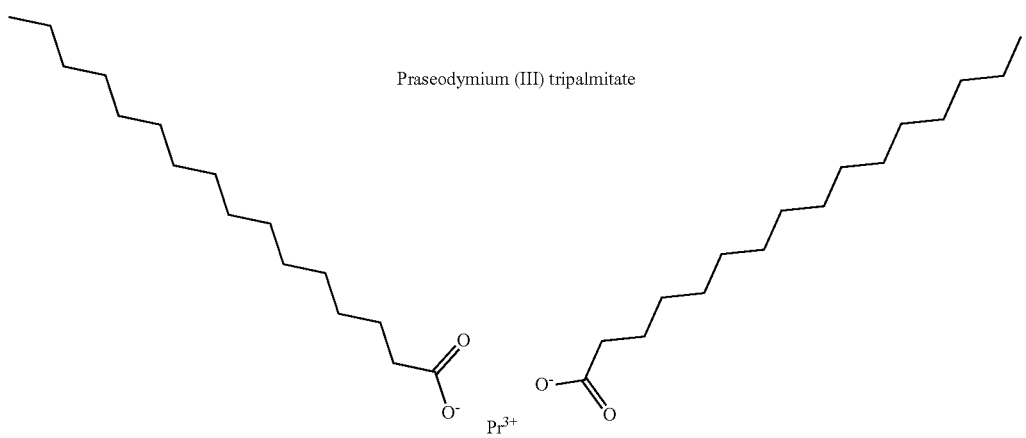
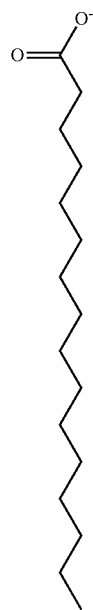

Praseodymium (III) tripalmitate

Formula 9

Neodymium acetate is reacted with palmitic acid when heated to at least 1800 C according to the equation: $Nd(CH_3COO)_3 \cdot XH_2O + 3(C_{16}H_{32}O_2) = Nd(C_{16}H_{31}O_2)_3 + 3(CH_3COOH) + XH_2O$. In this equation X=0, 1, 2, 3, 4, 5, or 6. This reaction produces neodymium (III) tripalmitate, which is a clear blue/violet viscous material that forms a blue/violet waxy material upon cooling, which is soluble in the following non-polar solvents when heated to at least 900 C that include but are not limited to toluene, xylene, n-octane, cyclohexane, hexane, chloroform, acetonitrile, ether, and any derivative of these non-polar solvents. In addition, the neodymium (III) tripalmitate is soluble in the following fatty acid solutions when heated to at least 900 C that include but are not limited to oleic acid, linoleic acid, vegetable oil, olive oil, canola oil, castor oil, and canola oil. The present embodiment includes compounds with the following structure:

Formula 10

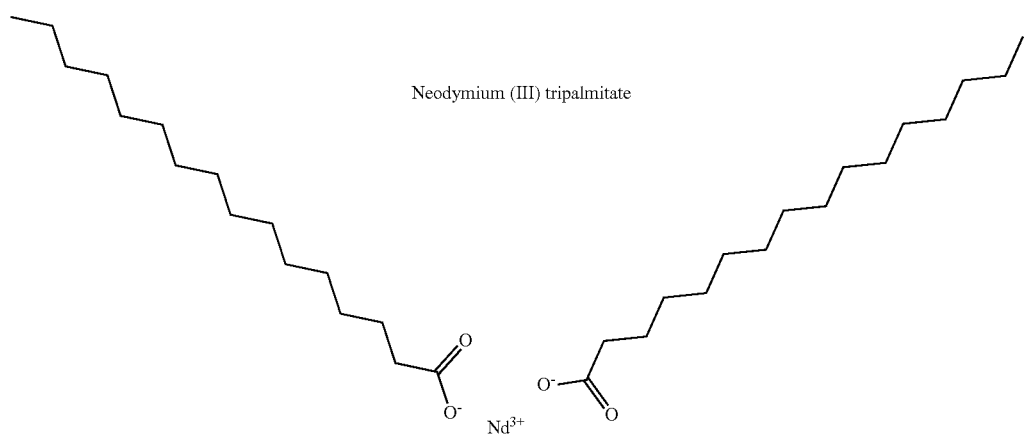

Neodymium (III) tripalmitate

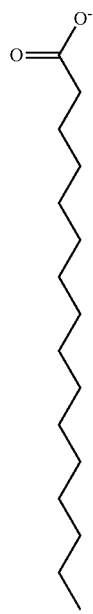

Neodymium (III) tripalmitate

Gadolinium acetate is reacted with palmitic acid when heated to at least 180° C. according to the equation: $Gd(CH_3COO)_3 \cdot XH_2O + 3(C_{16}H_{32}O_2) = Gd(C_{16}H_{31}O_2)_3 + 3(CH_3COOH) + XH_2O$. In this equation X=0, 1, 2, 3, 4, 5, or 6. This reaction produces gadolinium (III) tripalmitate, which is a clear viscous material that forms a white waxy material upon cooling, which is soluble in the following non-polar solvents when heated to at least 90° C. that include but are not limited to toluene, xylene, n-octane, cyclohexane, hexane, chloroform, acetonitrile, ether, and any derivative of these non-polar solvents. In addition, the gadolinium (III) tripalmitate is soluble in the following fatty acid solutions when heated to at least 90° C. that include but are not limited to oleic acid, linoleic acid, vegetable oil, olive oil, canola oil, castor oil, and canola oil. The present embodiment includes compounds with the following structure:

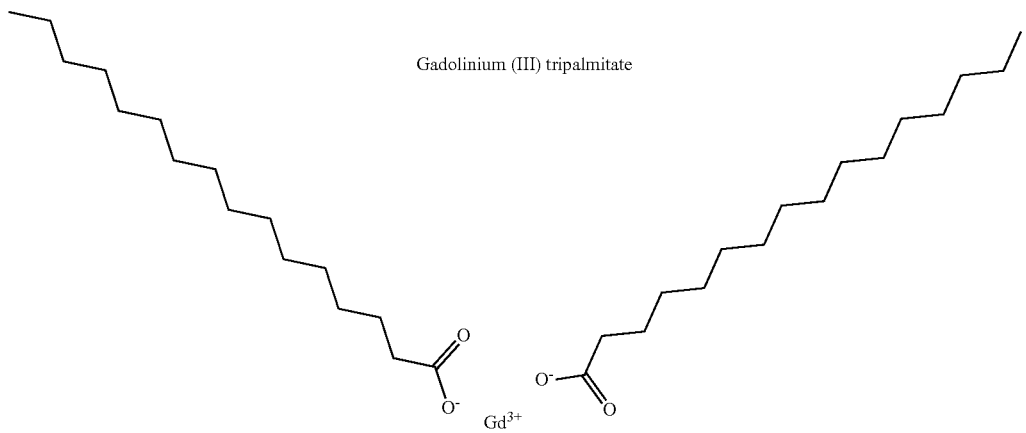

Gadolinium (III) tripalmitate

Formula 11

Gadolinium (III) tripalmitate

Terbium acetate is reacted with palmitic acid when heated to at least 180° C. according to the equation: $Tb(CH_3COO)_3 \cdot XH_2O + 3(C_{16}H_{32}O_2) = Tb(C_{16}H_{31}O_2)_3 + 3(CH_3COOH) + XH_2O$. In this equation X=0, 1, 2, 3, 4, 5, or 6. This reaction produces terbium (III) tripalmitate, which is a clear viscous material that forms a white waxy material upon cooling, which is soluble in the following non-polar solvents when heated to at least 900 C that include but are not limited to toluene, xylene, n-octane, cyclohexane, hexane, chloroform, acetonitrile, ether, and any derivative of these non-polar solvents. In addition, the terbium (III) tripalmitate is soluble in the following fatty acid solutions when heated to at least 900 C that include but are not limited to oleic acid, linoleic acid, vegetable oil, olive oil, canola oil, castor oil, and canola oil. The present embodiment includes compounds with the following structure:

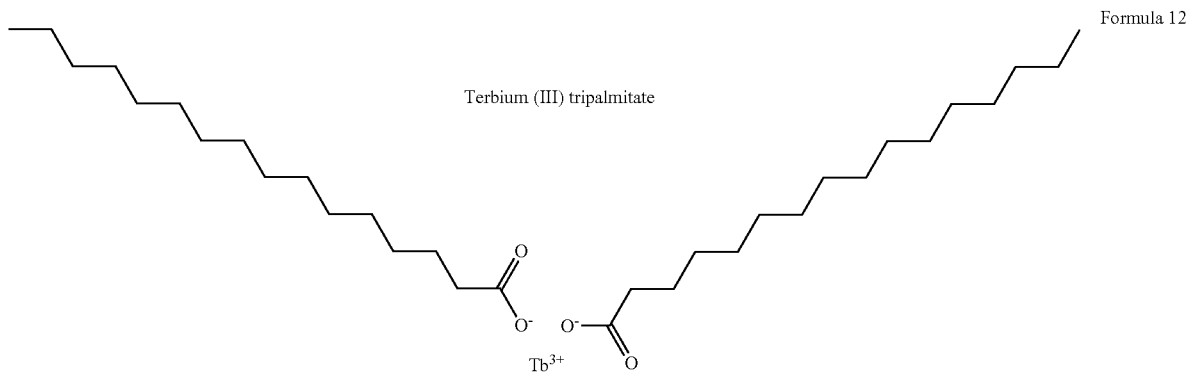

Terbium (III) tripalmitate

Formula 12

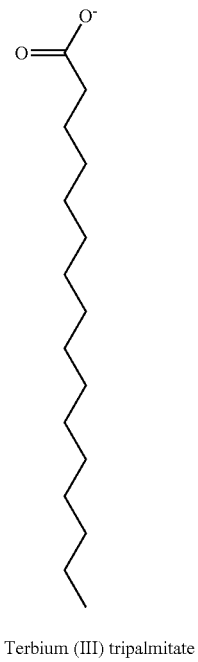

Terbium (III) tripalmitate

In another method, In one method, the lanthanide salt is a lanthanide acetate with the generalized form (Ln(CH$_3$CO00H)$_3$), and the fatty acid is a stearic acid (C$_{18}$H$_{36}$O$_2$). The lanthanide is reacted with the palmitic acid by heating to at least 225° C., the reaction produces a clear viscous solution that cools into an opaque waxy material while excess acetic acid and water are converted to vapor due to boiling. The equations for the reactions for lanthanum, cerium, praseodymium, neodymium, gadolinium, and terbium are as follows:

Lanthanum acetate is reacted with stearic acid when heated to at least 225° C. according to the equation: La(CH$_3$COO)$_3$·XH$_2$O+3(C$_{18}$H$_{36}$O$_2$)=La(C$_{18}$H$_{35}$O$_2$)$_3$+3(CH$_3$COOH)+XH$_2$O. In this equation X=0, 1, 2, 3, 4, 5, 6, 7, 8, 9,10, 11, or 12. This reaction produces lanthanum (III) tristearate, which is a clear viscous material that forms a white waxy material upon cooling, which is soluble in the following non-polar solvents when heated to at least 900 C that include but are not limited to toluene, xylene, n-octane, cyclohexane, hexane, chloroform, acetonitrile, ether, and any derivative of these non-polar solvents. In addition, the lanthanum (III) tristearate is soluble in the following fatty acid solutions when heated to at least 900 C that include but are not limited to oleic acid, linoleic acid, vegetable oil, olive oil, canola oil, castor oil, and canola oil. The present embodiment includes compounds with the following structure:

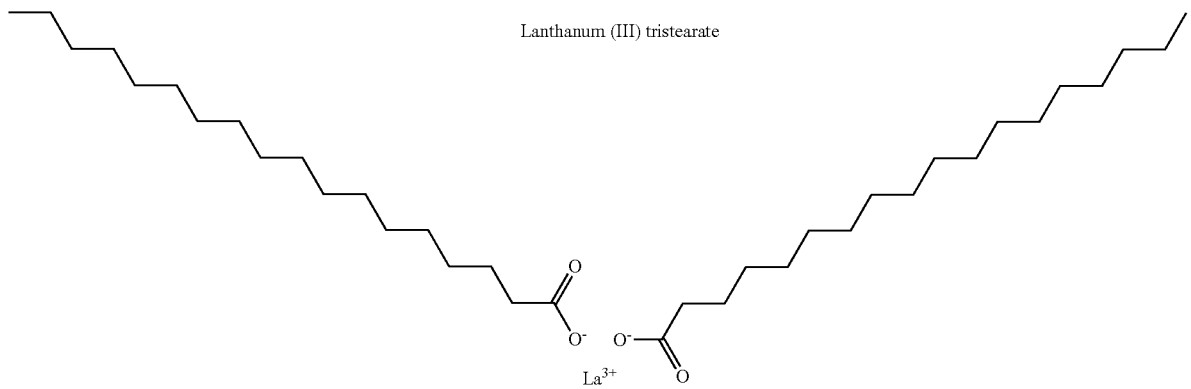

Lanthanum (III) tristearate

Formula 13

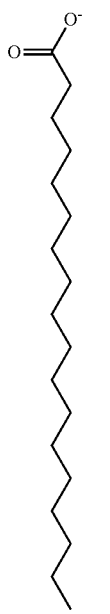

Lanthanum (III) tristearate

Cerium acetate is reacted with stearic acid when heated to at least 2250 C according to the equation: $Ce(CH_3COO)_3 \cdot XH_2O + 3(C_{18}H_{36}O_2) = Ce(C_{18}H_{35}O_2)_3 + 3(CH_3COOH) + XH_2O$. In this equation $X=0, 1, 1.5, 2, 3, 4.5,$ or $6$. This reaction produces cerium (III) tristearate, which is a clear orange/brown viscous material that forms an orange/brown waxy material upon cooling, which is soluble in the following non-polar solvents when heated to at least 90° C. that include but are not limited to toluene, xylene, n-octane, cyclohexane, hexane, chloroform, acetonitrile, ether, and any derivative of these non-polar solvents. In addition, the cerium (III) tristearate is soluble in the following fatty acid solutions when heated to at least 90° C. that include but are not limited to oleic acid, linoleic acid, vegetable oil, olive oil, canola oil, castor oil, and canola oil. The present embodiment includes compounds with the following structure:

Formula 14

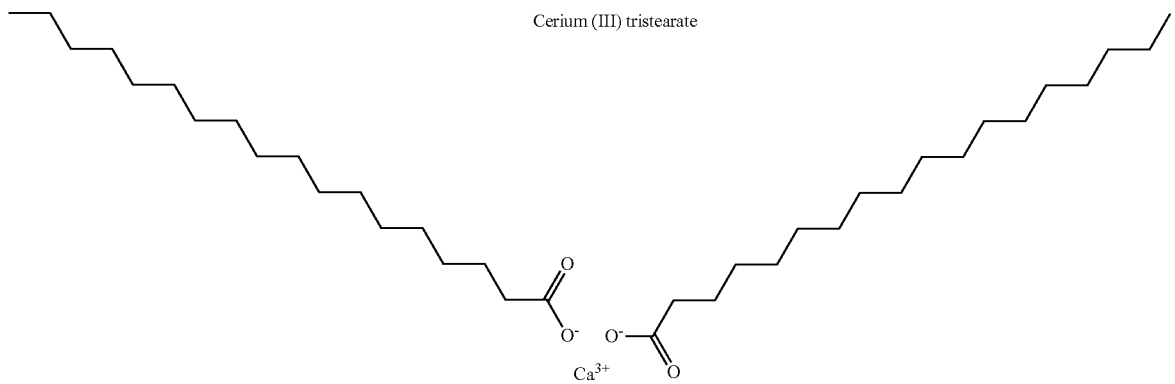

Cerium (III) tristearate

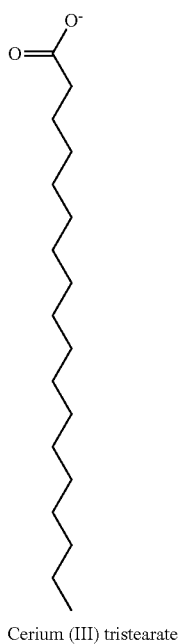

Cerium (III) tristearate

Praseodymium acetate is reacted with stearic acid when heated to at least 225° C. according to the equation: $Pr(CH_3COO)_3 \cdot XH_2O + 3(C_{18}H_{36}O_2) = Pr(C_{18}H_{35}O_2)_3 + 3(CH_3COOH) + XH_2O$. In this equation X=0, 1, 2, 3, 4, 5, or 6. This reaction produces praseodymium (III) tristearate, which is a clear green viscous material that forms a green waxy material upon cooling, which is soluble in the following non-polar solvents when heated to at least 90° C. that include but are not limited to toluene, xylene, n-octane, cyclohexane, hexane, chloroform, acetonitrile, ether, and any derivative of these non-polar solvents. In addition, the praseodymium (III) tristearate is soluble in the following fatty acid solutions when heated to at least 90° C. that include but are not limited to oleic acid, linoleic acid, vegetable oil, olive oil, canola oil, castor oil, and canola oil. The present embodiment includes compounds with the following structure:

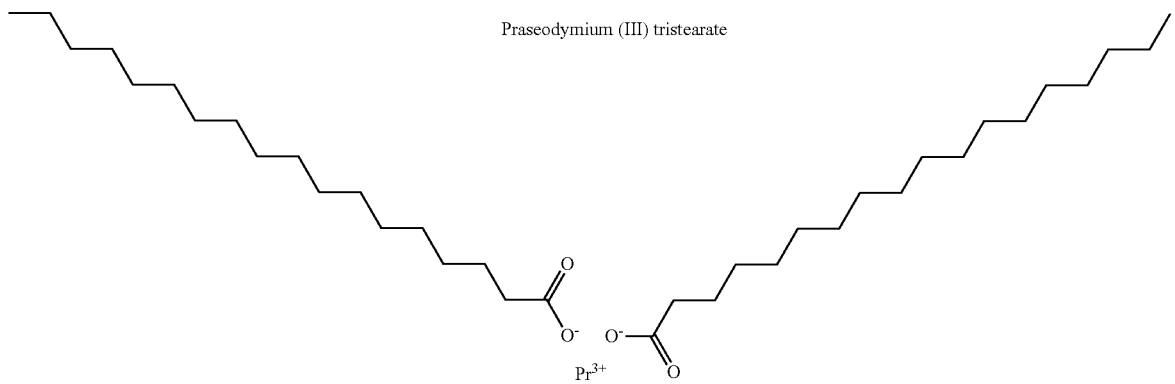
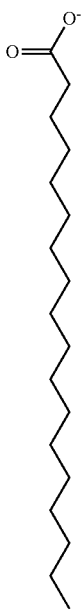

Formula 15

Praseodymium (III) tristearate

Neodymium acetate is reacted with stearic acid when heated to at least 225° C. according to the equation: $Nd(CH_3COO)_3 \cdot XH_2O + 3(C_{18}H_{36}O_2) = Nd(C_{18}H_{35}O_2)_3 + 3(CH_3COOH) + XH_2O$. In this equation X=0, 1, 2, 3, 4, 5, or 6. This reaction produces neodymium (III) tristearate, which is a clear blue/violet viscous material that forms a blue/violet waxy material upon cooling, which is soluble in the following non-polar solvents when heated to at least 90° C. that include but are not limited to toluene, xylene, n-octane, cyclohexane, hexane, chloroform, acetonitrile, ether, and any derivative of these non-polar solvents. In addition, the neodymium (III) tristearate is soluble in the following fatty acid solutions when heated to at least 90° C. that include but are not limited to oleic acid, linoleic acid, vegetable oil, olive oil, canola oil, castor oil, and canola oil. The present embodiment includes compounds with the following structure:

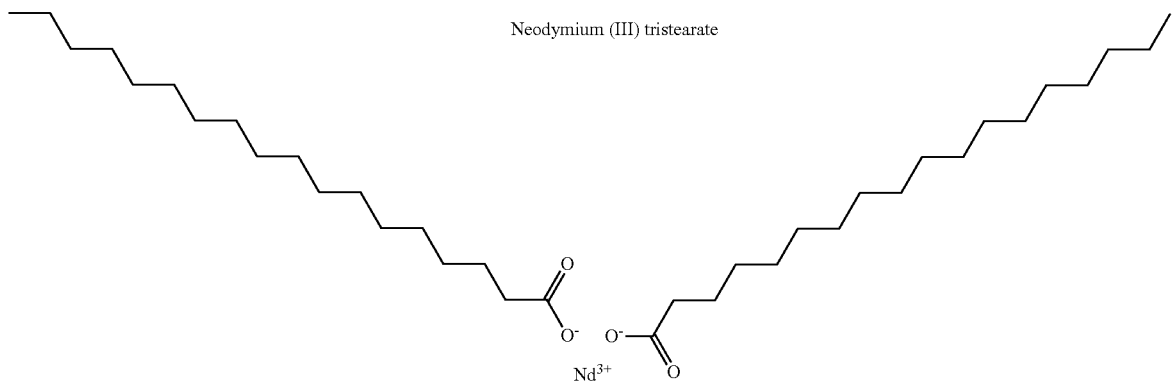

Neodymium (III) tristearate

Formula 16

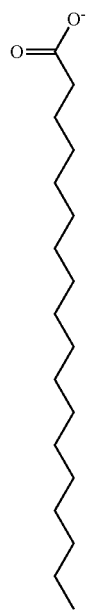

Neodymium (III) tristearate

Gadolinium acetate is reacted with stearic acid when heated to at least 225° C. according to the equation: $Gd(CH_3COO)_3 \cdot CH_2O + 3(C_{18}H_{36}O_2) = Gd(C_{18}H_{35}O_2)_3 + 3(CH_3COOH) + XH_2O$. In this equation X=0, 1, 2, 3, 4, 5, or 6. This reaction produces gadolinium (III) tristearate, which is a clear viscous material that forms a white waxy material upon cooling, which is soluble in the following non-polar solvents when heated to at least 90° C. that include but are not limited to toluene, xylene, n-octane, cyclohexane, hexane, chloroform, acetonitrile, ether, and any derivative of these non-polar solvents. In addition, the gadolinium (III) tristearate is soluble in the following fatty acid solutions when heated to at least 90° C. that include but are not limited to oleic acid, linoleic acid, vegetable oil, olive oil, canola oil, castor oil, and canola oil. The present embodiment includes compounds with the following structure:

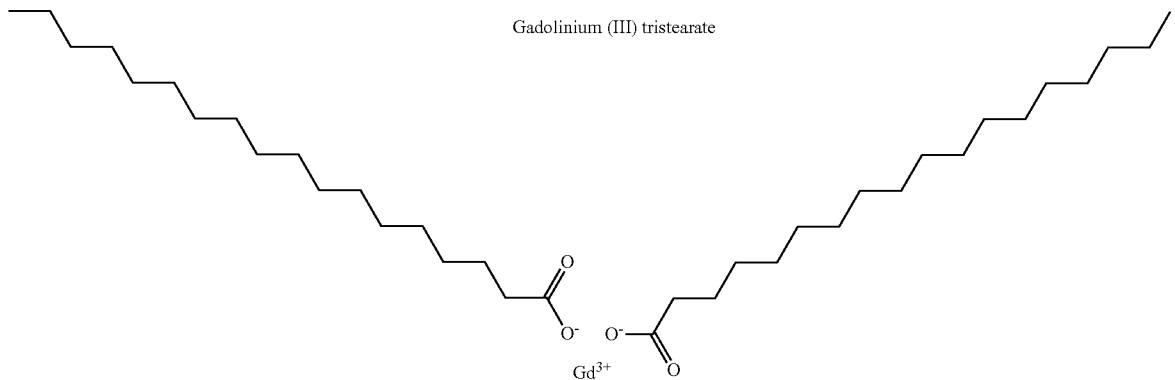

Formula 17

Gadolinium (III) tristearate

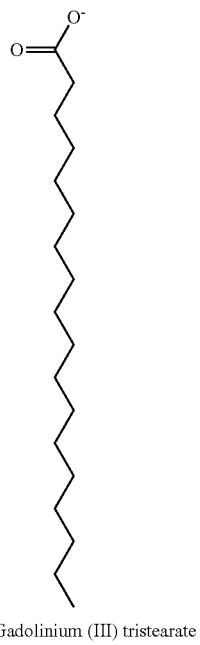

Gadolinium (III) tristearate

Terbium acetate is reacted with stearic acid when heated to at least 225° C. according to the equation: $b(CH_3COO)_3 \cdot XH_2O + 3(C_{18}H_{36}O_2) = b(C_{18}H_{35}O_2)_3 + 3(CH_3OOH) + XH_2O$. In this equation X=, 1, 2, 3, 4, 5, or 6. This reaction produces terbium (III) tristearate, which is a clear viscous material that forms a white waxy material upon cooling, which is soluble in the following non-polar solvents when heated to at least 900 C that include but are not limited to toluene, xylene, n-octane, cyclohexane, hexane, chloroform, acetonitrile, ether, and any derivative of these non-polar solvents. In addition, the terbium (III) tristearate is soluble in the following fatty acid solutions when heated to at least 90° C. that include but are not limited to oleic acid, linoleic acid, vegetable oil, olive oil, canola oil, castor oil, and canola oil. The present embodiment includes compounds with the following structure:

Formula 18

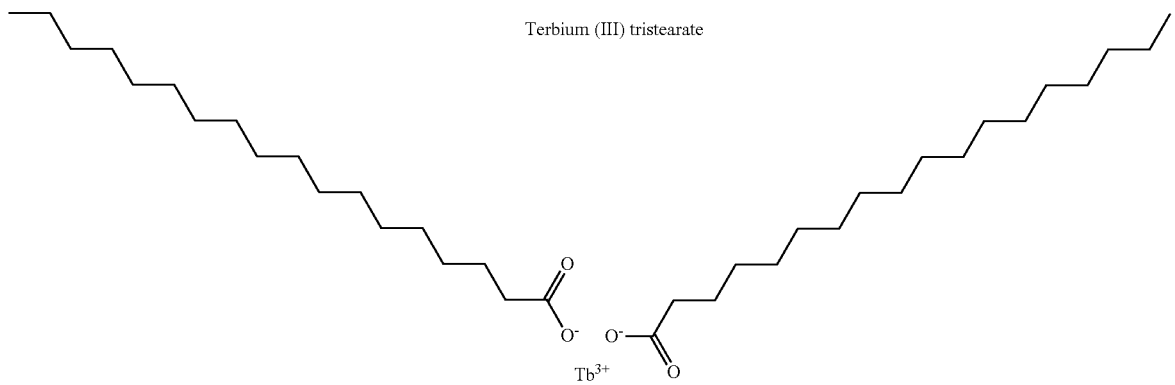

Terbium (III) tristearate

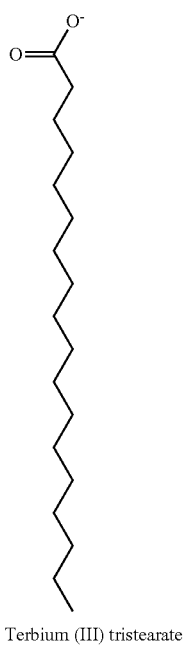

Terbium (III) tristearate

In another method, In one method, the lanthanide salt is a lanthanide acetate with the generalized form (Ln (CH$_3$C$_{00}$H)$_3$), and the fatty acid is an oleic acid (C$_{18}$H$_{34}$O$_2$). The lanthanide is reacted with the palmitic acid by heating to at least 270° C., the reaction produces a clear viscous solution that cools into an opaque waxy material while excess acetic acid and water are converted to vapor due to boiling. The equations for the reactions for lanthanum, cerium, praseodymium, neodymium, gadolinium, and terbium are as follows:

Lanthanum acetate is reacted with oleic acid when heated to at least 270° C. according to the equation: La(CH$_3$COO)$_3$·XH$_2$O+3(C$_{18}$H$_{34}$O$_2$)=La[(C$_{18}$H$_{33}$O$_2$)·(CH$_3$COO)$_2$]$_3$+CH$_3$COOH+XH$_2$O. In this equation X=0, 1, 2, 3, 4, 5, 6, 7, 8, 9,10, 11, or 12. During this reaction lanthanum (III) oleate forms, which results in the production of the following transient reaction products: First, hydrogen ions (H$^+$) displaced from each oleic acid molecule by the lanthanum (III) react with excess water to form three hydronium ions (H$_3$O$^+$). Two of the three ethanoate ions (CH$_3$COO$^-$) donated by the lanthanum (III) acetate reduce the unsaturated bond in oleic acid while the hydronium ions donate a hydrogen ion to the remaining ethanoate ion to produce acetic acid, with any remaining water/hydronium ions turning to vapor due to boiling. This reaction produces lanthanum (III) tri 9,10-diacetoxy octadecanoate, which is a clear viscous material that forms a clear resinous material upon cooling, which is soluble in the following non-polar solvents when heated to at least 900 C that include but are not limited to toluene, xylene, n-octane, cyclohexane, hexane, chloroform, acetonitrile, ether, and any derivative of these non-polar solvents. In addition, the lanthanum (III) tri 9,10-diacetoxy octadecanoate is soluble in the following fatty acid solutions when heated to at least 90° C. that include but are not limited to oleic acid, linoleic acid, vegetable oil, olive oil, canola oil, castor oil, and canola oil. The present embodiment includes compounds with the following structure:

Formula 19

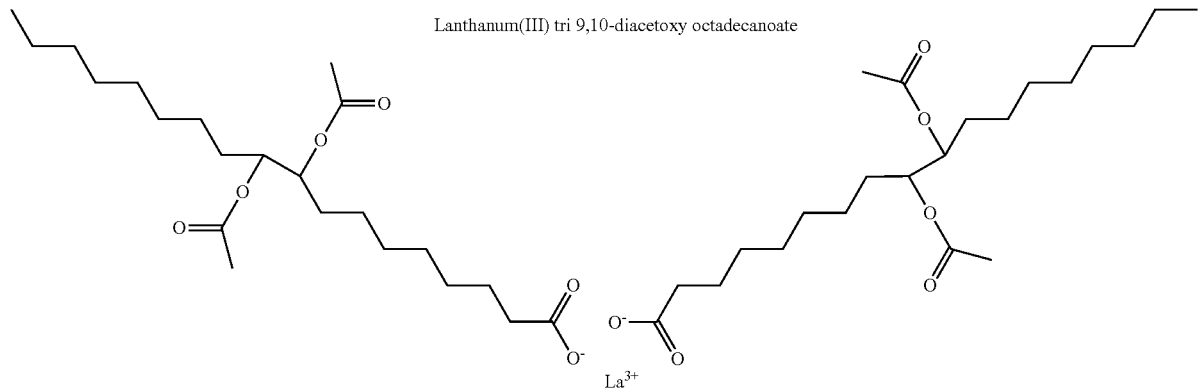

Lanthanum(III) tri 9,10-diacetoxy octadecanoate

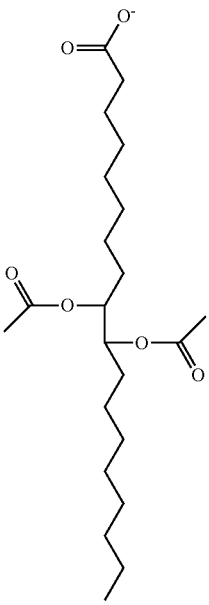

Lanthanum (III) tri 9,10-diacetoxy octadecanoate

Cerium acetate is reacted with oleic acid when heated to at least 2700 C according to the equation: $Ce(CH_3COO)_3 \cdot XH_2O + 3(C_{18}H_{34}O_2) = Ce[(C_{18}H_{33}O_2) \cdot (CH_3COO)_2]_3 + CH_3COOH + XH_2O$. In this equation X=0, 1, 1.5, 2, 3, 4.5, or 6. During this reaction cerium (III) oleate forms, which results in the production of the following transient reaction products: First, hydrogen ions ($H^+$) displaced from each oleic acid molecule by the cerium (III) react with excess water to form three hydronium ions ($H_3O^+$). Two of the three ethanoate ions ($CH_3COO^-$) donated by the cerium (III) acetate reduce the unsaturated bond in oleic acid while the hydronium ions donate a hydrogen ion to the remaining ethanoate ion to produce acetic acid, with any remaining water/hydronium ions turning to vapor due to boiling. This reaction produces cerium (III) tri 9,10-diacetoxy octadecanoate, which is a clear orange/brown viscous material that forms a clear orange/brown resinous material upon cooling, which is soluble in the following non-polar solvents when heated to at least 90° C. that include but are not limited to toluene, xylene, n-octane, cyclohexane, hexane, chloroform, acetonitrile, ether, and any derivative of these non-polar solvents. In addition, the cerium (III) tri 9,10-diacetoxy octadecanoate is soluble in the following fatty acid solutions when heated to at least 900 C that include but are not limited to oleic acid, linoleic acid, vegetable oil, olive oil, canola oil, castor oil, and canola oil. The present embodiment includes compounds with the following structure:

Formula 20

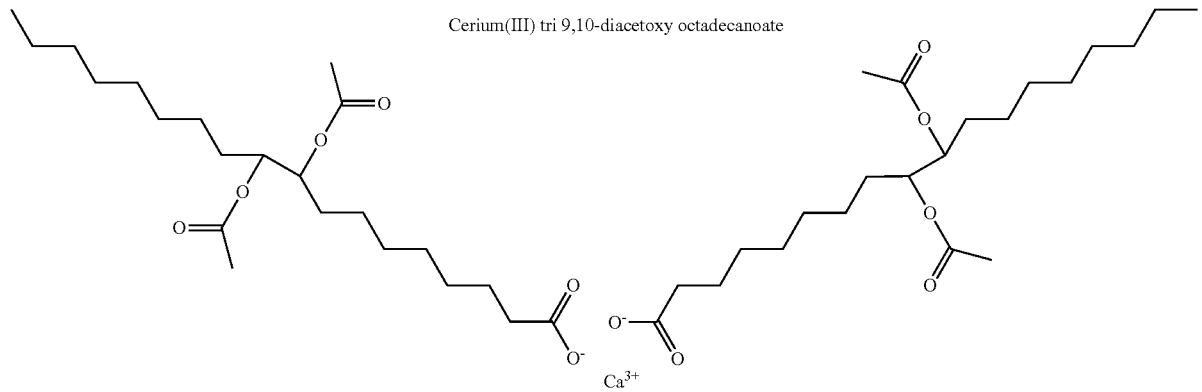

Cerium(III) tri 9,10-diacetoxy octadecanoate

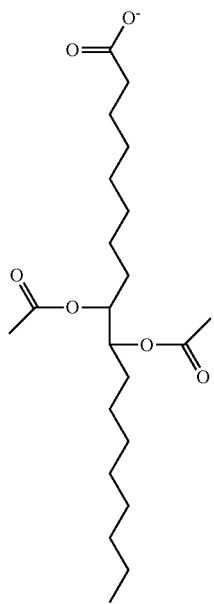

Cerium (III) tri 9,10-diacetoxy octadecanoate

Praseodymium acetate is reacted with oleic acid when heated to at least 270° C. according to the equation: $Pr(CH_3COO)_3 \cdot XH_2O + 3(C_{18}H_{34}O_2) = Pr[(C_{18}H_{33}O_2) \cdot (CH_3COO)_2]_3 + CH_3COOH + XH_2O$. In this equation X=0, 1, 2, 3, 4, 5, or 6. During this reaction praseodymium (III) oleate forms, which results in the production of the following transient reaction products: First, hydrogen ions ($H^+$) displaced from each oleic acid molecule by the praseodymium (III) react with excess water to form three hydronium ions ($H_3O^+$). Two of the three ethanoate ions ($CH_3COO^-$) donated by the praseodymium (III) acetate reduce the unsaturated bond in oleic acid while the hydronium ions donate a hydrogen ion to the remaining ethanoate ion to produce acetic acid, with any remaining water/hydronium ions turning to vapor due to boiling. This reaction produces praseodymium (III) tri 9,10-diacetoxy octadecanoate, which is a clear green viscous material that forms a clear green resinous material upon cooling, which is soluble in the following non-polar solvents when heated to at least 90° C. that include but are not limited to toluene, xylene, n-octane, cyclohexane, hexane, chloroform, acetonitrile, ether, and any derivative of these non-polar solvents. In addition, the praseodymium (III) tri 9,10-diacetoxy octadecanoate is soluble in the following fatty acid solutions when heated to at least 90° C. that include but are not limited to oleic acid, linoleic acid, vegetable oil, olive oil, canola oil, castor oil, and canola oil. The present embodiment includes compounds with the following structure:

Formula 21

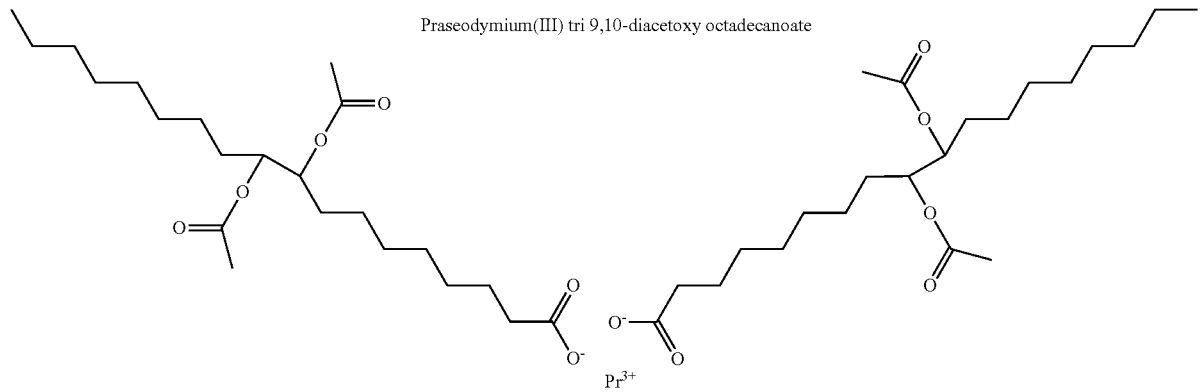

Praseodymium(III) tri 9,10-diacetoxy octadecanoate

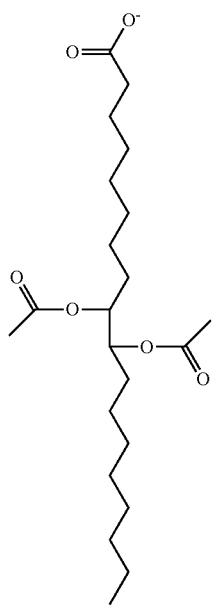

Praseodymium (III) tri 9,10-diacetoxy octadecanoate

Neodymium acetate is reacted with oleic acid when heated to at least 2700 C according to the equation: $Nd(CH_3COO)_3 \cdot XH_2O + 3(C_{18}H_{34}O_2) = Nd[(C_{18}H_{33}O_2) \cdot (CH_3COO)_2]_3 + CH_3COOH + XH_2O$. In this equation X=0, 1, 2, 3, 4, 5, or 6. During this reaction neodymium (III) oleate forms, which results in the production of the following transient reaction products: First, hydrogen ions ($H^+$) displaced from each oleic acid molecule by the neodymium (III) react with excess water to form three hydronium ions ($H_3O^+$). Two of the three ethanoate ions ($CH_3COO^-$) donated by the neodymium (III) acetate reduce the unsaturated bond in oleic acid while the hydronium ions donate a hydrogen ion to the remaining ethanoate ion to produce acetic acid, with any remaining water/hydronium ions turning to vapor due to boiling. This reaction produces neodymium (III) tri 9,10-diacetoxy octadecanoate, which is a clear blue/violet viscous material that forms a clear blue/violet resinous material upon cooling, which is soluble in the following non-polar solvents when heated to at least 900 C that include but are not limited to toluene, xylene, n-octane, cyclohexane, hexane, chloroform, acetonitrile, ether, and any derivative of these non-polar solvents. In addition, the neodymium (III) tri 9,10-diacetoxy octadecanoate is soluble in the following fatty acid solutions when heated to at least 90° C. that include but are not limited to oleic acid, linoleic acid, vegetable oil, olive oil, canola oil, castor oil, and canola oil. The present embodiment includes compounds with the following structure:

Formula 22

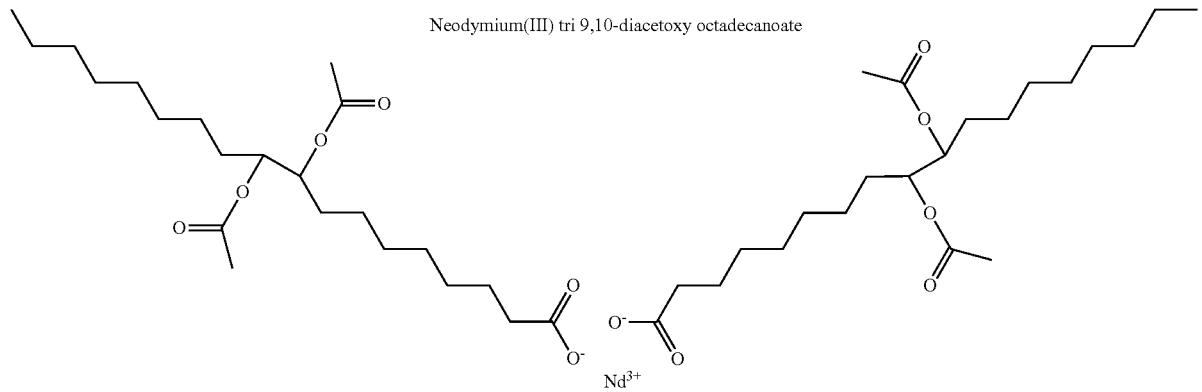

Neodymium(III) tri 9,10-diacetoxy octadecanoate

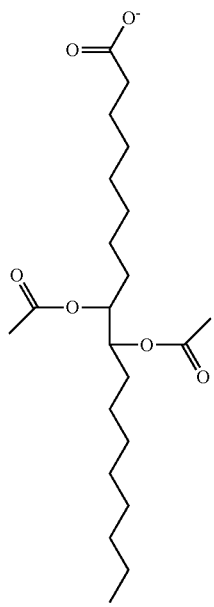

Neodymium (III) tri 9,10-diacetoxy octadecanoate

Gadolinium acetate is reacted with oleic acid when heated to at least 270° C. according to the equation: $Gd(CH_3COO)_3 \cdot XH_2O + 3(C_{18}H_{34}O_2) = Gd(C_{18}H_{33}O_2) \cdot (CH_3COOH)_2]_3 + CH_3COOH + XH_2O$. In this equation X=0, 1, 2, 3, 4, 5, or 6. During this reaction neodymium gadolinium (III) oleate forms, which results in the production of the following transient reaction products: First, hydrogen ions ($H^+$) displaced from each oleic acid molecule by the gadolinium (III) react with excess water to form three hydronium ions ($H_3O^+$). Two of the three ethanoate ions ($CH_3COO^-$) donated by the gadolinium (III) acetate reduce the unsaturated bond in oleic acid while the hydronium ions donate a hydrogen ion to the remaining ethanoate ion to produce acetic acid, with any remaining water/hydronium ions turning to vapor due to boiling. This reaction produces gadolinium (III) tri 9,10-diacetoxy octadecanoate, which is a clear viscous material that forms a clear resinous material upon cooling, which is soluble in the following non-polar solvents when heated to at least 900 C that include but are not limited to toluene, xylene, n-octane, cyclohexane, hexane, chloroform, acetonitrile, ether, and any derivative of these non-polar solvents. In addition, the gadolinium (III) tri 9,10-diacetoxy octadecanoate is soluble in the following fatty acid solutions when heated to at least 900 C that include but are not limited to oleic acid, linoleic acid, vegetable oil, olive oil, canola oil, castor oil, and canola oil. The present embodiment includes compounds with the following structure:

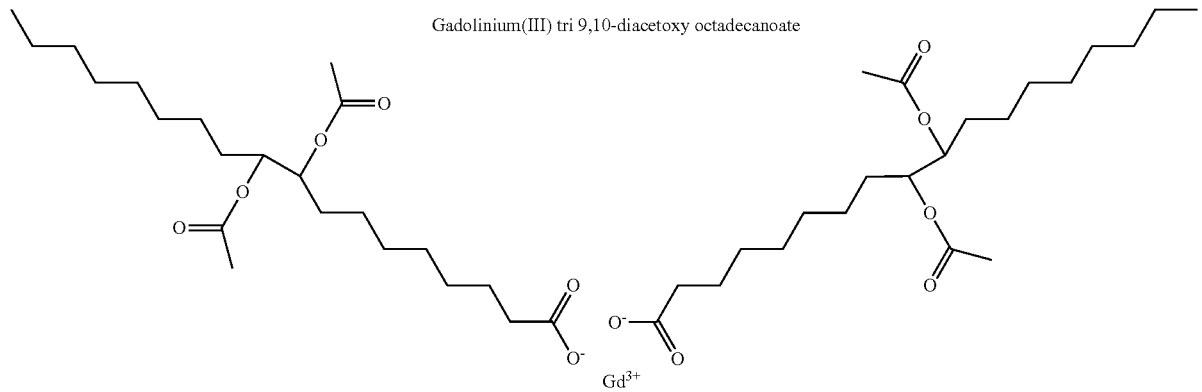

Gadolinium(III) tri 9,10-diacetoxy octadecanoate

Formula 23

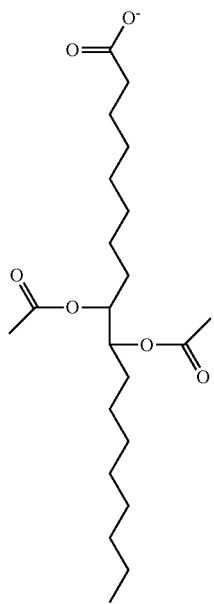

Gadolinium (III) tri 9,10-diacetoxy octadecanoate

Terbium acetate is reacted with oleic acid when heated to at least 2700 C according to the equation: $Tb(CH_3COO)_3 \cdot XH_2O + 3(C_{18}H_{34}O_2) = Tb[(C_{18}H_{33}O_2)(CH_3COO)_2]_3 + CH_3COOH + XH_2O$. In this equation X=, 1, 2, 3, 4, 5, or 6. During this reaction neodymium terbium (III) oleate forms, which results in the production of the following transient reaction products: First, hydrogen ions ($H^+$) displaced from each oleic acid molecule by the terbium (III) react with excess water to form three hydronium ions ($H_3O^+$). Two of the three ethanoate ions ($CH_3COO\&$) donated by the terbium (III) acetate reduce the unsaturated bond in oleic acid while the hydronium ions donate a hydrogen ion to the remaining ethanoate ion to produce acetic acid, with any remaining water/hydronium ions turning to vapor due to boiling. This reaction produces terbium (III) tri 9,10-diacetoxy octadecanoate, which is a clear viscous material that forms a clear resinous material upon cooling, which is soluble in the following non-polar solvents when heated to at least 90' C that include but are not limited to toluene, xylene, n-octane, cyclohexane, hexane, chloroform, acetonitrile, ether, and any derivative of these non-polar solvents. In addition, the terbium (III) tri 9,10-diacetoxy octadecanoate is soluble in the following fatty acid solutions when heated to at least 90° C. that include but are not limited to oleic acid, linoleic acid, vegetable oil, olive oil, canola oil, castor oil, and canola oil. The present embodiment includes compounds with the following structure:

Formula 24

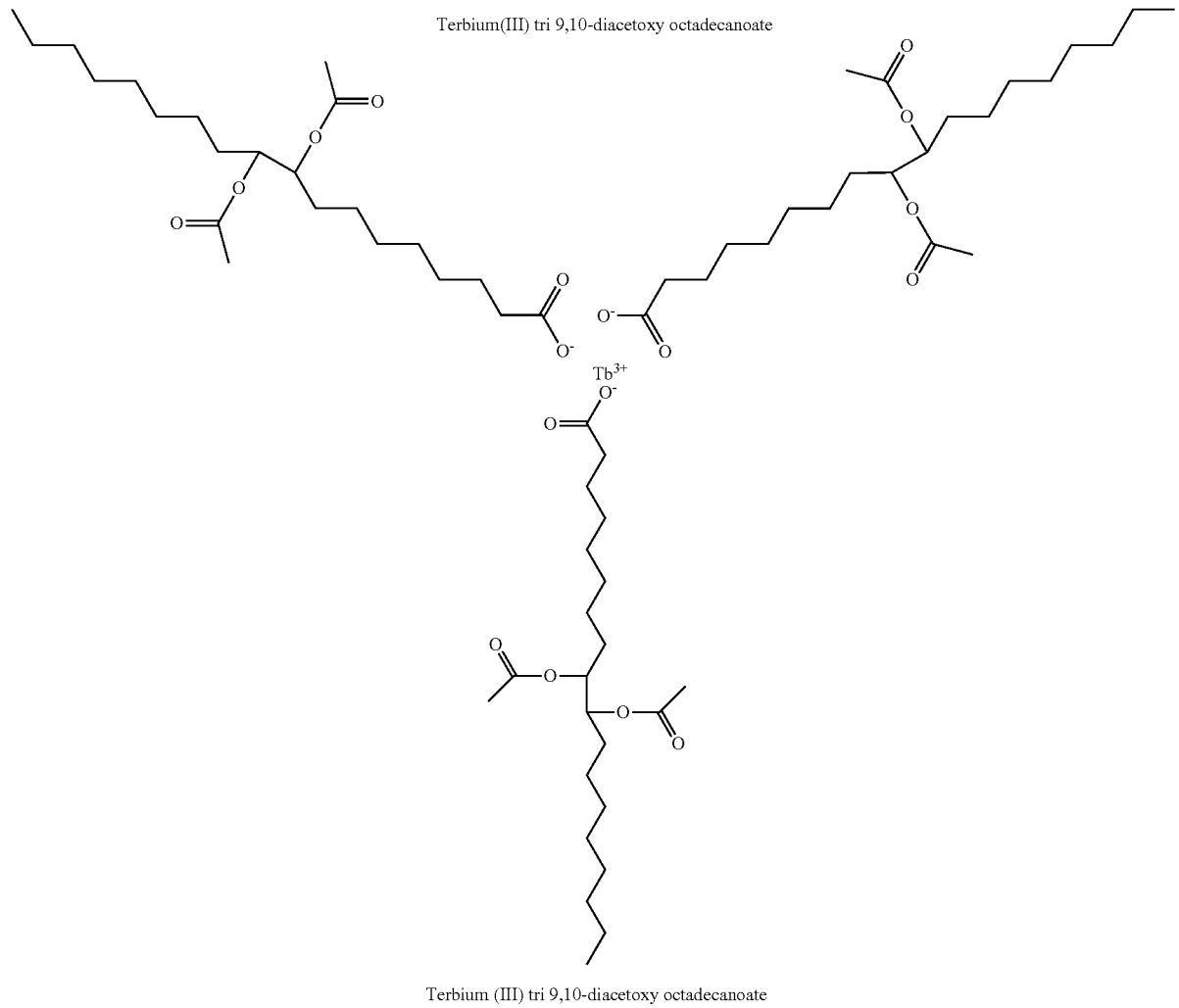

Terbium (III) tri 9,10-diacetoxy octadecanoate

In one embodiment, the lanthanide (III) tri 9-R', 10-R" octadecanoate can be generalized. In one embodiment, this generalized structure comprises an unsaturated oleate such that $Ln(C_{18}H_{33}O_2)_3$. In another embodiment, this generalized structure comprises an R' that can be a hydrogen ($H^+$), a hydroxide ($OH^-$), an ethanoate ($CH_3COO^-$), or an ether ($R^1$—O—$R^2$), in which $R^1$=hydrogen ($H^+$), an aryl group, or an alkyl group and $R^2$=hydrogen ($H^+$), an aryl group, or an alkyl group. R' can be a halide that includes the following: a chlorine ion ($Cl^-$), a fluorine ion ($F^-$), bromine ion ($Br^-$), or an iodine ion ($I^-$). R' can also be carboxylic acid, citrate, oxalate, or any of the chalcogens such as oxygen ($O_2$) or sulfur ($S_2$). R' can also be a sulfite, sulfate, nitrite, or nitrate.

R' can also be modified using nucleophilic acyl substitution reactions where an acetoxy group acts as a leaving group, allowing another nucleophile to attack and replace it, effectively changing the functional group attached to the oxygen atom; this is commonly achieved through hydrolysis to remove the acetyl group, or by reacting with other nucleophiles like amines or thiols to introduce different functionalities. Thereafter an amine or thiol group can be substituted or unsubstituted and there can be one substituent or more than one substituent that includes an alkyl, alkylaryl, alkene, amine, or any functional group that can normally be added via acyl substitution. In another embodiment, this generalized structure comprises an R" that can be a hydrogen ($H^+$), a hydroxide ($OH^-$), an ethanoate ($CH_3COO^-$), or an ether ($R^1$—O—$R^2$), in which $R^1$=hydrogen ($H^+$), an aryl group, or an alkyl group and $R^2$=hydrogen ($H^+$), an aryl group, or an alkyl group. R" can be a halide that includes the following: a chlorine ion ($Cl^-$), a fluorine ion ($F^-$), bromine ion ($Br^-$), or an iodine ion ($I^-$). R" can also be carboxylic acid, citrate, oxalate, or any of the chalcogens such as oxygen ($O_2$) or sulfur ($S_2$). R" can also be a sulfite, sulfate, nitrite, or nitrate. R" can also be modified using nucleophilic acyl substitution reactions where an acetoxy group acts as a leaving group, allowing another nucleophile to attack and replace it, effectively changing the functional group attached to the oxygen atom; this is commonly achieved through hydrolysis to remove the acetyl group, or by reacting with other nucleophiles like amines or thiols to introduce different functionalities. Thereafter an amine or thiol group can be substituted or unsubstituted and there can be one substituent or more than one substituent that includes an alkyl, alkylaryl, alkene, amine, or any functional group that can normally be added via acyl substitution. In another embodiment R' and R" can the same or R' and R" be different and chosen from any of the groups above.

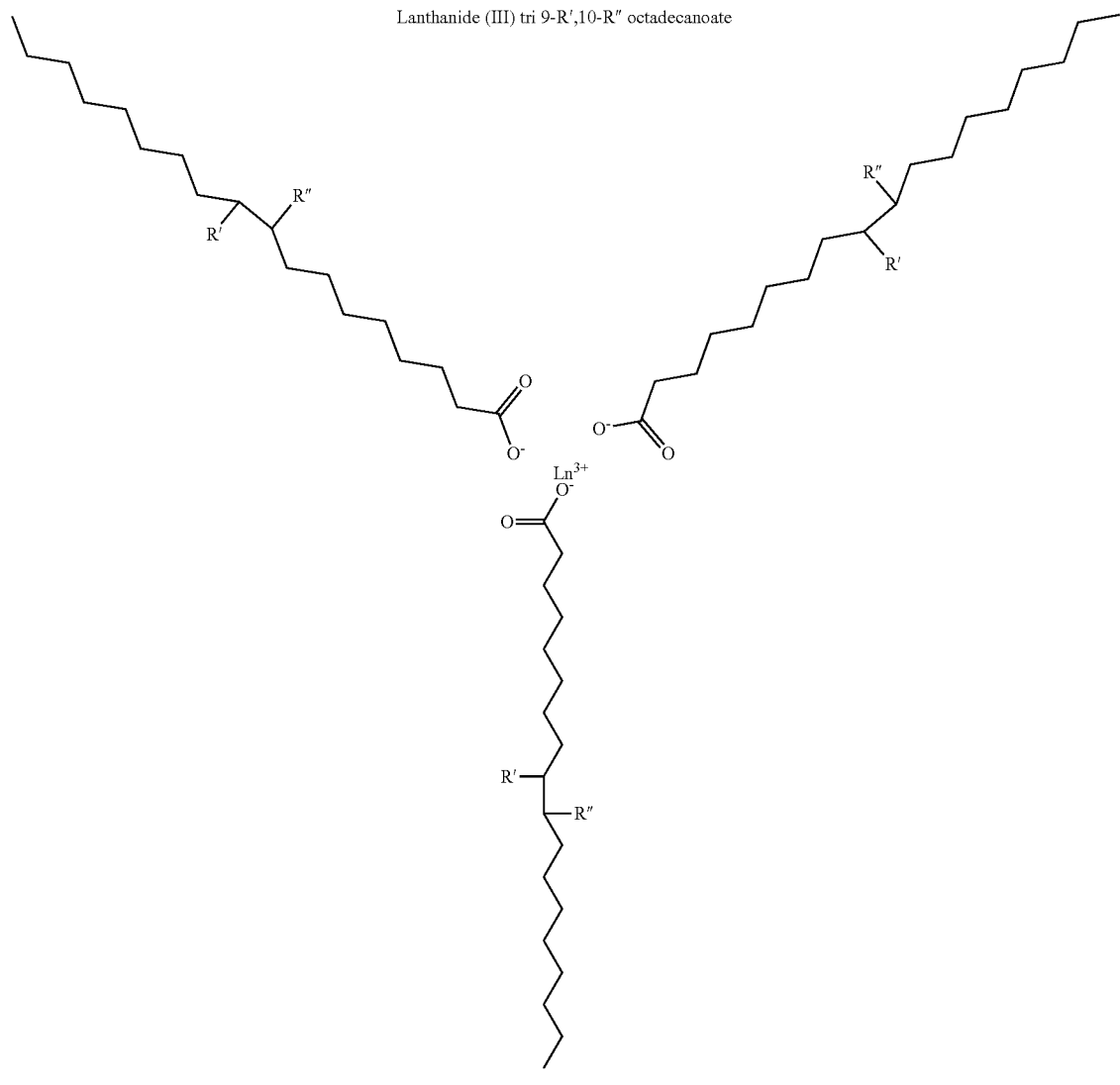

Formula 25

Lanthanide (III) tri 9-R',10-R" octadecanoate

Controlled Release Formulation Composition

According to one embodiment, described herein is a composition comprising a lanthanide (III) 9-R', 10-R" octadecanoate compound. In some embodiments, the composition may be used for therapeutic methods. In some embodiments, the composition comprising a lanthanide (III) 9-R', 10-R" octadecanoate compound is a controlled release formulation.

The lanthanide (III) 9-R', 10-R" octadecanoate compound may be combined or coordinately administered with a suitable carrier or vehicle depending on the route of administration. The term "pharmaceutically acceptable carrier" refers to a carrier that is conventionally used in the art to facilitate the storage, administration, and/or the healing effect of an active agent of a pharmaceutical composition.

In some embodiments, at least one pharmaceutically acceptable carrier in the formulation may be an emulsion comprising gum Arabic, guar gum, carrageenan, sodium phosphate or a derivative thereof, and a titanium oxide. The pharmaceutically acceptable carrier in the formulation may comprise a solution that may contain excipients, such as sodium chloride, citrate, and ethylenediamine tetraacetic acid (EDTA). The emulsion may serve as a carrier and also a release rate controlling agent in the formulation.

In some embodiments, at least one pharmaceutically acceptable carrier in the formulation may include at least one natural gum. Non-limiting examples of natural gums include agar, alginic acid, sodium alginate, carrageenan, gum Arabic, gum ghatti, gum tragacanth, karaya gum, guar gum, locust bean gum, beta-glucan, dammar gum, glucomannan, *psyllium* seed husks, tara gum, gellan gum and xanthan gum.

In some embodiments, at least one pharmaceutically acceptable carrier in the formulation may include gum Arabic, which may optionally be included an amount of 1% to 60% (w/w) and which may serve as a carrier and also a release rate controlling agent in the formulation. In some embodiments, at least one pharmaceutically acceptable carrier in the formulation may include guar gum, which may optionally be included an amount of 1% to 60% (w/w) and which may serve as a carrier and also a release rate controlling agent in the formulation. In some embodiments, at least one pharmaceutically acceptable carrier in the formulation may include carrageenan, which may optionally be included an amount of 1% to 60% (w/w) and which may serve as a carrier and also a release rate controlling agent in the formulation.

In some embodiments, the at least one pharmaceutically acceptable carrier may include at least one iron salt. Suitable iron excipients are disclosed, for example, in U.S. Patent Application No. 2022-0016312, which is incorporated herein by reference in its entirety. In some embodiments, the at least one iron salt may include ferric sulfate, such as Fe(II) or Fe(III) sulfate, which may be present from 0% to 15% (w/w) and provides stability to the carrier.

In some embodiments, the at least one pharmaceutically acceptable carrier may include at least one titanium salt. Suitable titanium salts are disclosed, for example, titanium oxide. In some embodiments, the at least one titanium salt excipient may include titanium oxide which may optionally be present from 0% to 15% (w/w) and which may provide color, stability and also contrast when imaging using computed tomographic imaging (CT).

In some embodiments, the at least one pharmaceutically acceptable carrier may include at least one sodium phosphate salt. Suitable sodium phosphate salts include sodium phosphate dibasic, sodium phosphate monobasic, and sodium phosphate dibasic dihydrate. In some embodiments, the at least one sodium phosphate salt may include sodium phosphate dibasic which may optionally be present from 0% to 20% (w/w) and which serves a release rate controlling agent.

In some embodiments, the at least one pharmaceutically acceptable carrier may include guar gum, gum Arabic, a carrageenan, sodium phosphate dibasic, and titanium oxide.

Examples of suitable biocompatible polymers include hyaluronic acid, collagen, tricalcium phosphate, chondroitin sulfate, polybutyrate, polylactide, polyglycolide, and lactide/glycolide copolymers, and mixtures or copolymers thereof. Suitable carriers also include on-polymer systems such as carboxylic acids, fatty acids, phospholipids, amino acids, lipids such as sterols, hydrogel release system; silastic system; peptide-based system; implants and the like.

In one embodiment, the pharmaceutically acceptable carrier is a hygroscopic collagen-based carrier such as a collagen sponge, a collagen scaffold, a powdered collagen, or a collagen-based gelatin hydrogel.

In another embodiment, the one pharmaceutically acceptable carrier is a hydrophilic hydrogel-based carrier (e.g., poly lactic acid, poly glycolic acid), which allows for release over a period of time.

In another embodiment, the one pharmaceutically acceptable carrier comprises a tri-block co-polymer comprising a central block of PLA (poly-(lactic acid) flanked by two blocks of PEG-(poly-(ethylene glycol).

In still another embodiment, the pharmaceutically acceptable carrier comprises albumin, a derivative or fragment of albumin that maintains the N-allyl noroxymorphone binding site located at the interface between the IA and IIA domains, and/or maintains the N-allyl noroxymorphone binding site around tryptophan (Trp)-214, that binds an OGFR antagonist such as N-allyl noroxymorphone or a functional derivative thereof and allows for a slow release of an OGFR antagonist.

In still another embodiment, the pharmaceutically acceptable carrier comprises a methyl cellulose, which forms an inert gel, for example, that binds an active compound and allows for a slow release of the active compound.

Suitable pharmaceutically acceptable carriers can be an emulsion, vesicle, micelle, nano-lipid particle, bead, microsphere or nanoparticle form, and can be made of natural and/or synthetic biocompatible polymers. Examples of suitable biocompatible polymers include hyaluronic acid, chondroitin sulfate, polybutyrate, polylactide, polyglycolide, and lactide/glycolide copolymers, and mixtures or copolymers thereof. Suitable carriers also include on-polymer systems such as carboxylic acids, phospholipids, amino acids, sterols, hydrogel release system; silastic system; peptide-based system; implants and the like.

In some embodiments, a pharmaceutically acceptable carrier is a composition disclosed herein that comprises one or more pharmaceutically acceptable compositions, such as an aqueous carrier or vehicle that includes acceptable buffers, and/or antioxidants.

In some embodiments, the pharmaceutically acceptable carrier comprise an ethanol (EtOH) based saline solution. In some embodiments, the pharmaceutically acceptable carrier comprises more than about 100-mM of the active compound in the ethanol based saline solution. In some embodiments, the pharmaceutically acceptable carrier comprises about 10-mM to about 150-mM of the active compound in the ethanol based saline solution. In some embodiments, the pharmaceutically acceptable carrier comprises about 20-mM to about 140-mM of the active compound in the ethanol based saline solution. In some embodiments, the pharmaceutically acceptable carrier comprises about 30-mM to about 130-mM of the active compound in the ethanol based saline solution. In some embodiments, the pharmaceutically acceptable carrier comprises about 40-mM to about 120-mM of active compound in the ethanol based saline solution. In some embodiments, the pharmaceutically acceptable carrier comprises about 50-mM to about 110-mM of the active compound in the ethanol based saline solution. In some embodiments, the pharmaceutically acceptable carrier comprises about 10-mM to about 110-mM of the active compound in the ethanol based saline solution. In some embodiments, the pharmaceutically acceptable carrier comprises more than 100-mM of the active compound in the ethanol based saline solution.

In some embodiments, the pharmaceutically acceptable carrier comprises an acidified saline-based solution that exhibits a pH from about 4.5 to about 7.4. In some embodiments, the acidified saline-based solution exhibits a pH from about 5.5 to about 7.4. In some embodiments, the acidified saline-based solution exhibits a pH from about 6.5 to about 7.4.

In some embodiments, the pharmaceutically acceptable carrier formulation comprises a diluent that is an ethanol based saline solution. In some embodiments, the ethanol based saline solution comprises from about 1% volume/volume (v/v) ethanol to about 80% v/v ethanol. In some embodiments, the ethanol based saline solution comprises from about 5% volume/volume (v/v) ethanol to about 80% v/v ethanol. In some embodiments, the ethanol based saline solution comprises from about 10% volume/volume (v/v) ethanol to about 80% v/v ethanol. In some embodiments, the ethanol based saline solution comprises from about 15% volume/volume (v/v) ethanol to about 80% v/v ethanol. In some embodiments, the ethanol based saline solution comprises from about 25% volume/volume (v/v) ethanol to about 80% v/v ethanol. In some embodiments, the ethanol based saline solution comprises from about 30% volume/volume (v/v) ethanol to about 80% v/v ethanol. In some embodiments, the ethanol based saline solution comprises from about 35% volume/volume (v/v) ethanol to about 80% v/v ethanol. In some embodiments, the ethanol based saline solution comprises from about 40% volume/volume (v/v) ethanol to about 80% v/v ethanol. In some embodiments, the ethanol based saline solution comprises from about 40% volume/volume (v/v) ethanol to about 70% v/v ethanol.

In some embodiments, the ethanol based saline solution comprises about 1% volume/volume (v/v) ethanol. In some embodiments, the ethanol based saline solution comprises about 2% volume/volume (v/v) ethanol. In some embodiments, the ethanol based saline solution comprises about 3% volume/volume (v/v) ethanol. In some embodiments, the ethanol based saline solution comprises about 4% volume/volume (v/v) ethanol. In some embodiments, the ethanol based saline solution comprises about 5% volume/volume (v/v) ethanol. In some embodiments, the ethanol based saline solution comprises about 6% volume/volume (v/v) ethanol. In some embodiments, the ethanol based saline solution comprises about 7% volume/volume (v/v) ethanol. In some embodiments, the ethanol based saline solution comprises about 8% volume/volume (v/v) ethanol. In some embodiments, the ethanol based saline solution comprises about 9% volume/volume (v/v) ethanol. In some embodiments, the ethanol based saline solution comprises about 10% volume/volume (v/v) ethanol. In some embodiments, the ethanol based saline solution comprises about 20% volume/volume (v/v) ethanol. In some embodiments, the ethanol based saline solution comprises about 30% volume/volume (v/v) ethanol. In some embodiments, the ethanol based saline solution comprises about 40% volume/volume (v/v) ethanol. In some embodiments, the ethanol based saline solution comprises about 50% volume/volume (v/v) ethanol. In some embodiments, the ethanol based saline solution comprises about 60% volume/volume (v/v) ethanol. In some embodiments, the ethanol based saline solution comprises about 70% volume/volume (v/v) ethanol. In some embodiments, the ethanol based saline solution comprises about 80% volume/volume (v/v) ethanol.

In some embodiments, the ethanol based saline solution comprises a phosphate buffered saline solution, a borate buffered saline solution, a Tris buffered saline solution, or a carbonate buffered saline solution.

In some embodiments, the saline solution comprises a salt and water. In some embodiments, the salt of the saline solution comprises sodium chloride or potassium chloride. In some embodiments, the saline solution comprises from about 0.7% w/w salt to about 1.5% w/w salt. In some embodiments, the saline solution comprises about 0.7% salt. In some embodiments, the saline solution comprises about 0.8% salt. In some embodiments, the saline solution comprises about 0.9% salt. In some embodiments, the saline solution comprises about 1.0% salt. In some embodiments, the saline solution comprises about 1.1% salt. In some embodiments, the saline solution comprises about 1.2% salt. In some embodiments, the saline solution comprises about 1.3% salt. In some embodiments, the saline solution comprises about 1.4% salt. In some embodiments, the saline solution comprises about 1.5% salt.

A water-containing liquid pharmaceutically acceptable carrier can comprise pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories can be found in the U.S. Pharmacopeia National Formulary, 1857-1859, and (1990). Some examples of the materials which can serve as pharmaceutically acceptable carrier are sugars, such as lactose, glucose and sucrose; cyclodextrins, including alpha-cyclodextrin, beta-cyclodextrin, and gamma-cyclodextrin; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents.

In some embodiments, the pharmaceutically acceptable carrier composition comprises preservatives and antioxidants. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

The pharmaceutically acceptable carrier compositions according to the invention may also comprise one or more binding agents, filling agents, lubricating agents, suspending agents, sweeteners, preservatives, buffers, wetting agents, disintegrants, effervescent agents, and other excipients. Such excipients are known in the art. Examples of filling agents include lactose monohydrate, lactose anhydrous, and various starches; examples of binding agents include various celluloses and cross-linked polyvinylpyrrolidone, microcrystalline cellulose such as Avicel™, PH101 microcrystalline cellulose and/or Avicel™, PH102 microcrystalline cellulose, and silicified microcrystalline cellulose such as ProSolv SMCC™. Suitable lubricants, including agents that act on the flow-ability of the powder to be compressed, may include colloidal silicon dioxide such as Aerosil® 200 (colloidal silicon dioxide), talc, stearic acid, magnesium stearate, calcium stearate, and silica gel. Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Any pharmaceutically acceptable carrier formulation used for therapeutic administration can be sterile. Sterility is readily accomplished by for example filtration through sterile filtration membranes (e.g., 0.2-micron membranes). Any pharmaceutically acceptable sterilization method can be used in the formulation.

Routes of Administration

The pharmaceutically acceptable carrier composition comprising a lanthanide (III) tri 9-R', 10-R" octadecanoate compound will be formulated and dosed in a fashion consistent with good medical practice, taking into account the clinical condition of the individual patient, the method of administration, the scheduling of administration, and other factors known to those in the art.

A variety of administration routes are available. The pharmaceutical composition of the invention may be practiced using any mode of administration that is medically acceptable, meaning any mode that produces effective levels of the active ingredients without causing clinically unacceptable adverse effects. Accordingly, the pharmaceutical compositions can be administered to a subject parenterally, intraperitoneally, transdermally, intramuscularly, intratumorally, subcutaneously, intra-adiposally, intra-articularly, or intrathecally.

Modes of administration include topical, intradermal, or parenteral routes. The term "parenteral" includes subcutaneous, percutaneous, intravenous, intramuscular, or infusion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's solution or fixed 25 oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In some embodiments, the controlled release formulation may be administered locally to a site (e.g., intratumorally, peritumorally, or perilesionally), such as a site of a primary cancer lesion or a metastatic cancer lesion, in a subject via percutaneous injection, any minimally invasive procedure, or via laparoscopy. The controlled release formulation may be such that it does not dissipate from the site of percutaneous injection. The act of local administering such as percutaneous injection to the site, such as the site of a primary cancer lesion or a metastatic cancer lesion, may be repeated for as long is tolerable to the patient and effective for reducing tumor, including but not limited to at least one additional time, or at least two time, or at least three times, or at least four times, or at least five times, or at least six times, or at least seven times, or at least eight times, or at least nine times, or at least ten times, or at least eleven times, or at least twelve times, or at least thirteen times, or at least fourteen times, or at least fifteen times, or at least sixteen times, or at least seventeen times, or at least eighteen times, or at least nineteen times, or at least twenty times.

In some embodiments, the pharmaceutically acceptable carrier composition is administered in a volume that may be from about 0.1-cubic centimeter (cc) to about 20-cc, from about 0.25-cc to about 15-cc, from about 0.5-cc to about 10-cc, from about 1-cc to about 10-cc, from about 2-cc to about 10-cc. The corresponding amount of the Lanthanide (III) 9-R', 10-R" octadecanoate compound in the carrier may be from about 10-ng per cc, 20-ng per cc, 30-ng per cc, 40-ng per cc, 50-ng per cc, 60-ng per cc, 70-ng per cc, 80-ng per cc, 90-ng per cc, 100-ng per cc, 200-ng per cc, 300-ng per cc, 400-ng per cc, 500-ng per cc, 600-ng per cc, 700-ng per cc, 800-ng per cc, 900-ng per cc, 1-µg per cc, 2-µg per cc, 3-µg per cc, 4-µg per cc, 5-µg per cc, 6-µg per cc, 7-µg per cc, 8-µg per cc, 9-µg per cc, and/or 10-µg per cc.

In some embodiments, the pharmaceutically acceptable carrier composition is a controlled release formulation that may be configured to release the lanthanide (III) 9-R', 10-R" octadecanoate compound over a period of 24-hours, 48-hours, 72-hours, 96-hours, 120-hours, 144-hours, 168-hours, 192-hours, 216-hours, 240-hours, 264-hours, 288-hours, 312-hours, 336-hours, 360-hours, 384-hours, 412-hour, 436-hours, 460-hours, 484-hours, and/or 508-hours. In a preferred embodiment, the pharmaceutically acceptable carrier composition is a controlled release formulation that may be configured to release the lanthanum (III) 9,10-diacetoxy octadecanoate compound in conjunction with or without an OGFR antagonist such as N-allyl noroxymorphone, a CDK4/6 inhibitor such as abemaciclib, and an estrogen inhibitor such as tamoxifen or elacestrant.

In some embodiments, the controlled release formulation possesses a particular level of flowability. In some embodiments, the control release formulation can pass through a 27-G, 25-G, 23-G, 22-G, 21-G, 18-G, 16-G, 14-G, and/or 13-G needle.

In a preferred embodiment, the pharmaceutically acceptable carrier composition is a controlled release formulation that may be configured to release the lanthanum (III) 9,10-diacetoxy octadecanoate compound in conjunction with or without an OGFR antagonist such as N-allyl noroxymorphone, a CDK4/6 inhibitor such as abemaciclib, and an estrogen inhibitor such as tamoxifen or elacestrant as part of a controlled release formulation that is administered to a patient with a cancer in a need thereof. In this preferred embodiment, the controlled release formulation will be administered intra-tumoral or peri-tumoral using loco-regional therapeutic administration methods, which include injection of the control release formulation via a needle, that in some embodiments could be an 18-G or 21-G needle attached to a syringe. In another preferred embodiment, the controlled release formulation is administered intra-tumoral or peri-tumoral using loco-regional approaches that include non-invasive diagnostic methods that includes ultrasound imaging, fluoroscopy imaging, computed tomographic imaging (CT), magnetic resonance imaging (MRI), or any variation or combination of these imaging techniques. Non-invasive imaging techniques can be used to administer the controlled release formulation or monitor tumor size following administration of an injection of the controlled release formulation. In another embodiment, the controlled release formulation is comprised of titanium salts and the lanthanum (III) 9,10-diacetoxy octadecanoate compound, both of which are visible under ultrasound, CT, and MRI imaging, or any combination or derivative thereof, including any MRI imaging algorithm, such T1-weighted, T2-weighted, or gradient recall echo. Acceptable imaging techniques will include the use of contrast agents, such as iohexol based contrast agents (e.g., Omnipaque 300) or gadolinium-based contrast agents.

The methods and compositions herein may be provided in the form of a kit. A "kit" is herein defined as a package and containing several individual parts that show a complementary effect when applied together. In this aspect, the effect achieved by a kit and the pharmaceutical composition are similar. The kit may optionally include instructions for using the pharmaceutical compositions.

Biologic Effects

In some embodiments, the anti-neoplastic and anti-cancer therapies are singularly administered. In some embodiments the anti-neoplastic and anti-cancer therapies are administered in combinations.

In some embodiments, the lanthanide (III) 9-R', 10-R" octadecanoate compound or the lanthanide (III) tridodeconoate, or the lanthanide (III) tripalmitate, or the lanthanide (III) tristearate and the OGFR antagonist N-allyl noroxymorphone act synergistically to reduce cell proliferation and increase cell death. In a preferred embodiment, the lanthanum (III) 9,10-diacetoxy octadecanoate compound and the OGFR antagonist N-allyl noroxymorphone act synergistically to reduce cell proliferation and increase cell death. This is accomplished via the N-allyl noroxymorphone antagonism of the p-opioid receptor (MOR) and antagonism of the OGFR. N-allyl noroxymorphone inhibition of MOR signaling leads to decreased MAPK/PI3K signaling (FIG. 1). In parallel, N-allyl noroxymorphone inhibition of OGFR signaling leads to increased p21 expression (FIG. 1). Thus, the synergistic decrease in MAPK/PI3K with increased p21 expression leads to decreased cell proliferation (FIG. 1). Independently, Lanthanum compounds also inhibit cellular metabolism via TRP channels in mitochondria, as well as the cell's outer membrane. Treatment with a lanthanum compound leads to a decrease in ATP, which in turn reduces cellular activity and further reduces cellular signaling, with many signaling pathways requiring ATP to function (FIG. 1).

In another embodiment, the lanthanide (III) 9-R', 10-R" octadecanoate compound or the lanthanide (III) tridodecanoate, or the lanthanide (III) tripalmitate, or the lanthanide (III) tristearate interact with cell membranes and are endocytosed. In a preferred embodiment (FIG. 2), the lanthanum (III) 9,10-diacetoxy octadecanoate compound incorporation with the cell membrane begins the process of endocytosis, which brings the Lanthanide (III) 9-R', 10-R" octadecanoate into the cell via the process of creating a vesicle that is transported into the cytoplasm. The endocytotic vesicle fuses with a lysosome, which releases acid and enzymes that degrade fatty acid molecules. Once degradation is complete, the endocytotic vesicle releases the contents, which includes lipid-peroxidase molecules that produce free radical oxygen species (ROS) that can subsequently damage other cell organelles. In addition, elemental $La^+$ can also block calcium channels resulting in decreased cellular activity.

EXAMPLES

The structure for the lanthanide (III) tridodeconoate compounds was assessed by carefully measuring the pre-reaction compounds weight and post-reaction compound weight (Table I). The hydration was carefully assessed by heating the lanthanide acetate salts to produce the anhydrate as well as published accounts of the hydrated lanthanide acetate salts. Lanthanum acetate is reacted with lauric acid when heated to at least 900 C according to the equation: $La(CH_3COO)_3 \cdot 3H_2O + 3(C_{12}H_{24}O_2) = La(C_{12}H_{23}O_2)_3 + 3(CH_3COOH) + 3H_2O$. This reaction produces lanthanum (III) tridodeconoate, which is a clear viscous material that forms a white waxy material upon cooling. Cerium acetate is reacted with lauric acid when heated to at least 900 C according to the equation: $Ce(CH_3COO)_3 \cdot 2H_2O + 3(C_{12}H_{24}O_2) = Ce(C_{12}H_{23}O_2)_3 + 3(CH_3COOH) + 2H_2O$. This reaction produces cerium (III) tridodeconoate, which is a clear orange/brown viscous material that forms an orange/brown waxy material upon cooling. Praseodymium acetate is reacted with lauric acid when heated to at least 900 C according to the equation: $Pr(CH_3COO)_3 \cdot 2H_2O + 3(C_{12}H_{24}O_2) = Pr(C_{12}H_{23}O_2)_3 + 3(CH_3COOH) + 2H_2O$. This reaction produces praseodymium (III) tridodeconoate, which is a clear green viscous material that forms a green waxy material upon cooling. Neodymium acetate is reacted with lauric acid when heated to at least 900 C according to the equation: $Nd(CH_3COO)_3 \cdot 3H_2O + 3(C_{12}H_{24}O_2) = Nd(C_{12}H_{23}O_2)_3 + 3(CH_3COOH) + 3H_2O$. This reaction produces neodymium (III) tridodeconoate, which is a clear blue/violet viscous material that forms a blue/violet waxy material upon cooling. Gadolinium acetate is reacted with lauric acid when heated to at least 900 C according to the equation: $Gd(CH_3COO)_3 \cdot 3H_2O + 3(C_{12}H_{24}O_2) = Gd(C_{12}H_{23}O_2)_3 + 3(CH_3COOH) + 3H_2O$. This reaction produces gadolinium (III) tridodeconoate, which is a clear viscous material that forms a white waxy material upon cooling. Terbium acetate is reacted with lauric acid when heated to at least 900 C according to the equation: $Tb(CH_3COO)_3 \cdot 2H_2O + 3(C_{12}H_{24}O_2) = Tb(C_{12}H_{23}O_2)_3 + 3(CH_3COOH) + 2H_2O$. This reaction produces terbium (III) tridodeconoate, which is a clear viscous material that forms a white waxy material upon cooling. The post-reaction compound weight was in good agreement with the hypothetical loss of weight due to lost water and acetic acid (Table I).

TABLE I

| | Lanthanide | | | | | Lauric Acid | | | |
|---|---|---|---|---|---|---|---|---|---|
| | Quantity | Mol Wt. | Mols | Number of Lanthanide Molecules | Number Acetic Acid Molecules | Quantity | Mol Wt. | Mols | Number of Lauric Acid Molecules |
| Lanthanum Acetate | 1.118 | 316.04 | 0.00353753 | 2.13E+21 | 6.39E+21 | 2.126 | 200.32 | 0.010613 | 6.39E+21 |
| Cerium Acetate | 1.146 | 317.25 | 0.00361229 | 2.18E+21 | 6.53E+21 | 1.025 | 200.32 | 0.005117 | 6.53E+21 |
| Praseodymium Acetate | 1.102 | 318.04 | 0.00346497 | 2.09E+21 | 6.26E+21 | 0.98 | 200.32 | 0.004892 | 6.26E+21 |
| Neodymium Acetate | 1.183 | 321.37 | 0.00368112 | 2.22E+21 | 6.65E+21 | 1.04 | 200.32 | 0.005192 | 6.65E+21 |
| Gadolinium Acetate | 1.177 | 334.38 | 0.00351995 | 2.12E+21 | 6.36E+21 | 0.995 | 200.32 | 0.004967 | 6.36E+21 |
| Terbium Acetate | 1.059 | 336.06 | 0.00315122 | 1.90E+21 | 5.69E+21 | 0.89 | 200.32 | 0.004443 | 5.69F+21 |

TABLE I-continued

|  | | Acetic Acid | | | |
| --- | --- | --- | --- | --- | --- |
|  | Number Acetic Acid Molecules | Mol Wt. | Quantity | Pre-Reaction Weight | Post-Reaction Weight |
| Lanthanum Acetate | 6.39E+21 | 59.052 | 0.627 | 3.244 | 2.617 |
| Cerium Acetate | 6.53E+21 | 59.052 | 0.64 | 2.171 | 1.531 |
| Praseodymium Acetate | 6.26E+21 | 59.052 | 0.614 | 2.082 | 1.468 |
| Neodymium Acetate | 6.65E+21 | 59.052 | 0.652 | 2.223 | 1.571 |
| Gadolinium Acetate | 6.36E+21 | 59.052 | 0.624 | 2.172 | 1.548 |
| Terbium Acetate | 5.69E+21 | 59.052 | 0.558 | 1.949 | 1.391 |

The structure for the lanthanide (III) tripalmitate compounds was assessed by carefully measuring the pre-reaction compounds weight and post-reaction compound weight (Table II). Lanthanum acetate is reacted with palmitic acid when heated to at least 1800 C according to the equation: $La(CH_3COO)_3 \cdot 3H_2O + 3(C_{16}H_{32}O_2) = La(C_{16}H_{31}O_2)_3 + 3(CH_3COOH) + 3H_2O$. This reaction produces lanthanum (III) tripalmitate, which is a clear viscous material that forms a white waxy material upon cooling. Cerium acetate is reacted with palmitic acid when heated to at least 180° C. according to the equation: $Ce(CH_3COO)_3 \cdot 2H_2O + 3(C_{16}H_{32}O_2) = Ce(C_{16}H_{31}O_2)_3 + 3(CH_3COOH) + 2H_2O$. This reaction produces cerium (III) tripalmitate, which is a clear orange/brown viscous material that forms an orange/brown waxy material upon cooling. Praseodymium acetate is reacted with palmitic acid when heated to at least 1800 C according to the equation: $Pr(CH_3COO)_3 \cdot 2H_2O + 3(C_{16}H_{32}O_2) = Pr(C_{16}H_{31}O_2)_3 + 3(CH_3COOH) + 2H_2O$. This reaction produces praseodymium (III) tripalmitate, which is a clear green viscous material that forms a green waxy material upon cooling. Neodymium acetate is reacted with palmitic acid when heated to at least 180° C. according to the equation: $Nd(CH_3COO)_3 \cdot 3H_2O + 3(C_{16}H_{32}O_2) = Nd(C_{16}H_{31}O_2)_3 + 3(CH_3COOH) + 3H_2O$. This reaction produces neodymium (III) tripalmitate, which is a clear blue/violet viscous material that forms a blue/violet waxy material upon cooling. Gadolinium acetate is reacted with palmitic acid when heated to at least 1800 C according to the equation: $Gd(CH_3COO)_3 \cdot 3H_2O + 3(C_{16}H_{32}O_2) = Gd(C_{16}H_{31}O_2)_3 + 3(CH_3COOH) + 3H_2O$. This reaction produces gadolinium (III) tripalmitate, which is a clear viscous material that forms a white waxy material upon cooling. Terbium acetate is reacted with palmitic acid when heated to at least 180° C. according to the equation: $Tb(CH_3COO)_3 \cdot 2H_2O + 3(C_{16}H_{32}O_2) = Tb(C_{16}H_{31}O_2)_3 + 3(CH_3COOH) + 2H_2O$. This reaction produces terbium (III) tripalmitate, which is a clear viscous material that forms a white waxy material upon cooling. The post-reaction compound weight was in good agreement with the hypothetical loss of weight that was due to lost water and the loss of acetic acid (Table II).

TABLE II

|  | Lanthanide | | | | | Palmitic Acid | | | |
| --- | --- | --- | --- | --- | --- | --- | --- | --- | --- |
|  | Quantity | Mol Wt. | Mols | Number of Lanthanide Molecules | Number Acetic Acid Molecules | Quantity | Mol Wt. | Mols | Number of Lauric Acid Molecules |
| Lanthanum Acetate | 1.118 | 316.04 | 0.00353753 | 2.13E+21 | 6.39E+21 | 2.721 | 256.42 | 0.010613 | 6.39E+21 |
| Cerium Acetate | 1.146 | 317.25 | 0.00361229 | 2.18E+21 | 6.53E+21 | 1.025 | 256.42 | 0.003997 | 6.53E+21 |
| Praseodymium Acetate | 1.102 | 318.04 | 0.00346497 | 2.09E+21 | 6.26E+21 | 0.98 | 256.42 | 0.003822 | 6.26E+21 |
| Neodymium Acetate | 1.183 | 321.37 | 0.00368112 | 2.22E+21 | 6.65E+21 | 1.04 | 256.42 | 0.004056 | 6.65E+21 |
| Gadolinium Acetate | 1.177 | 334.38 | 0.00351995 | 2.12E+21 | 6.36E+21 | 0.995 | 256.42 | 0.00388 | 6.36E+21 |
| Terbium Acetate | 1.059 | 336.06 | 0.00315122 | 1.90E+21 | 5.69E+21 | 0.89 | 256.42 | 0.003471 | 5.69E+21 |

|  | Acetic Acid | | | | |
| --- | --- | --- | --- | --- | --- |
|  | Number Acetic Acid Molecules | Mol Wt. | Quantity | Pre-Reaction Weight | Post-Reaction Weight |
| Lanthanum Acetate | 6.39E+21 | 59.052 | 0.627 | 3.839 | 3.213 |
| Cerium Acetate | 6.53E+21 | 59.052 | 0.64 | 2.171 | 1.531 |
| Praseodymium Acetate | 6.26E+21 | 59.052 | 0.614 | 2.082 | 1.468 |
| Neodymium Acetate | 6.65E+21 | 59.052 | 0.652 | 2.223 | 1.571 |
| Gadolinium Acetate | 6.36E+21 | 59.052 | 0.624 | 2.172 | 1.548 |
| Terbium Acetate | 5.69E+21 | 59.052 | 0.558 | 1.949 | 1.391 |

The structure for the lanthanide (III) tristearate compounds was assessed by carefully measuring the pre-reaction compounds weight and post-reaction compound weight (Table III). Lanthanum acetate is reacted with stearic acid when heated to at least 2250 C according to the equation: $La(CH_3COO)_3 \cdot 3H_2O + 3(C_{18}H_{36}O_2) = La(C_{18}H_{33}O_2)_3 + 3(CH_3COOH) + 3H_2O$. This reaction produces lanthanum (III) tripstearate, which is a clear viscous material that forms a white waxy material upon cooling. Cerium acetate is reacted with stearic acid when heated to at least 225° C. according to the equation: $Ce(CH_3COO)_3 \cdot 2H_2O + 3(C_{18}H_{36}O_2) = Ce(C_{18}H_{33}O_2)_3 + 3(CH_3COOH) + 2H_2O$. This reaction produces cerium (III) tristearate, which is a clear orange/brown viscous material that forms an orange/brown waxy material upon cooling. Praseodymium acetate is reacted with stearic acid when heated to at least 225° C. according to the equation: $Pr(CH_3COO)_3 \cdot 2H_2O + 3(C_{18}H_{36}O_2) = Pr(C_{18}H_{33}O_2)_3 + 3(CH_3COOH) + 2H_2O$. This reaction produces praseodymium (III) tristearate, which is a clear green viscous material that forms a green waxy material upon cooling. Neodymium acetate is reacted with stearic acid when heated to at least 225° C. according to the equation: $Nd(CH_3COO)_3 \cdot 3H_2O + 3(C_{18}H_{36}O_2) = Nd(C_{18}H_{33}O_2)_3 + 3(CH_3COOH) + 3H_2O$. This reaction produces neodymium (III) tristearate, which is a clear blue/violet viscous material that forms a blue/violet waxy material upon cooling. Gadolinium acetate is reacted with stearic acid when heated to at least 225° C. according to the equation: $Gd(CH_3COO)_3 \cdot 3H_2O + 3(C_{18}H_{36}O_2) = Gd(C_{18}H_{33}O_2)_3 + 3(CH_3COOH) + 3H_2O$. This reaction produces gadolinium (III) tripstearate, which is a clear viscous material that forms a white waxy material upon cooling. Terbium acetate is reacted with stearic acid when heated to at least 225° C. according to the equation: $Tb(CH_3COO)_3 \cdot 2H_2O + 3(C_{18}H_{36}O_2) = Tb(C_{18}H_{33}O_2)_3 + 3(CH_3COOH) + 2H_2O$.

This reaction produces terbium (III) tristearate, which is a clear viscous material that forms a white waxy material upon cooling. The post-reaction compound weight was in good agreement with the hypothetical loss of weight that was due to lost water and the loss of acetic acid (Table III).

The structure for the lanthanide (III) tri 9-R', 10-R''' octadecanoate compounds was assessed by carefully measuring the pre-reaction compounds weight and post-reaction compound weight (Table IV). Lanthanum acetate is reacted with oleic acid when heated to at least 270° C. according to the equation: $La(CH_3COO)_3 \cdot 3H_2O + 3(C_{18}H_{34}O_2) = La[(C_{18}H_{33}O_2) \cdot (CH_3COO)_2]_3 + CH_3COOH + 3H_2O$. During this reaction lanthanum (III) oleate forms, which results in the production of the following transient reaction products: First, hydrogen ions ($H^+$) displaced from each oleic acid molecule by the lanthanum (III) react with excess water to form three hydronium ions ($H_3O^+$). Two of the three ethanoate ions ($CH_3COO^-$) donated by the lanthanum (III) acetate reduce the unsaturated bond in oleic acid while the hydronium ions donate a hydrogen ion to the remaining ethanoate ion to produce acetic acid, with any remaining water/hydronium ions turning to vapor due to boiling. This reaction produces lanthanum (III) tri 9,10-diacetoxy octadecanoate, which is a clear viscous clear resinous material upon cooling. Cerium acetate is reacted with oleic acid when heated to at least 270° C. according to the equation: $Ce(CH_3COO)_3 \cdot 2H_2O + 3(C_{18}H_{34}O_2) = Ce[(C_{18}H_{33}O_2) \cdot (CH_3COO)_2]_3 + CH_3COOH + 2H_2O$. During this reaction cerium (III) oleate forms, which results in the production of the following transient reaction products: First, hydrogen ions ($H_5$) displaced from each oleic acid molecule by the cerium (III) react with excess water to form three hydronium ions ($H_3O^+$). Two of the three ethanoate ions ($CH_3COO^-$) donated by the cerium (III) acetate reduce the unsaturated bond in oleic acid while the hydronium ions donate a hydrogen ion to the remaining ethanoate ion to produce acetic acid, with any remaining water/hydronium ions turning to vapor due to boiling. This reaction produces cerium (III) tri 9,10-diacetoxy octadecanoate, which is a clear orange/brown viscous material that forms a clear orange/brown resinous material upon cooling. Praseodymium acetate is reacted with oleic acid when heated to at least 270° C. according to the equation: $Pr(CH_3COO)_3 \cdot 2H_2O + 3(C_{18}H_{34}O_2) = Pr[(C_{18}H_{33}O_2) \cdot (CH_3COO)_2]_3 + CH_3COOH + 2H_2O$. During this reaction praseodymium (III) oleate forms, which results in the production of the following transient reaction products: First, hydrogen ions ($H^+$) displaced from each oleic acid molecule by the praseodymium (III) react with excess water to form three hydronium ions

TABLE III

| | Lanthanide | | | | | Stearic Acid | | | |
| --- | --- | --- | --- | --- | --- | --- | --- | --- | --- |
| | Quantity | Mol Wt. | Mols | Number of Lanthanide Molecules | Number Acetic Acid Molecules | Quantity | Mol Wt. | Mols | Number of Lauric Acid Molecules |
| Lanthanum Acetate | 1.118 | 316.04 | 0.00353753 | 2.13E+21 | 6.39E+21 | 3.019 | 284.5 | 0.010613 | 6.39E+21 |
| Cerium Acetate | 1.146 | 317.25 | 0.00361229 | 2.18E+21 | 6.53E+21 | 1.025 | 284.5 | 0.003603 | 6.53E+21 |
| Praseodymium Acetate | 1.102 | 318.04 | 0.00346497 | 2.09E+21 | 6.26E+21 | 0.98 | 284.5 | 0.003445 | 6.26E+21 |
| Neodymium Acetate | 1.183 | 321.37 | 0.00368112 | 2.22E+21 | 6.65E+21 | 1.04 | 284.5 | 0.003656 | 6.65E+21 |
| Gadolinium Acetate | 1.177 | 334.38 | 0.00351995 | 2.12E+21 | 6.36E+21 | 0.995 | 284.5 | 0.003497 | 6.36E+21 |
| Terbium Acetate | 1.059 | 336.06 | 0.00315122 | 1.90E+21 | 5.69E+21 | 0.89 | 284.5 | 0.003128 | 5.69E+21 |

| | Acetic Acid | | | | |
| --- | --- | --- | --- | --- | --- |
| | Number Acetic Acid Molecules | Mol Wt. | Quantity | Pre-Reaction Weight | Post-Reaction Weight |
| Lanthanum Acetate | 6.39E+21 | 59.052 | 0.627 | 4.137 | 3.511 |
| Cerium Acetate | 6.53E+21 | 59.052 | 0.64 | 2.171 | 1.531 |
| Praseodymium Acetate | 6.26E+21 | 59.052 | 0.614 | 2.082 | 1.468 |
| Neodymium Acetate | 6.65E+21 | 59.052 | 0.652 | 2.223 | 1.571 |
| Gadolinium Acetate | 6.36E+21 | 59.052 | 0.624 | 2.172 | 1.548 |
| Terbium Acetate | 5.69E+21 | 59.052 | 0.558 | 1.949 | 1.391 | placed from each oleic acid molecule by the praseodymium (III) react with excess water to form three hydronium ions ($H_3O^+$). Two of the three ethanoate ions ($CH_3COO^-$) donated by the praseodymium (III) acetate reduce the unsaturated bond in oleic acid while the hydronium ions donate a hydrogen ion to the remaining ethanoate ion to produce acetic acid, with any remaining water/hydronium ions turning to vapor due to boiling. This reaction produces praseodymium (III) tri 9,10-diacetoxy octadecanoate, which is a clear green viscous material that forms a clear green resinous material upon cooling. Neodymium acetate is reacted with oleic acid when heated to at least 2700 C according to the equation: $Nd(CH_3COO)_3 \cdot XH_2O + 3(C_{18}H_{34}O_2) = Nd[(C_{18}H_{33}O_2) \cdot (CH_3COO)_2]_3 + CH_3COOH + XH_2O$. During this reaction neodymium (III) oleate forms, which results in the production of the following transient reaction products: First, hydrogen ions ($H^+$) displaced from each oleic acid molecule by the neodymium (III) react with excess water to form three hydronium ions ($H_3O^+$). Two of the three ethanoate ions ($CH_3COO^-$) donated by the neodymium (III) acetate reduce the unsaturated bond in oleic acid while the hydronium ions donate a hydrogen ion to the remaining ethanoate ion to produce acetic acid, with any remaining water/hydronium ions turning to vapor due to boiling. This reaction produces neodymium (III) tri 9,10-diacetoxy octadecanoate, which is a clear blue/violet viscous material that forms a clear blue/violet resinous material upon cooling. Gadolinium acetate is reacted with oleic acid when heated to at least 270° C. according to the equation: $Gd(CH_3COO)_3 \cdot 3H_2O + 3(C_{18}H_{34}O_2) = Gd[(C_{18}H_{33}O_2) \cdot (CH_3COO)_2]_3 + CH_3COOH + 3H_2O$. During this reaction neodymium gadolinium (III) oleate forms, which results in the production of the following transient reaction products: First, hydrogen ions ($H^+$) displaced from each oleic acid molecule by the gadolinium (III) react with excess water to form three hydronium ions ($H_3O^+$). Two of the three ethanoate ions ($CH_3COO^-$) donated by the gadolinium (III) acetate reduce the unsaturated bond in oleic acid while the hydronium ions donate a hydrogen ion to the remaining ethanoate ion to produce acetic acid, with any remaining water/hydronium ions turning to vapor due to boiling. This reaction produces gadolinium (III) tri 9,10-diacetoxy octadecanoate, which is a clear viscous material that forms a clear resinous material upon cooling. Terbium acetate is reacted with oleic acid when heated to at least 2700 C according to the equation: $Tb(CH_3COO)_3 \cdot 2H_2O + 3(C_{18}H_{34}O_2) = Tb[(C_{18}H_{33}O_2) \cdot (CH_3COO)_2]_3 + CH_3COOH + 2H_2O$. During this reaction neodymium terbium (III) oleate forms, which results in the production of the following transient reaction products: First, hydrogen ions ($H^+$) displaced from each oleic acid molecule by the terbium (III) react with excess water to form three hydronium ions ($H_3O^+$). Two of the three ethanoate ions ($CH_3COO^-$) donated by the terbium (III) acetate reduce the unsaturated bond in oleic acid while the hydronium ions donate a hydrogen ion to the remaining ethanoate ion to produce acetic acid, with any remaining water/hydronium ions turning to vapor due to boiling. This reaction produces terbium (III) tri 9,10-diacetoxy octadecanoate, which is a clear viscous material that forms a clear resinous material upon cooling. The post-reaction compound weight was in good agreement with the hypothetical loss of weight that was due to lost water and the loss of acetic acid (Table IV).

TABLE IV

| | Lanthanide | | | | Oleic Acid | | | |
|---|---|---|---|---|---|---|---|---|
| | Quantity | Mol Wt. | Mols | Number of Lanthanide Molecules | Number Acetic Acid Molecules | Quantity | Mol Wt. | Mols | Number of Lauric Acid Molecules |
| Lanthanum Acetate | 1.118 | 316.04 | 0.00353753 | 2.13E+21 | 6.39E+21 | 2.998 | 282.5 | 0.010613 | 6.39E+21 |
| Cerium Acetate | 1.146 | 317.25 | 0.00361229 | 2.18E+21 | 6.53E+21 | 1.025 | 282.5 | 0.003628 | 6.53E+21 |
| Praseodymium Acetate | 1.102 | 318.04 | 0.00346497 | 2.09E+21 | 6.26E+21 | 0.98 | 282.5 | 0.003469 | 6.26E+21 |
| Neodymium Acetate | 1.183 | 321.37 | 0.00368112 | 2.22E+21 | 6.65E+21 | 1.04 | 282.5 | 0.003681 | 6.65E+21 |
| Gadolinium Acetate | 1.177 | 334.38 | 0.00351995 | 2.12E+21 | 6.36E+21 | 0.995 | 282.5 | 0.003522 | 6.36E+21 |
| Terbium Acetate | 1.059 | 336.06 | 0.00315122 | 1.90E+21 | 5.69E+21 | 0.89 | 282.5 | 0.00315 | 5.69E+21 |

| | Acetic Acid | | | | |
|---|---|---|---|---|---|
| | Number Acetic Acid Molecules | Mol Wt. | Quantity | Pre-Reaction Weight | Post-Reaction Weight |
| Lanthanum Acetate | 4.26E+21 | 59.052 | 0.418 | 4.116 | 3.698 |
| Cerium Acetate | 4.35E+21 | 59.052 | 0.427 | 2.171 | 1.744 |
| Praseodymium Acetate | 4.17E+21 | 59.052 | 0.409 | 2.082 | 1.673 |
| Neodymium Acetate | 4.43E+21 | 59.052 | 0.435 | 2.223 | 1.788 |
| Gadolinium Acetate | 4.24E+21 | 59.052 | 0.416 | 2.172 | 1.756 |
| Terbium Acetate | 3.80E+21 | 59.052 | 0.372 | 1.949 | 1.577 |

Absorbance Properties

Figure 3:
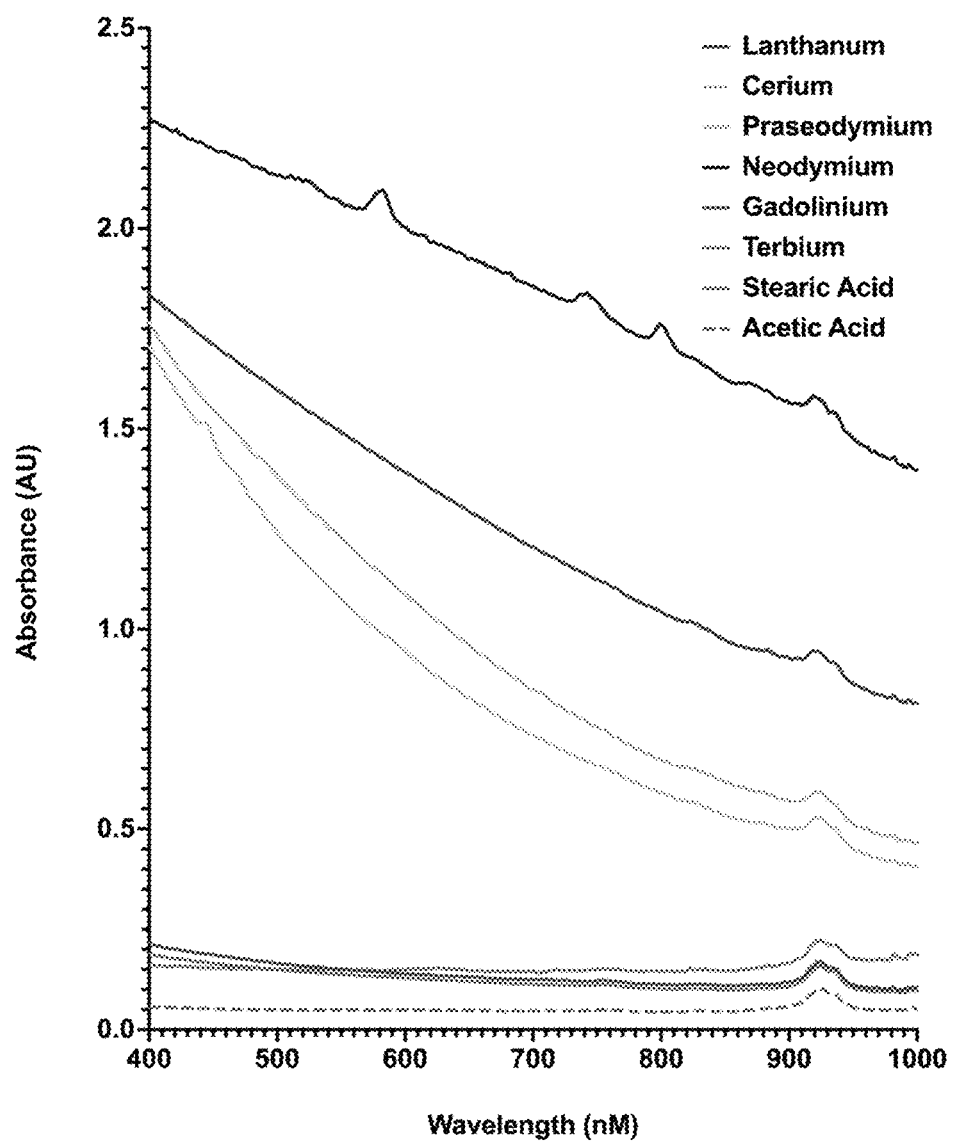
FIG. 3 shows absorbance spectrum for lanthanide (III) tristearate compounds.

The absorbance properties of lanthanum (III) tristearate, cerium (III) tristearate, praseodymium (III) tristearate, neodymium (III) tristearate, gadolinium (III) tristearate, and terbium (III) tristearate were evaluated on a Tecan monochrometer (FIG. 3) using a frequency sweep algorithm from 400-nm to 1000-nm. Lanthanide (III) tristearate compounds were solubilized in cyclohexane heated to 90° C. The lanthanide (III) tristearate cyclohexane solution was then diluted to 1-µg/mL. Similar concentrations of stearic acid and acetic acid were also evaluated. All of the lanthanide (III) tristearates were different from one another and also from stearic acid. Neodymium (III) tristearate has peaks at 568-nm, 748-nm, 805-nm, and 925-nm. Praseodymium (III) tristearate has a peak at 454-nm. All of the tested samples had a peak at 910-nm to 960-nm.

Figure 4:
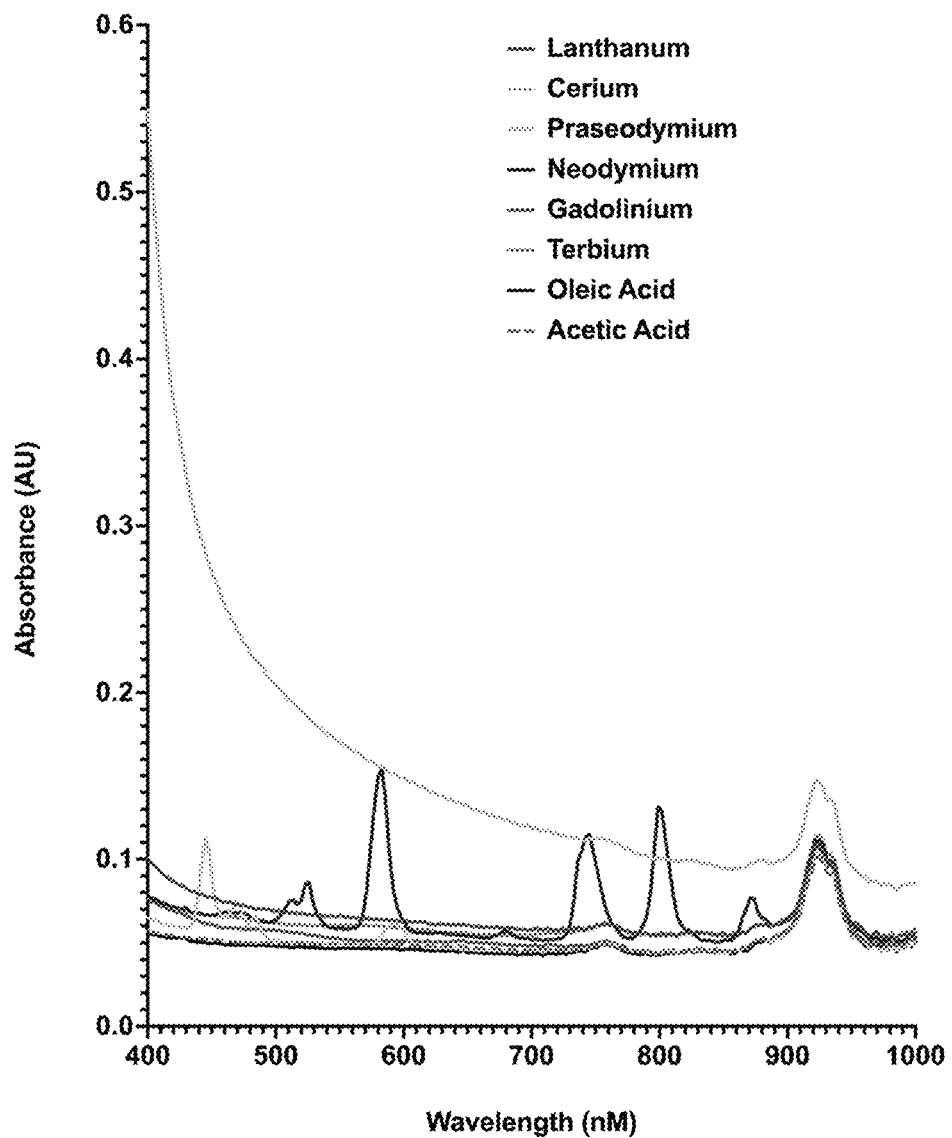
FIG. 4 shows absorbance spectrum for the lanthanide (III) tri 9,10-diacetoxy octadecanoate compounds.

The absorbance properties of lanthanum (III) tri 9,10-diacetoxy octadecanoate, cerium (III) tri 9,10-diacetoxy octadecanoate, praseodymium (III) tri 9,10-diacetoxy octadecanoate, neodymium (III) tri 9,10-diacetoxy octadecanoate, gadolinium (III) tristearate, and terbium (III) tri 9,10-diacetoxy octadecanoate were evaluated on a Tecan monochrometer (FIG. 4) using a frequency sweep algorithm from 400-nm to 1000-nm. Lanthanide (III) tri 9,10-diacetoxy octadecenoate compounds were solubilized in cyclohexane heated to 90° C. The lanthanide (III) tri 9,10-diacetoxy octadecenoate cyclohexane solution was then diluted to 1-μg/mL. Similar concentrations of oleic acid and acetic acid were also evaluated. All of the lanthanide (III) tri 9,10-diacetoxy octadecenoate were different from one another and also from oleic acid. Neodymium (III) tri 9,10-diacetoxy octadecenoate had peaks at 526-nm, 582-nm, 688-nm, 751-nm, 802-nm, and 874-nm. Praseodymium (III) tri 9,10-diacetoxy octadecenoate has a peak from 445-nm to 490-nm and a peak at 601-nm. All of the tested samples had a peak at 910-nm to 960-nm.

Method of creating an emulsion with the lanthanide (III) tri 9-R', 10-R" octadecanoate compounds In one embodiment, an emulsion can be formed from any of the lanthanide (III) tri 9-R', 10-R" octadecanoate compounds.

In a preferred embodiment, lanthanum (III) tri 9,10-diacetoxy octadecanoate is generated according to Table IV, which results in a final weight of 3.698-grams of lanthanide (III) tri 9-R', 10-R" octadecanoate. The lanthanum (III) tri 9,10-diacetoxy octadecanoate is then solubilized by heating with a suitable fatty acid, such as oleic acid or linoleic acid. In a preferred embodiment, the 3.698-grams of lanthanum (III) tri 9,10-diacetoxy octadecanoate was solubilized in 3.698-mL of oleic acid with heating >90° C. and continuous mixing, which results in a solution of 1-g/mL of lanthanum (III) tri 9,10-diacetoxy octadecanoate in an oleic acid solution (lanthanum (III) tri 9,10-diacetoxy octadecanoate/oleic acid solution).

In another embodiment, the lanthanum (III) tri 9,10-diacetoxy octadecanoate/oleic acid solution (1-g/mL) is added to a polysaccharide solution. The polysaccharide solution is comprised of gum Arabic, guar gum, and carrageenan solubilized in hot water. In a preferred embodiment, the following are added slowly to hot water: 1% (w/v) gum Arabic, 1% (w/v) guar gum, and 1% (w/v) carrageenan. In another preferred embodiment, the following are added slowly to hot water: 1% (w/v) gum Arabic, 1% (w/v) guar gum, 1% (w/v) carrageenan, and 1% (w/v) sodium alginate.

In another preferred embodiment, the following are added slowly to hot water such that the final concentration is between 0.1% (w/v) and 2% (w/v) for gum Arabic, 0.1% (w/v) and 2% (w/v) for guar gum, 0.1% (w/v) and 2% (w/v) for carrageenan, and 0.1% (w/v) and 2% (w/v) for sodium alginate.

In another embodiment, a saline-phosphate solution is added to the polysaccharide solution. The saline-phosphate solution comprises sodium phosphate, titanium oxide, citric acid monohydrate, acetic acid, and ethanol. In a preferred embodiment, the saline-phosphate solution is comprised of between 50% (w/w) to 99% (w/w) 0.9% saline solution, or between 0.1% (w/w) and 9% (w/w) of citric acid monohydrate, or between 0.1% (w/w) and 29.7% (w/w) sodium phosphate dibasic, or between 0.1% (w/w) and 37.1% (w/w) of titanium oxide, or between 0.1% (w/w) and 10% acetic acid, or between 0.1% (w/w) and 10% (w/w) ethanol, or between 0.1% (w/w) and 10% (w/w) glycerol. In another preferred embodiment, the saline-phosphate is comprised of 90.2% (w/w) saline solution, or 0.9% (w/w) of citric acid monohydrate, or 2.97% (w/w) sodium phosphate dibasic, or 3.71% (w/w) of titanium oxide, or 5% acetic acid, or 4.8% (w/w) ethanol, or 0.5% (w/w) glycerol. In another embodiment, the saline-phosphate solution is added to the polysaccharide solution. In a preferred embodiment, the saline-phosphate solution is added to the polysaccharide solution in the following ratios: 1 part saline-phosphate solution in 1 part polysaccharide solution, 1 part saline-phosphate solution in 2 parts polysaccharide solution, 1 part saline-phosphate solution in 3 parts polysaccharide solution, 1 part saline-phosphate solution in 4 parts polysaccharide solution, 1 part saline-phosphate solution in 5 parts polysaccharide solution, 1 part saline-phosphate solution in 6 parts polysaccharide solution, 1 part saline-phosphate solution in 7 parts polysaccharide solution, 1 part saline-phosphate solution in 8 parts polysaccharide solution, 1 part saline-phosphate solution in 9 parts polysaccharide solution, 1 part saline-phosphate solution in 10 parts polysaccharide solution, 1 part saline-phosphate solution in 11 parts polysaccharide solution, 1 part saline-phosphate solution in 12 parts polysaccharide solution, 1 part saline-phosphate solution in 13 parts polysaccharide solution, 1 part saline-phosphate solution in 14 parts polysaccharide solution, 1 part saline-phosphate solution in 15 parts polysaccharide solution, 1 part saline-phosphate solution in 16 parts polysaccharide solution, 1 part saline-phosphate solution in 17 parts polysaccharide solution, 1 part saline-phosphate solution in 18 parts polysaccharide solution, 1 part saline-phosphate solution in 19 parts polysaccharide solution, 1 part saline-phosphate solution in 20 parts polysaccharide solution. In a preferred embodiment, the polysaccharide/saline-phosphate solution would comprise 2 parts saline-phosphate solution in 8 parts polysaccharide solution. In another embodiment, the lanthanum (III) tri 9,10-diacetoxy octadecanoate/oleic acid solution is added to the polysaccharide/saline-phosphate solution.

In a preferred embodiment the following volumes of the lanthanum (III) tri 9,10-diacetoxy octadecanoate/oleic acid solution is added to the polysaccharide/saline-phosphate solution: 10-μL, 20-μL, 30-μL, 40-μL, 50-μL, 60-μL, 70-μL, 80-μL, 90-μL, 100-μL, 110-μL, 120-μL, 130-ρL, 140-μL, 150-μL, 160-μL, 170-μL, 180-μL, 190-μL, 200-μL, 210-μL, 220-μL, 230-μL, 240-ρL, 250-μL, 260-μL, 270-μL, 280-μL, 290-μL, 300-μL, 310-μL, 320-μL, 330-μL, 340-μL, 350-ρL, 360-μL, 370-μL, 380-μL, 390-μL, 400-μL, 410-μL, 420-μL, 430-μL, 440-μL, 450-μL, 460-ρL, 470-μL, 480-μL, 490-μL, 500-μL, 510-μL, 520-μL, 530-μL, 540-μL, 550-μL, 560-μL, 570-ρL, 580-μL, 590-μL, 600-μL, 610-μL, 620-μL, 630-μL, 640-μL, 650-μL, 660-μL, 670-μL, 680-ρL, 690-μL, 700-μL, 710-μL, 720-μL, 730-μL, 740-μL, 750-μL, 760-μL, 770-μL, 780-μL, 790-ρL, 800-μL, 810-μL, 820-μL, 830-μL, 840-μL, 850-μL, 860-μL, 870-μL, 880-μL, 890-μL, 900-ρL, 910-μL, 920-μL, 930-μL, 940-μL, 950-μL, 960-μL, 970-μL, 980-μL, 990-μL, or 1000-μL.

In another preferred embodiment, the lanthanum (III) tri 9,10-diacetoxy octadecanoate/oleic acid solution is added to the polysaccharide/saline-phosphate solution such that the final concentration is 100-ng/mL lanthanum (III) tri 9,10-diacetoxy octadecanoate/oleic acid solution, or 200-ng/mL of the lanthanum (III) tri 9,10-diacetoxy octadecanoate/oleic acid solution, or 300-ng/mL of the lanthanum (III) tri 9,10-diacetoxy octadecanoate/oleic acid solution, or 400-ng/mL of the lanthanum (III) tri 9,10-diacetoxy octadecanoate/oleic acid solution, or 500-ng/mL of the lanthanum (III) tri 9,10-diacetoxy octadecanoate/oleic acid solution, or 600-ng/mL of the lanthanum (III) tri 9,10-diacetoxy octadecanoate/oleic acid solution, or 700-ng/mL of the lanthanum (III) tri 9,10-diacetoxy octadecanoate/oleic acid solution, or 800-ng/mL of the lanthanum (III) tri 9,10-diacetoxy octadecanoate/oleic acid solution, or 900-ng/mL of the lanthanum (III) tri 9,10-diacetoxy octadecanoate/oleic acid solution, or 1-μg/mL of the lanthanum (III) tri 9,10-diacetoxy octadecanoate/ oleic acid solution, 1-μg/mL of the lanthanum (III) tri 9,10-diacetoxy octadecanoate/oleic acid solution, 1-μg/mL of the lanthanum (III) tri 9,10-diacetoxy octadecanoate/oleic acid solution, 2-μg/mL of the lanthanum (III) tri 9,10-diacetoxy octadecanoate/oleic acid solution, 3-μg/mL of the lanthanum (III) tri 9,10-diacetoxy octadecanoate/oleic acid solution, 4-μg/mL of the lanthanum (III) tri 9,10-diacetoxy octadecanoate/oleic acid solution, 5-μg/mL of the lanthanum (III) tri 9,10-diacetoxy octadecanoate/oleic acid solution, 6-μg/mL of the lanthanum (III) tri 9,10-diacetoxy octadecanoate/oleic acid solution, 7-μg/mL of the lanthanum (III) tri 9,10-diacetoxy octadecanoate/oleic acid solution, 8-μg/mL of the lanthanum (III) tri 9,10-diacetoxy octadecanoate/oleic acid solution, 9-μg/mL of the lanthanum (III) tri 9,10-diacetoxy octadecanoate/oleic acid solution, 10-μg/mL of the lanthanum (III) tri 9,10-diacetoxy octadecanoate/oleic acid solution, 20-μg/mL of the lanthanum (III) tri 9,10-diacetoxy octadecanoate/oleic acid solution, 30-μg/mL of the lanthanum (III) tri 9,10-diacetoxy octadecanoate/oleic acid solution, 40-μg/mL of the lanthanum (III) tri 9,10-diacetoxy octadecanoate/oleic acid solution, 50-μg/mL of the lanthanum (III) tri 9,10-diacetoxy octadecanoate/oleic acid solution, 60-μg/mL of the lanthanum (III) tri 9,10-diacetoxy octadecanoate/oleic acid solution, 70-μg/mL of the lanthanum (III) tri 9,10-diacetoxy octadecanoate/oleic acid solution, 80-μg/mL of the lanthanum (III) tri 9,10-diacetoxy octadecanoate/oleic acid solution, 90-μg/mL of the lanthanum (III) tri 9,10-diacetoxy octadecanoate/oleic acid solution, 100-μg/mL of the lanthanum (III) tri 9,10-diacetoxy octadecanoate/oleic acid solution, 200-μg/mL of the lanthanum (III) tri 9,10-diacetoxy octadecanoate/oleic acid solution, 300-μg/mL of the lanthanum (III) tri 9,10-diacetoxy octadecanoate/oleic acid solution, 400-μg/mL of the lanthanum (III) tri 9,10-diacetoxy octadecanoate/oleic acid solution, 500-μg/mL of the lanthanum (III) tri 9,10-diacetoxy octadecanoate/oleic acid solution, 600-μg/mL of the lanthanum (III) tri 9,10-diacetoxy octadecanoate/oleic acid solution, 700-μg/mL of the lanthanum (III) tri 9,10-diacetoxy octadecanoate/oleic acid solution, 800-μg/mL of the lanthanum (III) tri 9,10-diacetoxy octadecanoate/oleic acid solution, 900-μg/mL of the lanthanum (III) tri 9,10-diacetoxy octadecanoate/oleic acid solution, 1000-μg/mL of the lanthanum (III) tri 9,10-diacetoxy octadecanoate/oleic acid solution, 2000-μg/mL of the lanthanum (III) tri 9,10-diacetoxy octadecanoate/oleic acid solution.

In yet another preferred embodiment, the polysaccharides solution comprises 25-mg of gum Arabic, 25-mg of guar gum, and 25-mg of carrageenan in hot water. The solution is stirred until a uniform consistency is achieved and the solution has thickened. The saline-phosphate solution comprises hot 0.9% saline solution mixed with 4-mg/mL of sodium phosphate dibasic, 4-mg/mL of titanium dioxide, 0.9% citric acid monohydrate, and 1% acetic acid. This solution is sterile filtered and then added to the polysaccharide solution in a 2 parts saline-phosphate solution to 8-parts of polysaccharide solution. To this polysaccharide/saline-phosphate solution, 200-μl of the lanthanum (III) tri 9,10-diacetoxy octadecanoate/oleic acid solution (1-g/mL) is added and then vortexed, or agitated with a rotor such an immersion blender, or processed using a rotor-stator for at least 3-minutes to create the stable emulsion. When administered at 10-μl to each cubic centimeter of material (v/v) this results in a final concentration of 200-ng lanthanum (III) tri 9,10-diacetoxy octadecanoate solution per cubic centimeter (cc), or milliliter (mL), or gram (g), or any equivalent measure of volume.

Cell Proliferation and Cell Death Assays:

Cells were treated with the 200-ng lanthanum (III) tri 9,10-diacetoxy octadecanoate solution and tested for its effects on cell proliferation using the MTT assay and 2000-ng lanthanum (III) tri 9,10-diacetoxy octadecanoate solution cell death using the LDH (lactate dehydrogenase) assay.

Figures 5A, 5B:
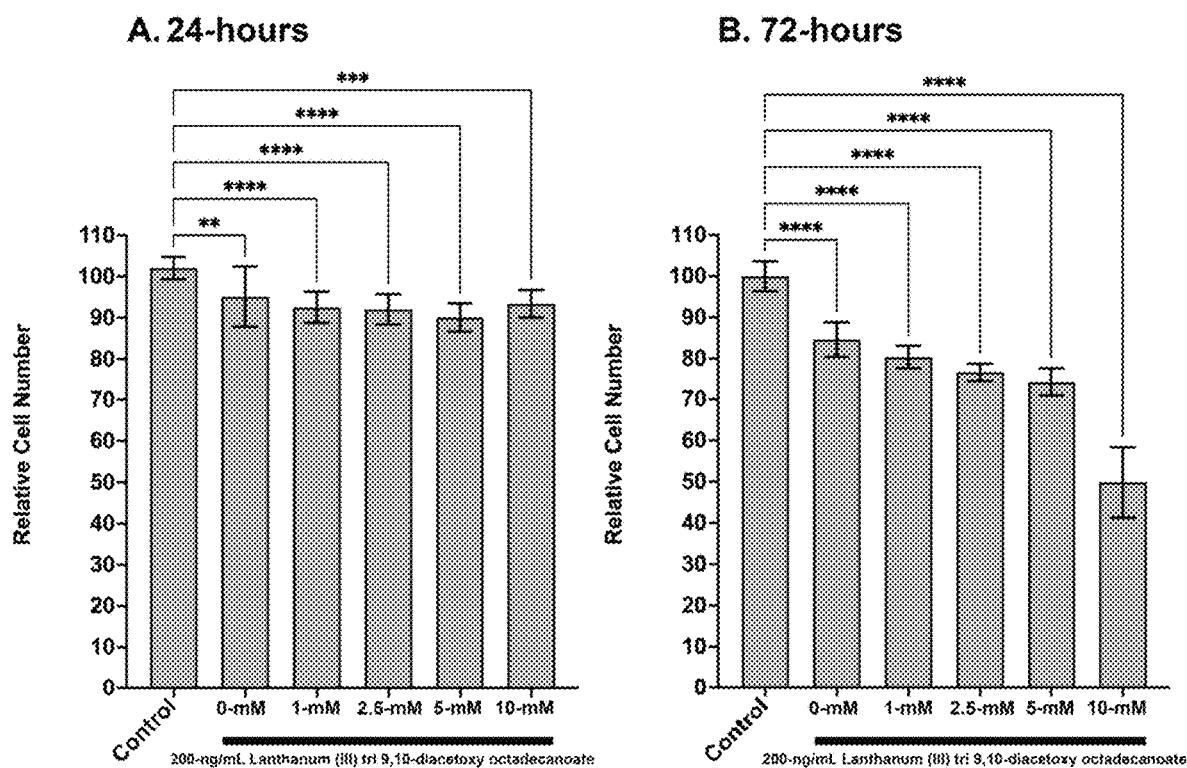
FIG. 5A-5B shows MTT Proliferation Assay for 200-ng lanthanum (III) tri 9,10-diacetoxy octadecanoate solution, with or without the addition of N-allyl noroxymorphone.

The MTT Assay of Cell Proliferation: The MTT assay provides a measurement of cell proliferation (FIG. 5) in the MCF7 breast cancer cells. Cells were treated with 200-ng lanthanum (III) tri 9,10-diacetoxy octadecanoate solution containing 0-mM, 1-mM, 2.5-mM, 5-mM, and 10-mM of N-allyl noroxymorphone. Experiments were conducted using three independent replicates and evaluated using a 1-way ANOVA. Relative to Controls at 24-hours (FIG. 5A), there was between a 6.9% and 11.94% decrease in cell number (=$p<0.0034$, *=$p<0.0007$, and **=$p<0.0001$). Relative to Control cultures at 72-hours (FIG. 5B), there was between a 15.4% and 50.2% decrease in cell number (**=$p<0.0001$). The 200-ng lanthanum (III) tri 9,10-diacetoxy octadecenoate solution containing 10-mM N-allyl noroxymorphone was the most effective.

Figures 6A, 6B:
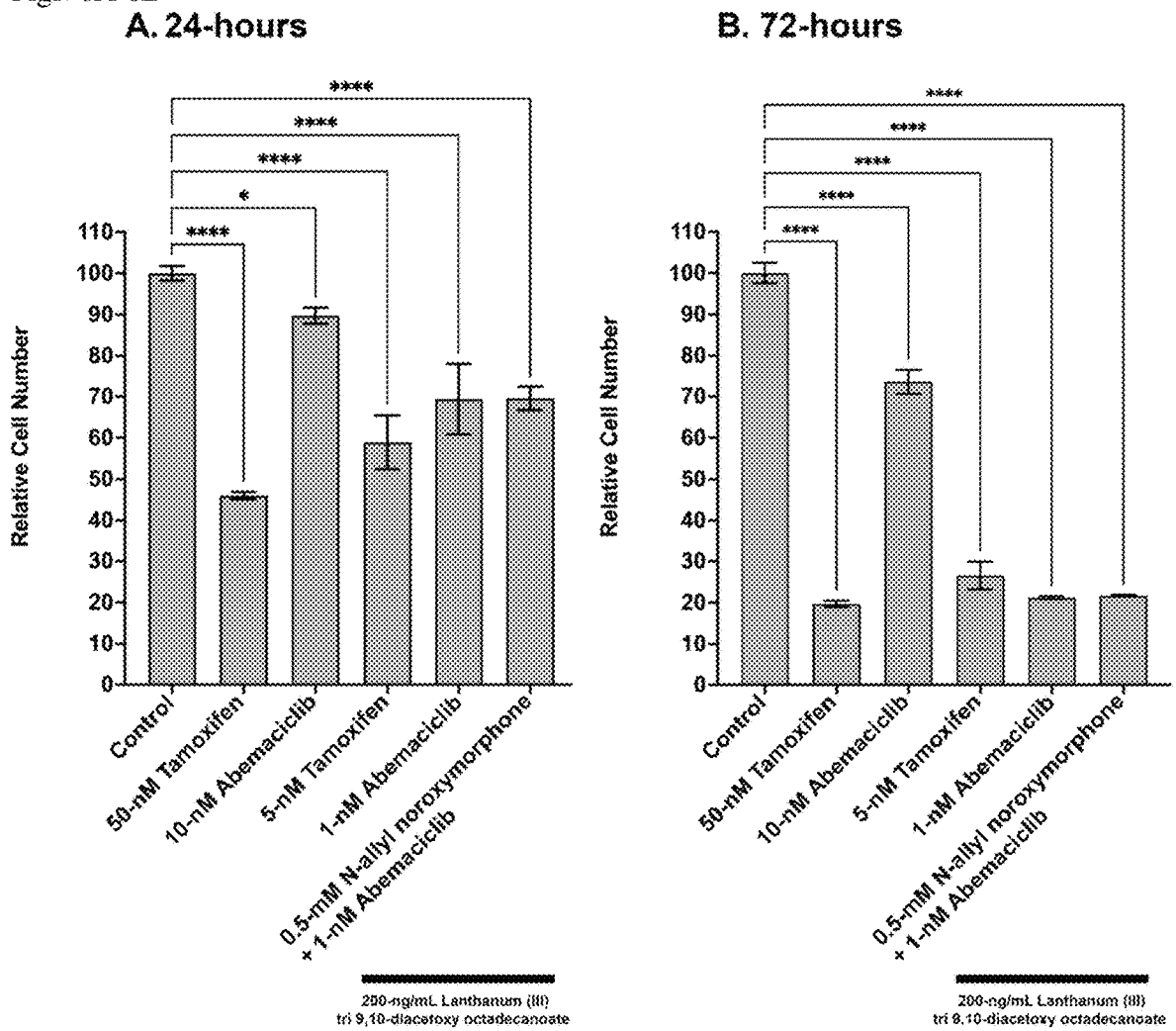
FIG. 6A-6B shows MTT Proliferation Assay for 200-ng lanthanum (III) tri 9,10-diacetoxy octadecanoate solution, with or without the addition of N-allyl noroxymorphone, Tamoxifen, or Abemaciclib.

Combination Therapy Assessed Using the MTT Assay of Cell Proliferation: The MTT assay provides a measurement of cell proliferation (FIG. 5) in the MCF7 breast cancer cells. Cells were treated with 200-ng lanthanum (III) tri 9,10-diacetoxy octadecanoate solution containing 5-nM Tamoxifen, 1-nM Abemaciclib, or 1-nM Abemaciclib+1-mM of N-allyl noroxymorphone (FIG. 6). Control cultures were treated with 50-nM of Tomoxifen or 10-nM of Abemaciclib.

Relative to Control cultures (i.e., no treatment) at 24-hours (FIG. 6A), there was a 54% decrease in cell number following 50-nM Tamoxifen therapy (**=$p<0.0001$), a 10.2% decrease in cell number following 10-nM Abemaciclib therapy (NS, $p<0.1021$), a 41% decrease in cell number when 5-nM Tamoxifen was added to the 200-ng lanthanum (III) tri 9,10-diacetoxy octadecanoate solution (=$p<0.0001$), a$^3$0.6% decrease in cell number when 1-nM of Abemaciclib was added to the 200-ng lanthanum (III) tri 9,10-diacetoxy octadecanoate solution (=$p<0.0001$), and a 25.7% decrease in cell number when 1-mM of N-allyl noroxymorphone and 1-nM of Abemaciclib are added to the 200-ng lanthanum (III) tri 9,10-diacetoxy octadecanoate solution (=$p<0.0001$). Relative to Control cultures (i.e., no treatment) at 72-hours (FIG. 6B), there was a 80.3% decrease in cell number following 50-nM Tamoxifen therapy (=$p<0.0001$), a 26.4% decrease in cell number following 10-nM Abemaciclib therapy (, $p<0.0001$)), a 73.5% decrease in cell number when 5-nM Tamoxifen was added to the 200-ng lanthanum (III) tri 9,10-diacetoxy octadecanoate solution (=$p<0.0001$), a 78.8% decrease in cell number when 1-nM of Abemaciclib was added to the 200-ng lanthanum (III) tri 9,10-diacetoxy octadecanoate solution (=$p<0.0001$), and a 78.4% decrease in cell number when 1-mM of N-allyl noroxymorphone and 1-nM of Abemaciclib are added to the 200-ng lanthanum (III) tri 9,10-diacetoxy octadecanoate solution (**=$p<0.0001$).

Figure 7:
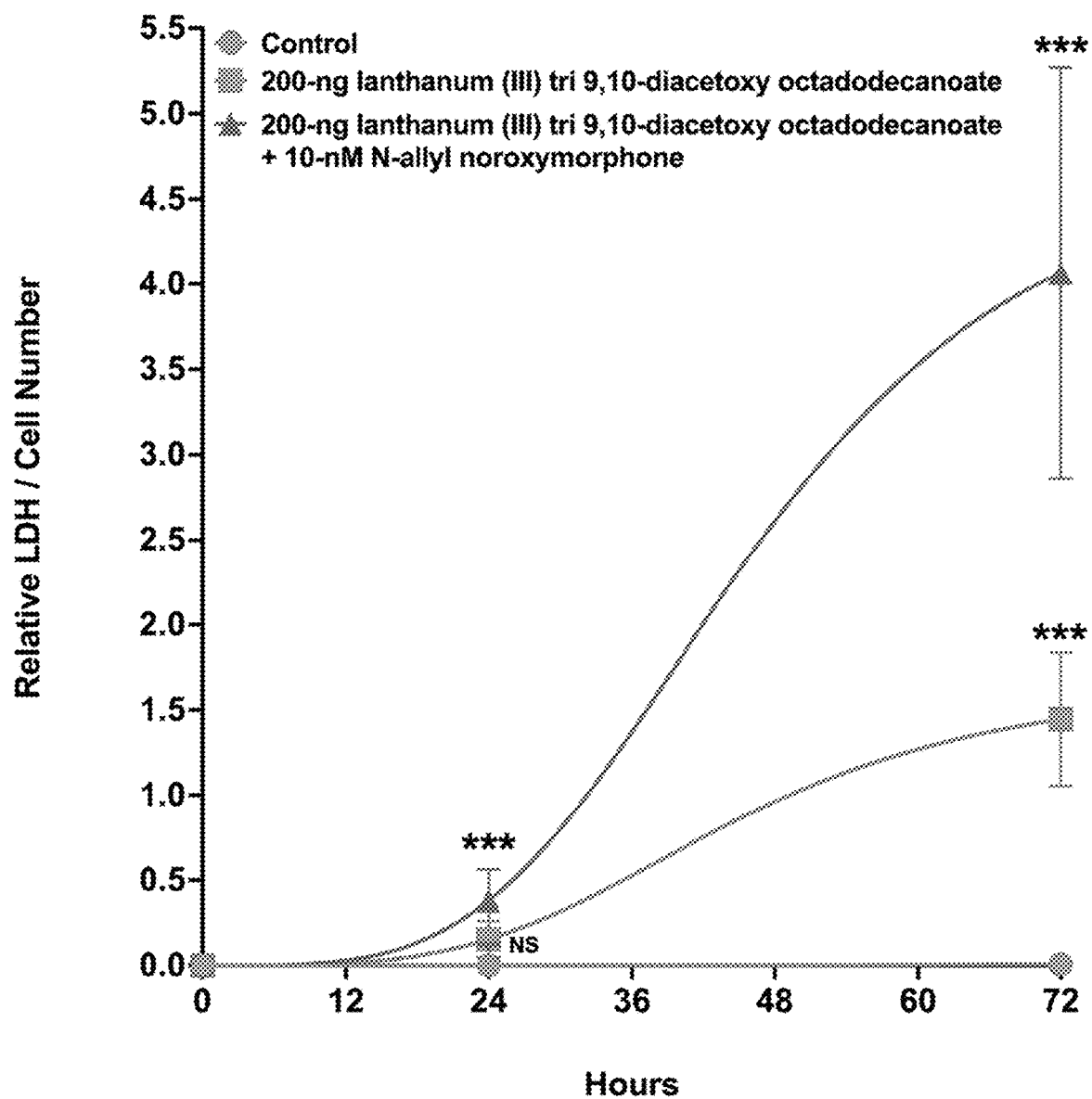
FIG. 7 Shows LDH Cell Death Assay for 2000-ng lanthanum (III) tri 9,10-diacetoxy octadecanoate solution, with or without the addition of N-allyl noroxymorphone.

LDH Assay of Cell Death: The LDH assay is used to measure cell death. For example, cell cultures with lower LDH relative to the control have lower cell death. MCF7 hormone receptor positive breast cancer cells were treated with a 2000-ng lanthanum (III) tri 9,10-diacetoxy octadecanoate solution with or without 10-mM of N-allyl noroxymorphone added and tested for its effects on cell death (FIG. 7). Following treatment with the 2000-ng lanthanum (III) tri 9,10-diacetoxy octadecanoate solution with or without 10-mM N-allyl noroxymorphone, MCF7 breast cancer cell cultures were evaluated using non-linear regression to determine differences between groups. Regression lines were shown to be significantly different via an Extra-Sum-of-Squares F-test (p<0.0001). 1-way ANOVA used to determine differences at time-points. At 24-hrs the 2000-ng lanthanum (III) tri 9,10-diacetoxy octadecanoate solution with 10-mM N-allyl noroxymorphone produced a 38.7% increase in LDH (i.e., cell death) vs Controls (*=p<0.001). Whereas, at 24-hrs the 2000-ng lanthanum (III) tri 9,10-diacetoxy octadecanoate solution alone had a 15% increase in LDH (i.e., cell death) vs Controls (NS=not significant). At 72-hrs the 2000-ng lanthanum (III) tri 9,10-diacetoxy octadecanoate solution with 10-mM N-allyl noroxymorphone had a 407% increase in LDH (i.e., cell death) vs Controls (*=p<0.0001). While at 72-hrs the 2000-ng lanthanum (III) tri 9,10-diacetoxy octadecanoate solution alone produced a 145% increase in LDH (i.e., cell death) vs Controls (***=p<0.0209).

EQUIVALENTS

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

SEQUENCE LISTING

```
Sequence total quantity: 6
SEQ ID NO: 1              moltype = AA  length = 5
FEATURE                   Location/Qualifiers
source                    1..5
                          mol_type = protein
                          organism = synthetic construct
SEQUENCE: 1
YGGFM                                                                     5

SEQ ID NO: 2              moltype = AA  length = 5
FEATURE                   Location/Qualifiers
source                    1..5
                          mol_type = protein
                          organism = synthetic construct
SEQUENCE: 2
YGGFL                                                                     5

SEQ ID NO: 3              moltype = AA  length = 8
FEATURE                   Location/Qualifiers
source                    1..8
                          mol_type = protein
                          organism = synthetic construct
SITE                      1
                          note = D-amino acid
SITE                      4
                          note = D-amino acid
SITE                      7
                          note = Penicillamine
SITE                      8
                          note = Amidated residue
SEQUENCE: 3
FCYWKTXT                                                                  8

SEQ ID NO: 4              moltype = AA  length = 50
FEATURE                   Location/Qualifiers
source                    1..50
                          mol_type = protein
                          organism = synthetic construct
SEQUENCE: 4
QSALDYFMFA VRCRHQRRQL VHFAWEHFRP RCKFVWGPQD KLRRFKPSSL                    50

SEQ ID NO: 5              moltype = AA  length = 8
FEATURE                   Location/Qualifiers
source                    1..8
                          mol_type = protein
                          organism = synthetic construct
SITE                      3
                          note = 2-Aminobutyric acid
SITE                      8
                          note = Amidated para-fluoro-substituted phenylalanine
SEQUENCE: 5
AAXRRLIF                                                                  8

SEQ ID NO: 6              moltype = AA  length = 8
FEATURE                   Location/Qualifiers
source                    1..8
                          mol_type = protein
                          organism = synthetic construct
```

```
SITE            8
                note = Amidated residue
SEQUENCE: 6
HAKRRLIF                                                              8
```

What is claimed is:

1. A lanthanide (III) 9-R', 10-R" tri octadecanoate compound of the formula:

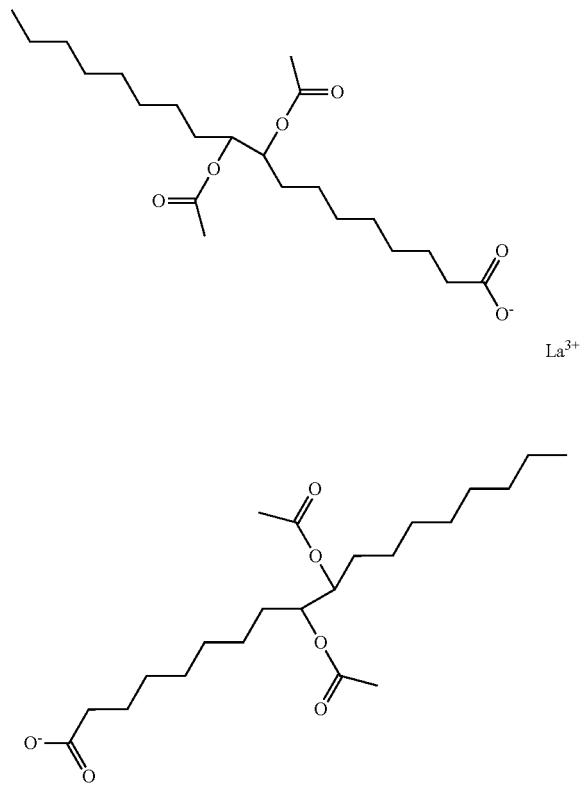

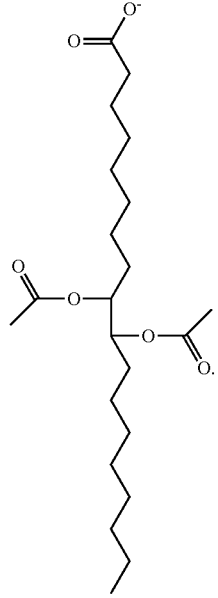

2. A pharmaceutical composition comprising the compound of claim 1 and a pharmaceutically acceptable carrier.

3. A pharmaceutical composition comprising the compound of claim 1, a pharmaceutically acceptable carrier, and N-allyl noroxymorphone or a salt thereof.

4. A pharmaceutical composition comprising the compound of claim 2, a pharmaceutically acceptable carrier, and a CDK4/6 inhibitor i-s-selected from the group consisting of palbociclib, ribociclib, and abemaciclib.

5. The pharmaceutical composition of claim 4, further comprising N-allyl noroxymorphone.

\* \* \* \* \*